(12) United States Patent
Greenhalgh et al.

(10) Patent No.: US 11,583,416 B2
(45) Date of Patent: Feb. 21, 2023

(54) BONE GRAFT DELIVERY SYSTEM AND METHOD FOR USING SAME

(71) Applicant: SurGenTec, LLC, Boca Raton, FL (US)

(72) Inventors: Travis Greenhalgh, Boca Raton, FL (US); Ryan Lewis, Waxhaw, NC (US)

(73) Assignee: SurGenTec, LLC, Boca Raton, FL (US)

( * ) Notice: Subject to any disclaimer, the term of this patent is extended or adjusted under 35 U.S.C. 154(b) by 416 days.

(21) Appl. No.: 16/752,379

(22) Filed: Jan. 24, 2020

(65) Prior Publication Data

US 2020/0229946 A1 Jul. 23, 2020

Related U.S. Application Data

(63) Continuation of application No. 15/614,435, filed on Jun. 5, 2017, now Pat. No. 10,543,105, which is a continuation of application No. 14/214,031, filed on Mar. 14, 2014, now Pat. No. 9,668,881.

(60) Provisional application No. 61/883,940, filed on Sep. 27, 2013, provisional application No. 61/798,513, filed on Mar. 15, 2013.

(51) Int. Cl.
| | | |
|---|---|---|
| A61F 2/46 | (2006.01) | |
| A61B 17/16 | (2006.01) | |
| A61B 17/88 | (2006.01) | |
| A61B 34/20 | (2016.01) | |
| A61B 90/57 | (2016.01) | |

(Continued)

(52) U.S. Cl.
CPC ........ *A61F 2/4601* (2013.01); *A61B 17/1635* (2013.01); *A61B 17/1659* (2013.01); *A61B 17/1671* (2013.01); *A61B 17/8805* (2013.01); *A61B 34/20* (2016.02); *A61B 90/40* (2016.02); *A61B 90/57* (2016.02); *A61F 2/4611* (2013.01); *A61F 2/4455* (2013.01)

(58) Field of Classification Search
CPC ....... A61F 2/4601; A61F 2/44; A61B 17/1659
See application file for complete search history.

(56) References Cited

U.S. PATENT DOCUMENTS

| | | |
|---|---|---|
| 2,316,095 A | 4/1943 | Mead, Jr. |
| 4,277,184 A | 7/1981 | Solomon |

(Continued)

OTHER PUBLICATIONS

Globus Medical Allocate product, http://www.globusmedical.com/portfolio/allocate/, 2014, 2 pp.

(Continued)

*Primary Examiner* — Andrew Yang
(74) *Attorney, Agent, or Firm* — Knobbe Martens Olson & Bear, LLP

(57) ABSTRACT

A bone graft delivery system can include an elongate tube and a handle having a trigger and a ratcheting mechanism. The trigger is actuated to deliver bone graft material through the tube. The bone graft delivery system can further include a distal tip at a distal end of the tube. The tip has one or more openings to deliver the bone graft material to a desired location and includes a surface suitable to act as a rasp for decorticating bone. A method for delivering bone graft material to a desired surgical location includes providing a bone graft delivery device, positioning the device adjacent the surgical location, decorticating bone, and delivering bone graft material to the surgical location.

20 Claims, 58 Drawing Sheets

(51) Int. Cl.
*A61B 90/40* (2016.01)
*A61F 2/44* (2006.01)

(56) References Cited

U.S. PATENT DOCUMENTS

| | | |
|---|---|---|
| 4,338,925 A | 7/1982 | Miller |
| 4,801,263 A | 1/1989 | Clark |
| 5,531,749 A | 7/1996 | Michelson |
| 5,733,288 A | 3/1998 | Allen |
| 6,224,607 B1 * | 5/2001 | Michelson ............ A61B 17/025 623/17.16 |
| 6,439,439 B1 | 8/2002 | Rickard et al. |
| 6,676,664 B1 | 1/2004 | Al-Assir et al. |
| 6,793,660 B2 | 9/2004 | Kerr et al. |
| 6,814,736 B2 | 11/2004 | Reiley et al. |
| 7,141,054 B2 | 11/2006 | Vandewalle |
| 7,306,603 B2 | 12/2007 | Boehm, Jr. et al. |
| 7,513,901 B2 | 4/2009 | Seifert et al. |
| 7,578,820 B2 * | 8/2009 | Moore .................. A61F 2/4611 600/203 |
| 7,799,033 B2 | 9/2010 | Assell et al. |
| 7,811,291 B2 | 10/2010 | Liu et al. |
| 7,887,543 B2 | 2/2011 | Sand et al. |
| 7,909,833 B2 | 3/2011 | Voellmicke |
| 8,308,805 B2 | 11/2012 | Lynn et al. |
| 8,628,536 B2 | 1/2014 | Walker et al. |
| 8,696,679 B2 | 4/2014 | Shadduck et al. |
| 8,932,295 B1 | 1/2015 | Greenhalgh |
| 8,945,137 B1 | 2/2015 | Greenhalgh et al. |
| 9,173,694 B2 * | 11/2015 | Kleiner ................ A61F 2/447 |
| 9,456,830 B2 | 10/2016 | Greenhalgh |
| 9,655,748 B2 | 5/2017 | Greenhalgh et al. |
| 9,668,881 B1 | 6/2017 | Greenhalgh et al. |
| 10,123,849 B2 | 11/2018 | Greenhalgh |
| 10,238,507 B2 | 3/2019 | Greenhalgh et al. |
| 10,292,747 B2 | 5/2019 | Greenhalgh et al. |
| 10,405,905 B2 | 9/2019 | Greenhalgh |
| 10,543,105 B2 | 1/2020 | Greenhalgh |
| 10,687,828 B2 | 6/2020 | Greenhalgh et al. |
| 11,116,647 B2 | 9/2021 | Greenhalgh et al. |
| 2004/0024409 A1 | 2/2004 | Sand et al. |
| 2004/0133211 A1 | 7/2004 | Raskin et al. |
| 2004/0215201 A1 | 10/2004 | Lieberman |
| 2005/0107800 A1 | 5/2005 | Frankel et al. |
| 2005/0137604 A1 | 6/2005 | Assell et al. |
| 2005/0171549 A1 | 8/2005 | Boehm Jr. et al. |
| 2005/0203523 A1 | 9/2005 | Wenstrom Jr. et al. |
| 2006/0293687 A1 | 12/2006 | Bogert |
| 2007/0005072 A1 | 1/2007 | Castillo et al. |
| 2007/0043376 A1 | 2/2007 | Leatherbury et al. |
| 2007/0276397 A1 | 11/2007 | Pacheco |
| 2007/0289998 A1 | 12/2007 | Keller |
| 2008/0065082 A1 | 3/2008 | Chang et al. |
| 2008/0071284 A1 | 3/2008 | Lechmann |
| 2008/0125856 A1 | 5/2008 | Perez-Cruet et al. |
| 2008/0300684 A1 | 12/2008 | Shelokov |
| 2009/0149707 A1 * | 6/2009 | Brannon ................ A61B 1/313 600/114 |
| 2009/0216238 A1 | 8/2009 | Stark |
| 2009/0318925 A1 | 12/2009 | Campion et al. |
| 2010/0036381 A1 | 2/2010 | Vanleeuwen |
| 2010/0057087 A1 | 3/2010 | Cha |
| 2010/0174286 A1 | 7/2010 | Truckai et al. |
| 2010/0179556 A1 | 7/2010 | Scribner |
| 2010/0204702 A1 | 8/2010 | Lechot et al. |
| 2010/0262146 A1 | 10/2010 | Tulkis |
| 2011/0071527 A1 | 3/2011 | Nelson et al. |
| 2011/0071536 A1 | 3/2011 | Kleiner et al. |
| 2011/0218513 A1 | 9/2011 | Walker et al. |
| 2012/0253316 A1 | 10/2012 | Oktavec et al. |
| 2013/0131683 A1 | 3/2013 | Shah et al. |
| 2014/0252044 A1 | 9/2014 | Greter et al. |
| 2015/0018886 A1 | 1/2015 | Ali |
| 2015/0105748 A1 | 4/2015 | McBride et al. |
| 2017/0354515 A1 | 12/2017 | Greenhalgh |
| 2019/0247201 A1 | 8/2019 | Greenhalgh |
| 2020/0069352 A1 | 3/2020 | Greenhalgh |
| 2020/0129309 A1 | 4/2020 | Greenhalgh et al. |
| 2022/0257387 A1 | 8/2022 | Greenhalgh |

OTHER PUBLICATIONS

Third Party Submission Under 37 CFR 1.290 dated Apr. 4, 2017 in U.S. Appl. No. 14/992,954.

* cited by examiner

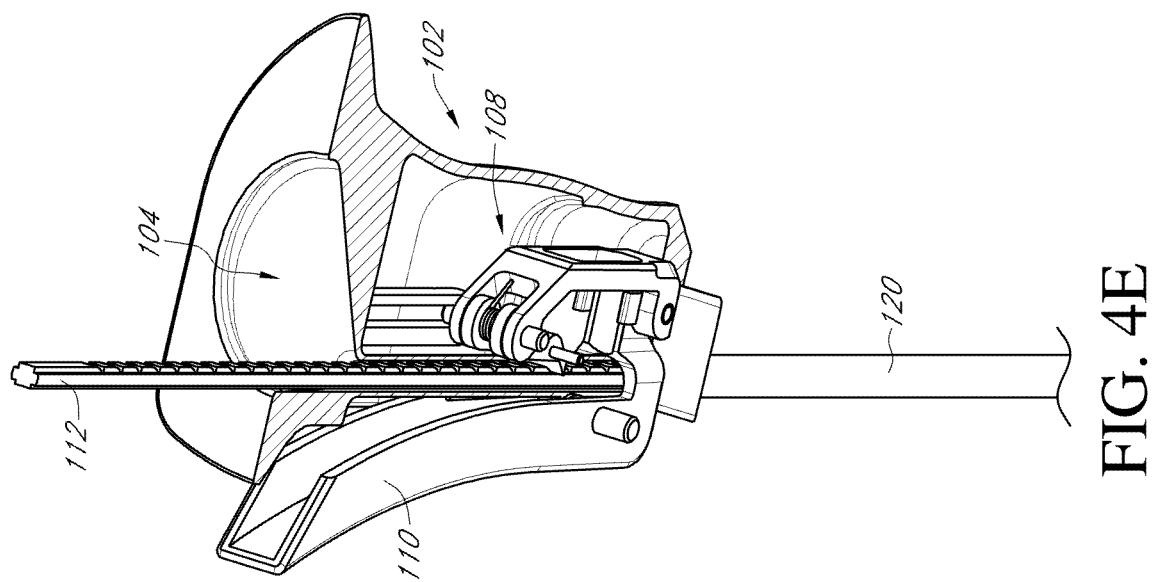

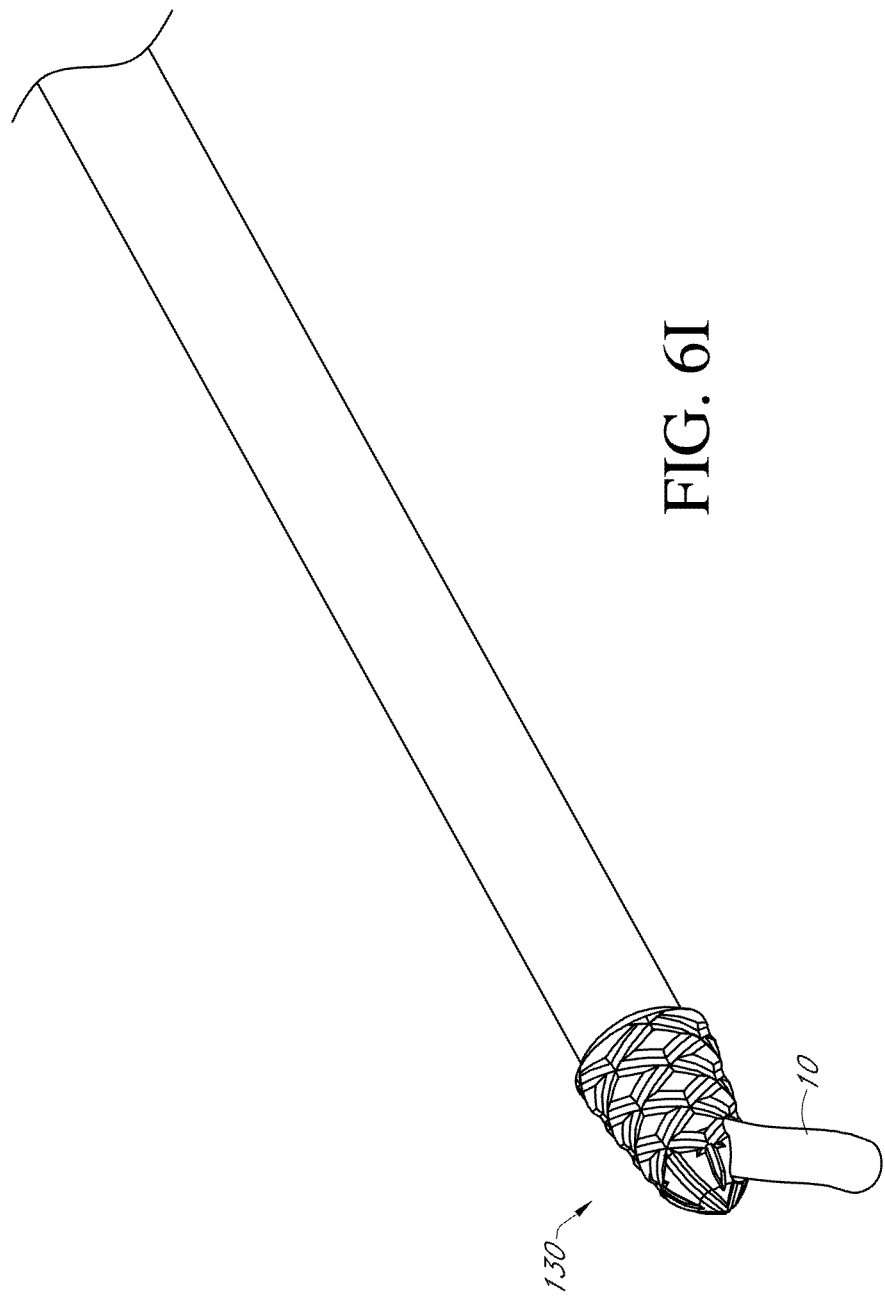

BONE GRAFT DELIVERY SYSTEM AND METHOD FOR USING SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 15/614,435, filed Jun. 5, 2017, which is a continuation of U.S. patent application Ser. No. 14/214,031, filed Mar. 14, 2014, and issued as U.S. Pat. No. 9,668,881 on Jun. 6, 2017, which claims priority benefit of U.S. Provisional Application Nos. 61/798,513, filed Mar. 15, 2013, and 61/883,940, filed Sep. 27, 2013, the entirety of each of which is hereby incorporated by reference herein and should be considered a part of this specification.

BACKGROUND

Field

The present application relates to orthopedic surgery in general, and more particularly, to bone graft delivery systems and methods.

Description of the Related Art

In a bone grafting procedure, a surgeon places bone or a bone substitute into an area in a patient's body to provide a type of scaffold for bone growth and repair. Bone grafts can be used to help treat various orthopedic problems, for example, to fuse a joint or repair a fracture. Bone graft material can be, for example, autogenous (harvested from the patient's own body), allogeneic (harvested from another person, usually a cadaver), or synthetic. Many bone grafting procedures are performed via open surgery implantation. However, these procedures can also be performed minimally invasively, for example, by using a needle to inject the bone graft material into the target location without requiring a surgical incision.

In some cases decortication of the bony area receiving the graft is performed prior to delivery of the bone graft material. Decortication removes superficial cortical bone and exposes the underlying cancellous bone, which can help accelerate the integration of the bone graft with the native bone.

SUMMARY

The devices, systems, and methods described herein allow for minimally invasive delivery of bone graft material to a desired location in a patient's body. In some embodiments, the devices, systems, and methods described herein allow for delivery of bone graft material to a desired location in an open or mini-open procedure. In some embodiments, the devices, systems, and methods described herein also provide for bone decortication.

In some embodiments, a bone graft delivery system includes an elongated tube, a handle at a proximal end of the tube, and a tip at a distal end of the tube. The handle is configured to be actuated to deliver bone graft material through the tube. The tip includes one or more openings configured to deliver the bone graft material to a desired location and a surface suitable to serve as a rasp for scraping bone.

In some embodiments, the rasping surface of the tip includes jagged edges. The tip can be made of a metal, a radiopaque material, a durable medical plastic, a composite material, or another material or combination of materials. In some embodiments, the tip includes one or more radiopaque markers. The tip can have a sharp or blunt end. The tip can be removably attachable to the distal end of the tube. Alternatively, the tip can be integrally formed or permanently coupled to the distal end of the tube. In some embodiments the tube is rigid. In other embodiments the tube is at least somewhat bendable. In some embodiments the tube is straight, while in other embodiments the tube includes a permanent bend. The handle can include a trigger configured to be actuated to deliver the bone graft material through the tube. In some embodiments, the bone graft delivery system includes an endoscopic camera positioned adjacent the tip.

In some embodiments, a method for delivering bone graft material to a surgical location includes providing a bone graft delivery device and positioning the device adjacent the surgical location. The bone graft delivery device comprises an elongate tube and a distal tip. The distal tip includes at least one opening for delivering the bone graft material to the surgical location. The method further includes decorticating bone with the distal tip and delivering bone graft material through the tube and out the at least one opening of the tip.

The bone graft material can be one or more autogenous, allogenic, cadaveric, and/or synthetic materials. In some embodiments, the bone graft delivery device is positioned at the surgical location through a minimally invasive opening in a patient's skin. In some embodiments, the surgical location is a portion of the patient's spine, so the bone graft delivery device is positioned adjacent to the spine and the distal tip decorticates a portion of the spine. In some embodiments, decorticating bone with the distal tip is accomplished by rasping bone with jagged edges of the distal tip. In some embodiments, bone is decorticated with the distal tip by actuating the distal tip with mechanical, battery powered, electric, pneumatic, or other means of force.

BRIEF DESCRIPTION OF THE DRAWINGS

FIGS. 4A-4E are section views illustrating operation of an example embodiment of a ratcheting mechanism in a handle of a bone graft delivery device;

FIG. 4O illustrates an exploded view of the bone graft delivery device of FIG. 4N;

FIG. 6I illustrates the distal tip of FIG. 6H extruding bone graft material;

DETAILED DESCRIPTION

Figure 1A:
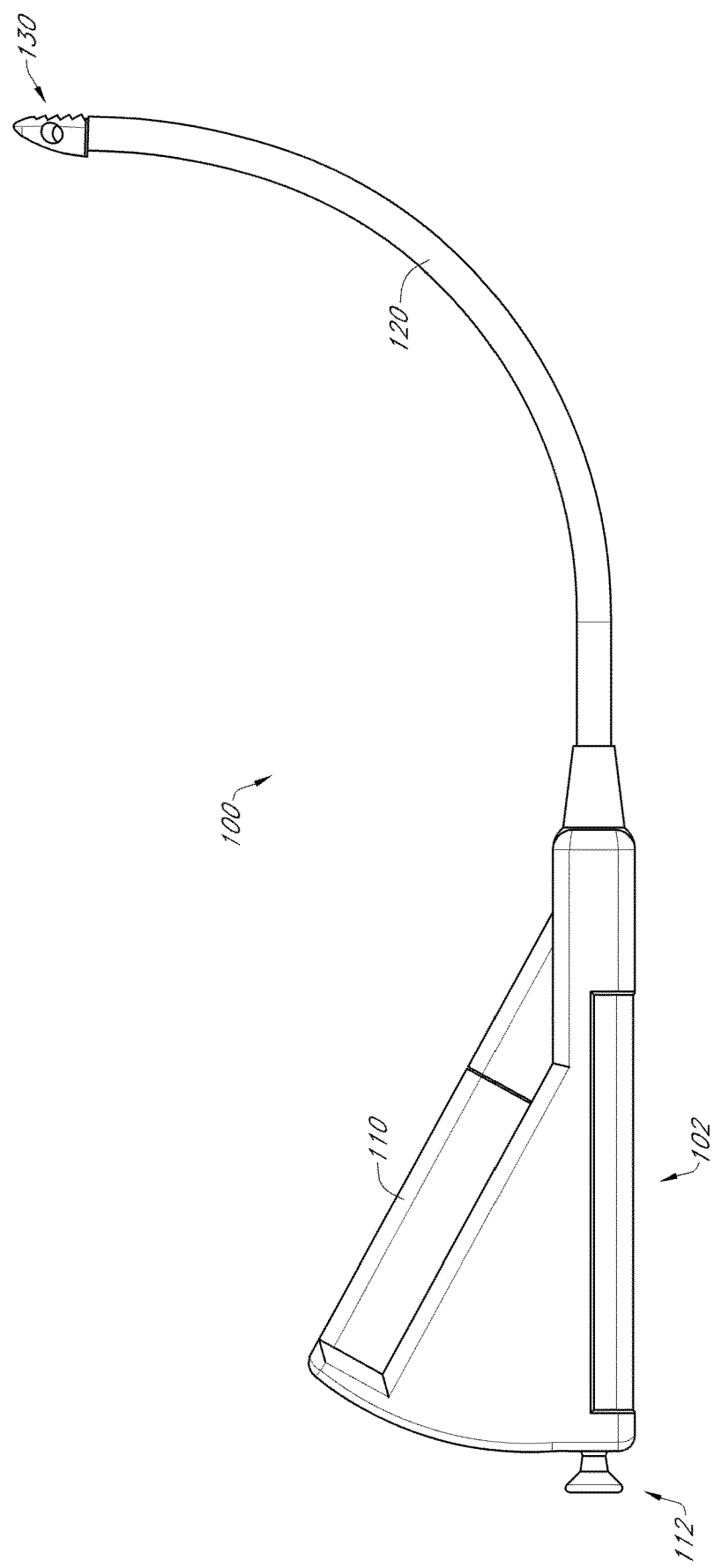
FIG. 1A illustrates a side view of an example embodiment of a bone graft delivery device.
Figure 1B:
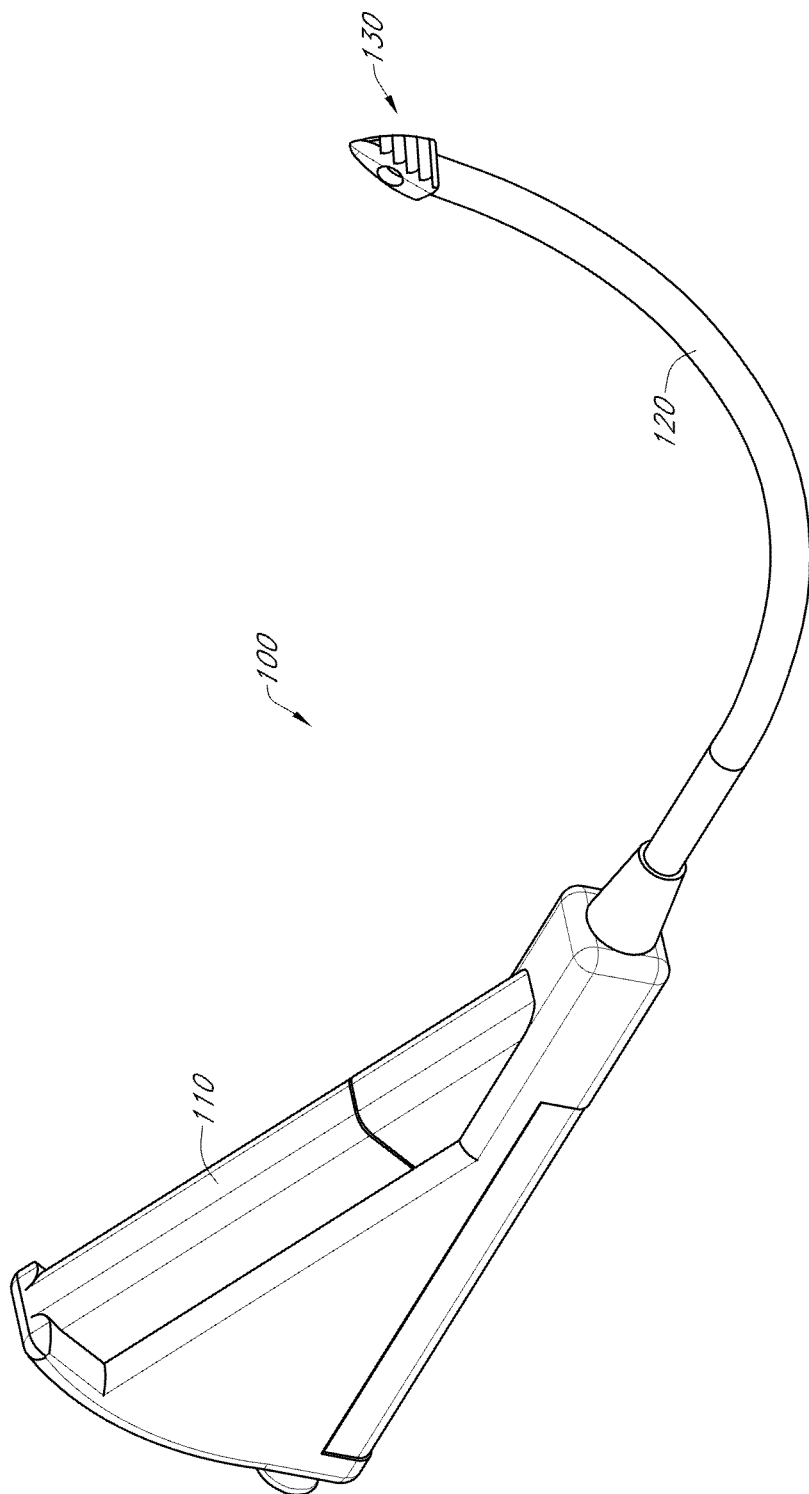
FIG. 1B illustrates a perspective view of the bone graft delivery device of FIG. 1A.

As shown in FIGS. 1A and 1B, an example embodiment of a bone graft delivery device 100 generally includes a handle 102 having a trigger 110 or other actuation mechanism, a tube 120 having a lumen therethrough, and a distal tip 130. In the illustrated embodiment, the bone graft delivery device 100 is similar to a caulking gun. The handle 102 can house a supply of the desired bone graft material. The bone graft material can be pre-loaded in the handle 102 or tube 120 or can be supplied to the handle, for example, via a cartridge that can be removably coupled to the handle 102. In some embodiments, the device 100 can further include a plunger 112 that is retracted proximally to allow the handle to receive a cartridge or pre-loaded volume of bone graft material. In some embodiments, for example as shown in the example embodiment of FIGS. 2A and 2B, the bone graft delivery device 100 does not include a distal tip 130. In some embodiments, the bone graft delivery device does not include a rasping distal tip as described in greater detail herein.

In use, the trigger 110 is actuated to deliver bone graft material through the tube 120 and distal tip 130 to a desired surgical location. In some embodiments, the plunger 112 is simultaneously pushed distally to help deliver bone graft material through the tube 120. In some embodiments, the trigger 110 or other actuation mechanism is configured to deliver a controlled release amount of bone graft material during actuation of the device, for example, ½ cc of bone graft material per complete squeeze of the trigger 110. The trigger 110 or other actuation mechanism may be operated manually or by mechanical, battery powered, electric, pneumatic, or any other means of force.

Figure 2A:
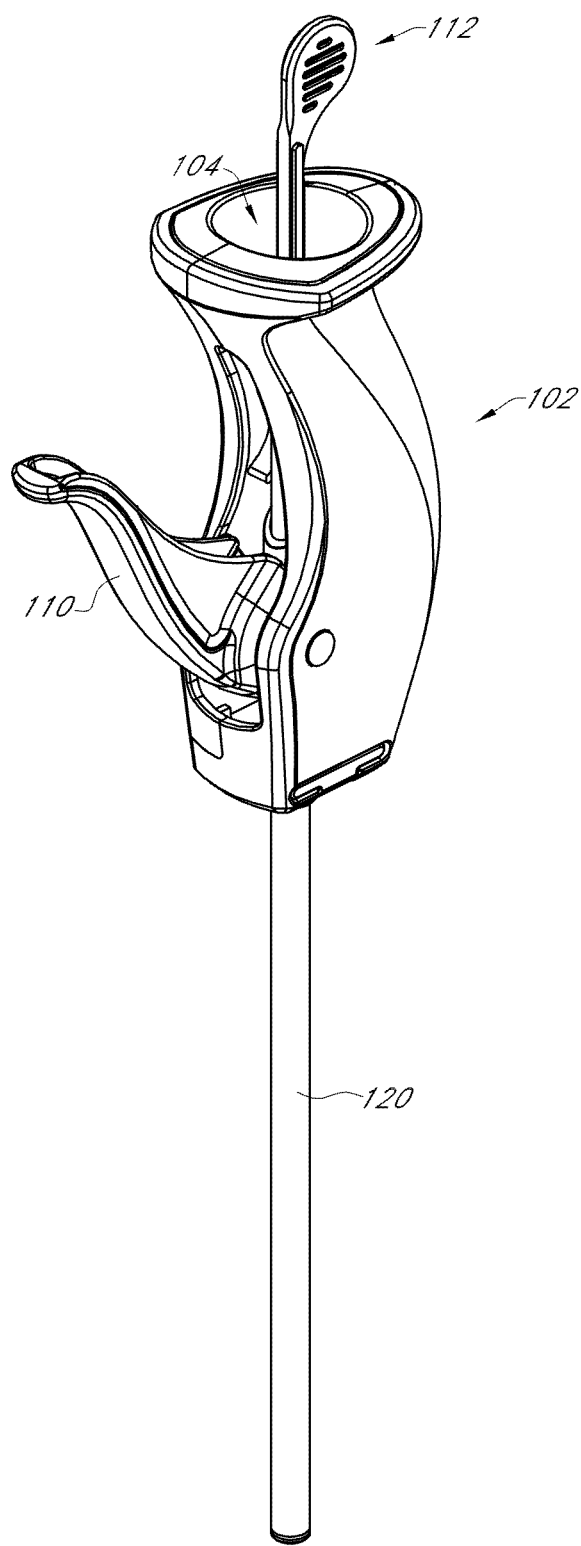
FIGS. 2A and 2B illustrate perspective views of another example embodiment of a bone graft delivery device.
Figure 2B:
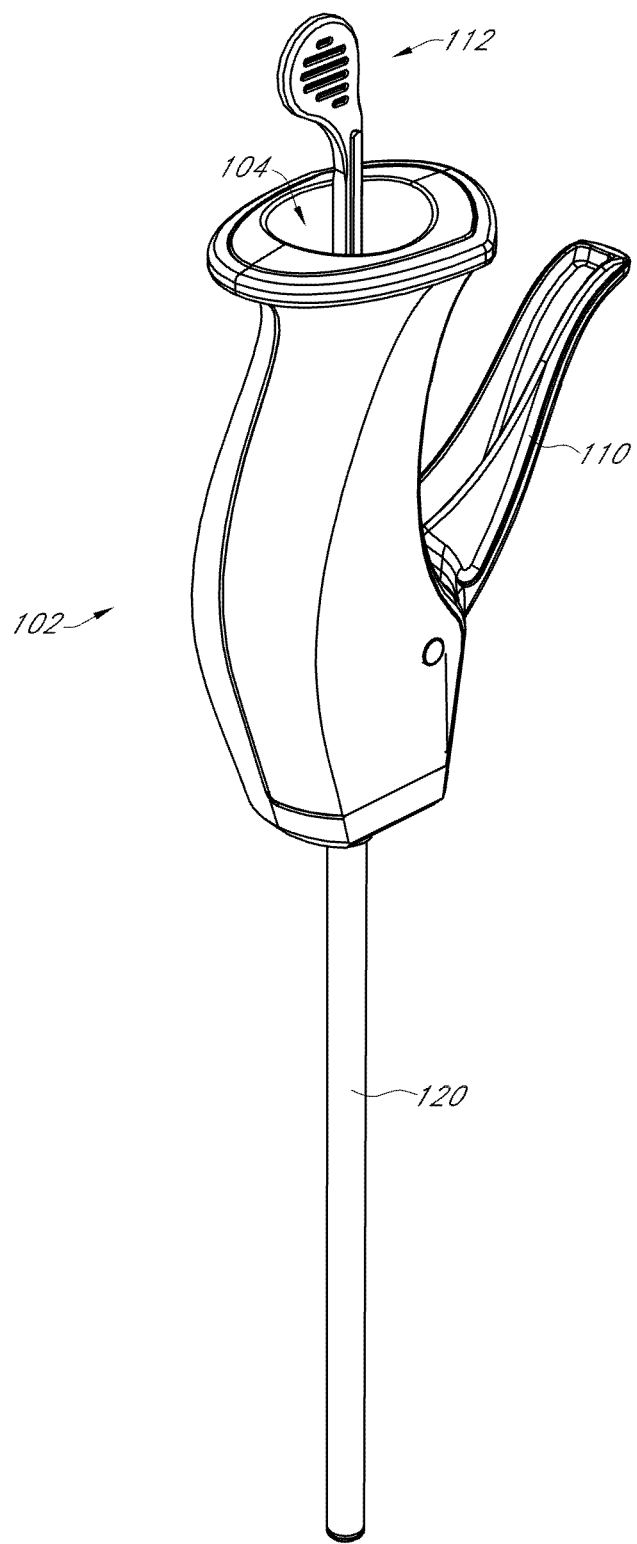

In some embodiments, a portion of the handle 102 can include an opening configured to receive the bone graft material. For example, a base of the handle 102 can include a funnel 104 as shown in FIGS. 2A-2B and 3. In other embodiments, a side or another portion of the handle 102 can include a funnel 104 or other opening configured to receive the bone graft material, for example as shown in FIGS. 2C-2K. Whereas some existing bone graft delivery devices are only compatible with certain, e.g., pre-packaged, bone graft materials, the funnel 104 can be designed to advantageously allow the user to use any bone graft material or combination of bone graft materials he or she wishes or deems appropriate. For example, the user can use synthetic, autologous, stem cell, DMB, cadaveric, and/or any other available bone graft material. The handle 102 can further include a channel or funnel shaft 106 extending therethrough connecting and in fluid communication with the funnel 104 and tube 120. In use, the user can mix the desired bone graft material in the funnel 104, then use the plunger 112 or other means to advance the bone graft material through the channel 106 and into the tube 120 for delivery.

Figure 4A:
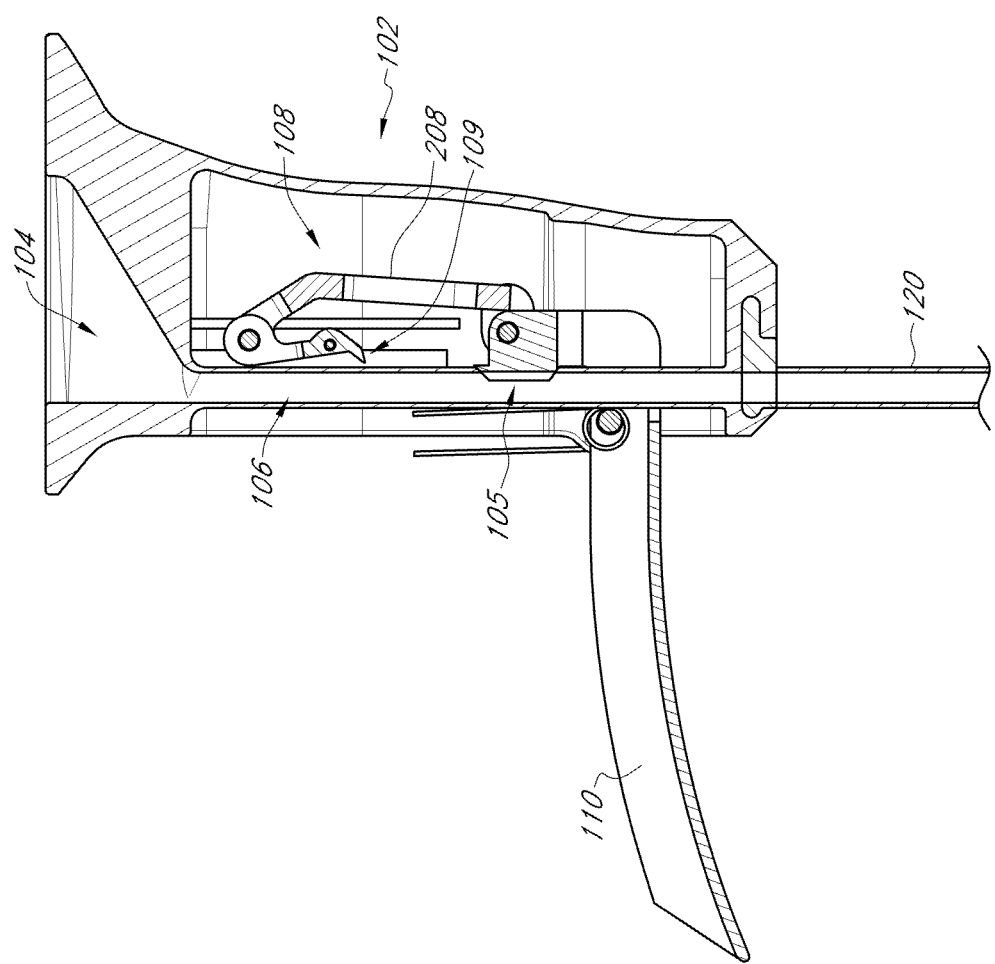
Figure 4B:
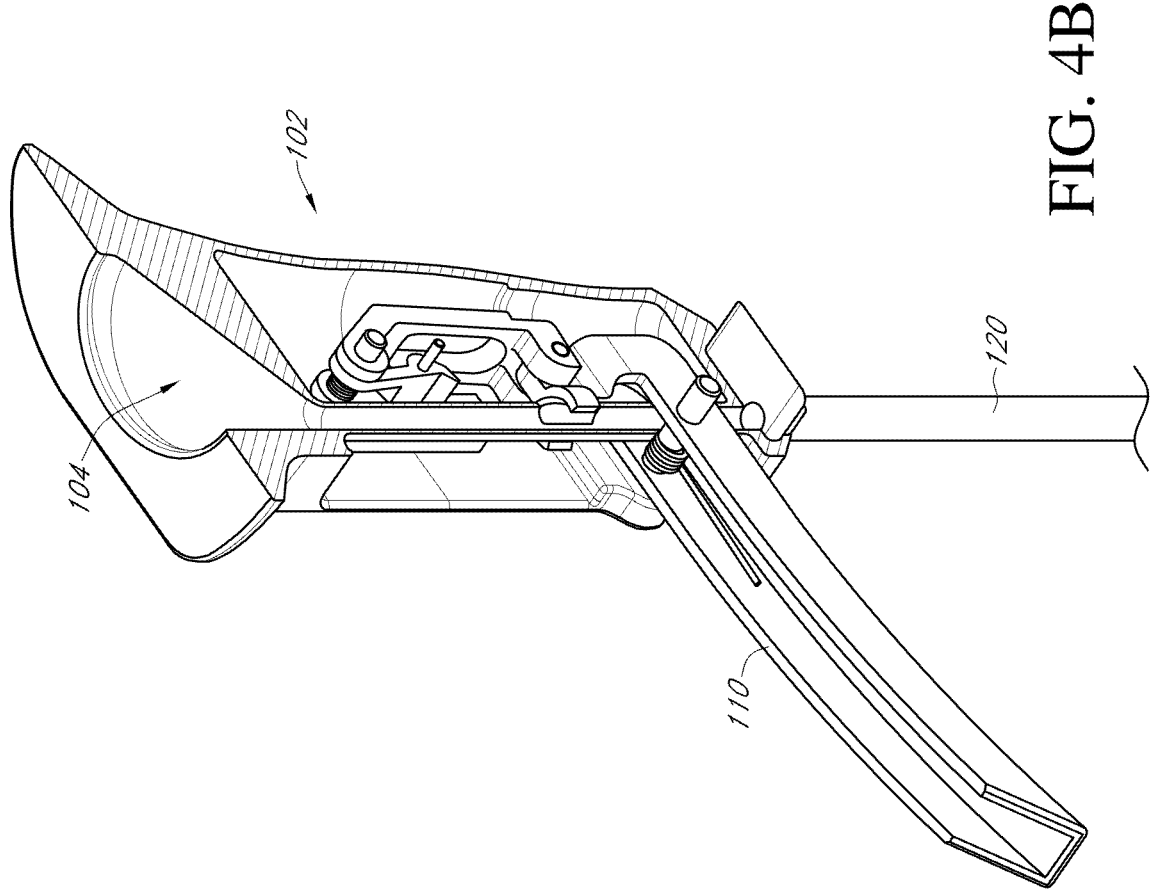
Figure 4C:
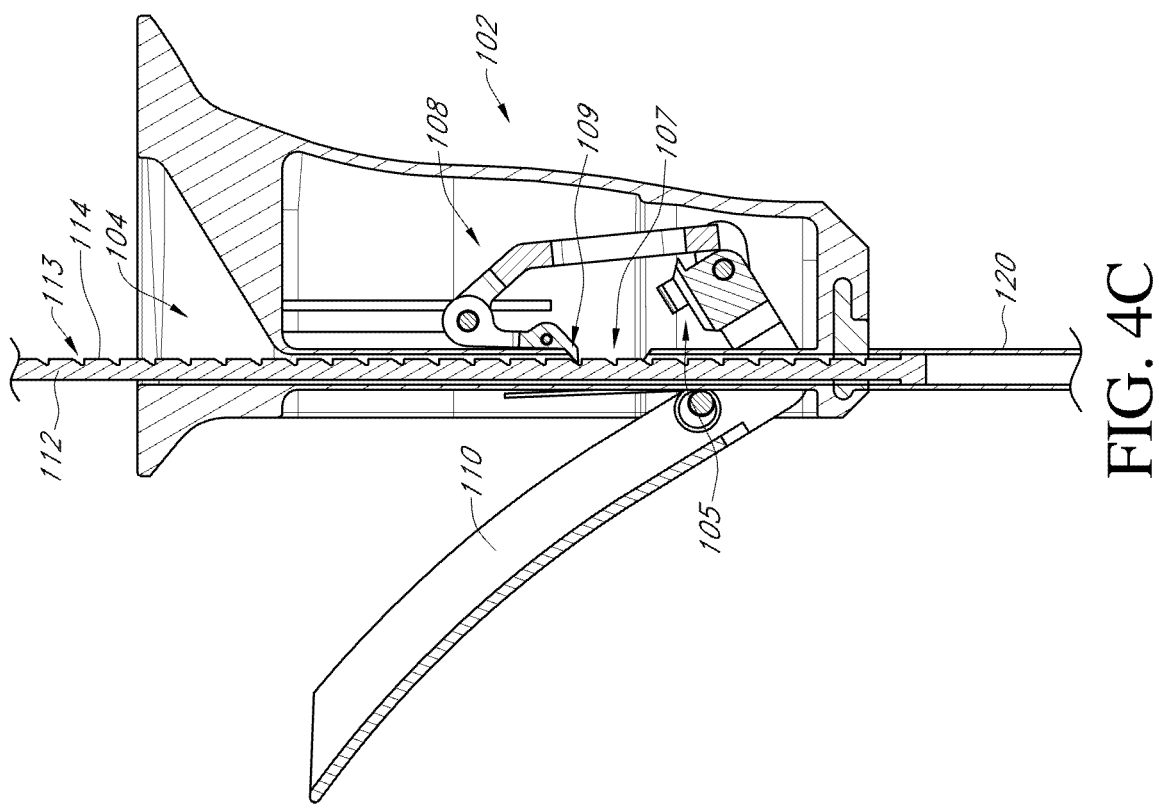
Figure 4D:
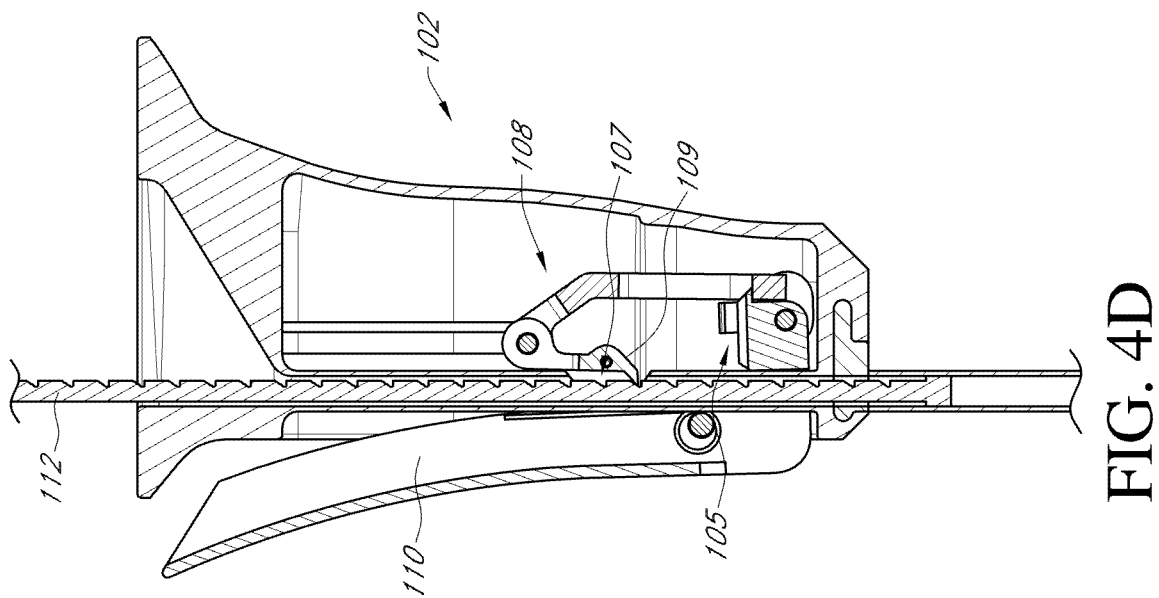
Figure 4F:
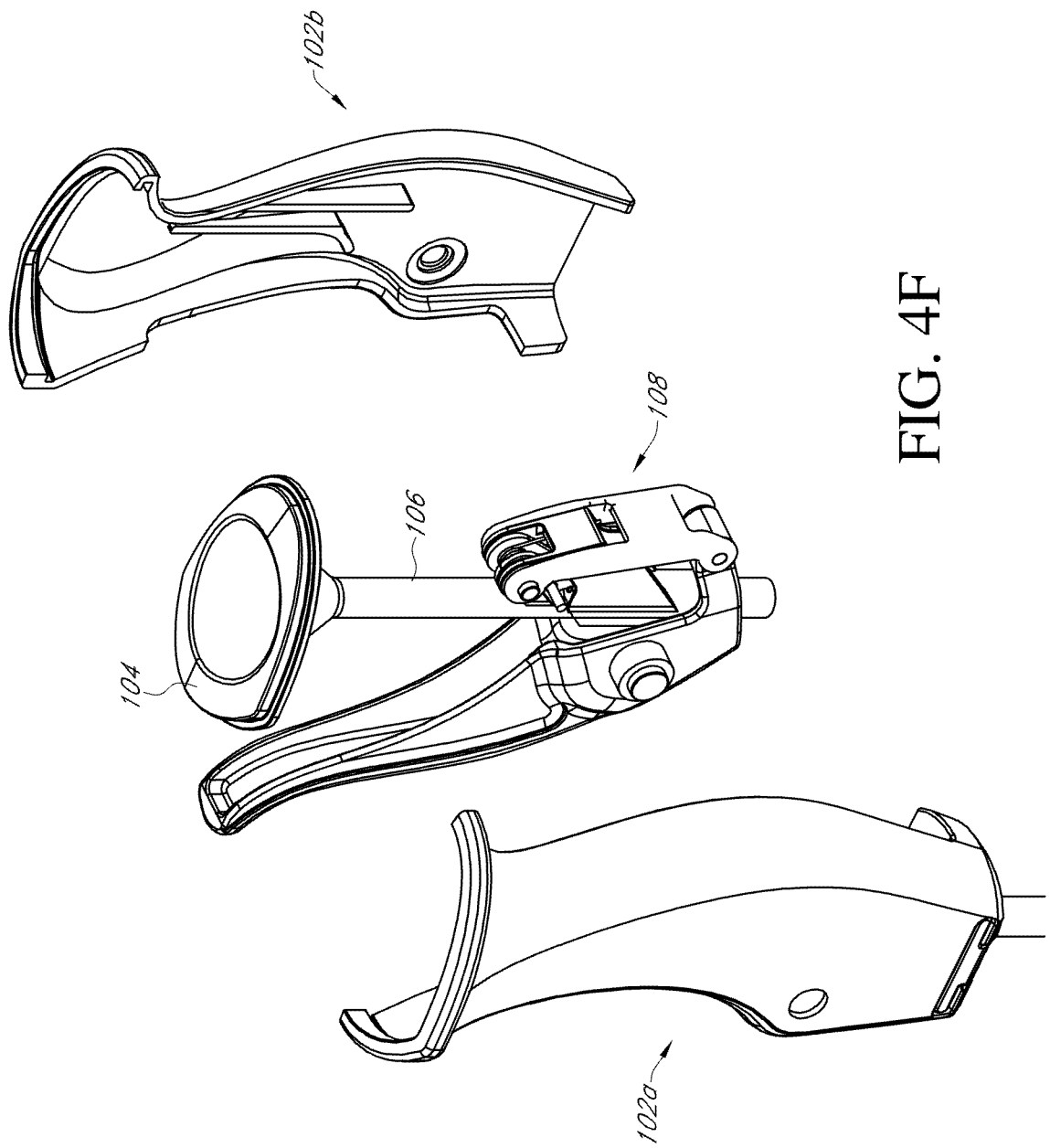
FIGS. 4F and 4G illustrate exploded views of an example embodiment of a bone graft delivery device including a ratcheting mechanism.
Figure 4G:
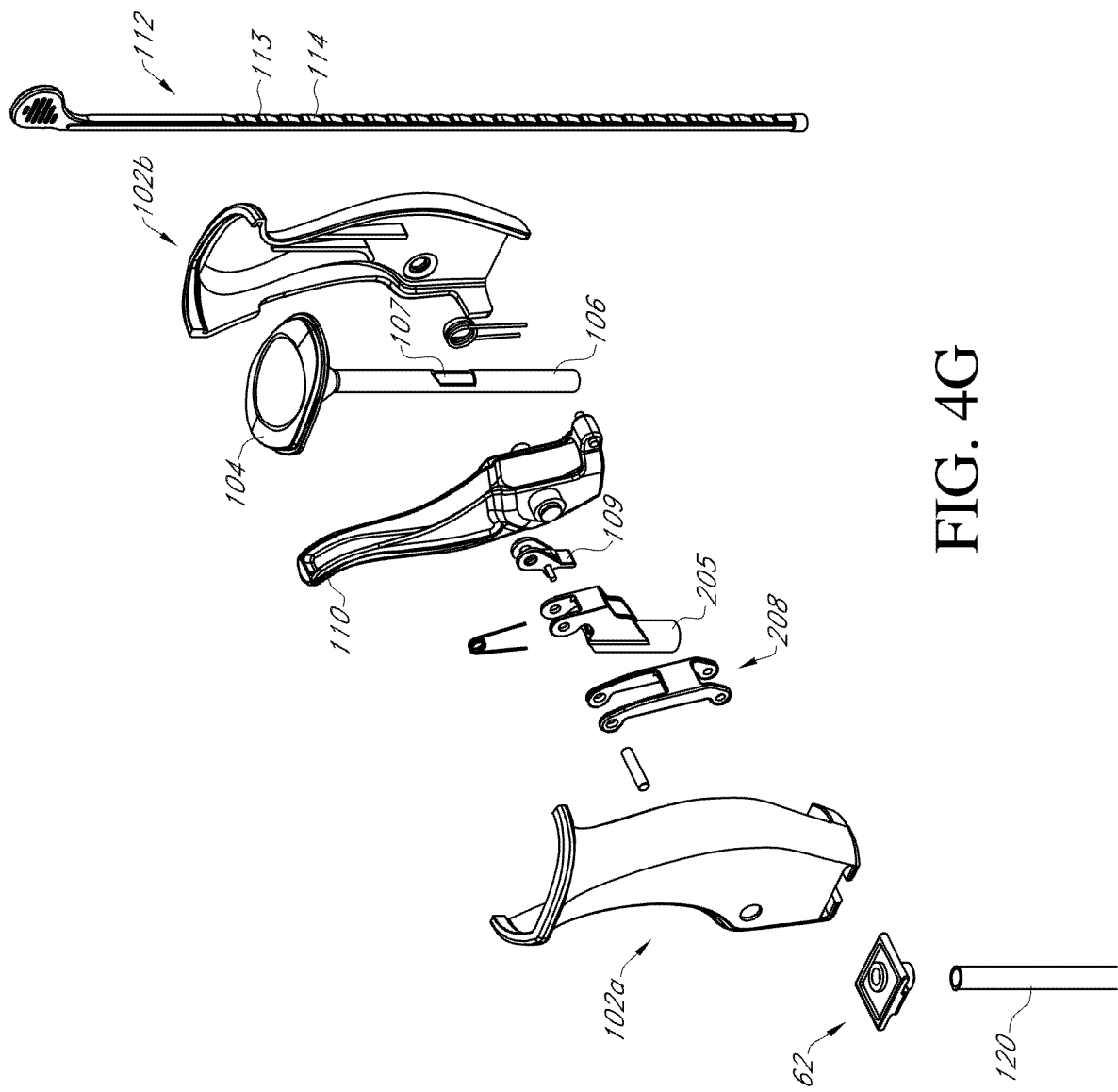

In some embodiments, the handle 102 includes a ratcheting mechanism 108 configured to advance the plunger 112 and bone graft material from the funnel 104 and through the channel 106 and tube 120 for delivery, as shown in FIGS. 4A-4E. The ratcheting mechanism 108 and plunger 112 can advantageously create pressure on the bone graft material in the tube 120 to improve delivery to the target location. In some embodiments, the plunger 112 fully or substantially seals with the inner diameter of the tube 120. This can create a vacuum within the tube 120 and/or can provide greater pressure on the bone graft material to force the bone graft material through the tube 120 and out of the distal end of the tube 120 or distal tip 130. In some embodiments, the plunger 112 or a portion of the plunger 112 is made of, for example, rubber silicone, which can help improve the seal with the tube 120 and/or can help provide pressure on the bone graft material. In some embodiments, the plunger 112 can be made of a plastic or another material and can include an elastomeric rubber stopper 115 at the distal end, for example as shown in FIG. 4O. The stopper 115 can be dual injection molded or co-molded with the plunger 112 so that the stopper 115 cannot normally be removed from the plunger 112. As shown in FIG. 4X, the stopper 115 can be molded onto or over a barb-shaped distal end of the plunger 112. The plunger 112 and ratcheting mechanism 108 can therefore allow the bone graft delivery device to extrude even highly viscous and/or granular bone graft material.

In the illustrated embodiment, the ratcheting mechanism 108 includes a cover 105 and a pawl 109 coupled to the trigger 110 via an arm 208. The funnel shaft 106 includes a window 107 in a portion of the shaft 106 facing the pawl 109. The plunger 112 can be made of a rigid or flexible material. For example, the plunger 112 can be plastic, carbon fiber, metal, or any other suitable material. The plunger 112 includes a series of teeth 114 and notches 113 located between the teeth 114 and configured to receive the pawl 109. The notches 113 can be generally triangular. As shown, distal edges of the teeth 114 slope proximally toward the outer edge of the plunger 112 to allow the pawl 109 to slide along the distal edges in use. In some embodiments, extending the trigger 110 away from the handle 102, for example to a position perpendicular to the handle 102, causes the cover 105 to rest in and close the window 107 of the funnel shaft 106, as illustrated in FIGS. 4A and 4B, to allow for loading of the bone graft material through the funnel 104 into the channel 106. In this position, the pawl 109 rests proximal to the window 107. The plunger 112 can be inserted into the funnel 104 and channel 106 to advance some or all of the bone graft material past the window 107. Once the bone graft material has been loaded, the trigger 110 can be moved toward the handle 102 to an intermediate position, as shown in FIG. 4C. This moves the pawl 109 distally so that the pawl 109 engages one of the notches 113 on the plunger 112 through the window 107. Movement of the trigger 110 to a final position closest the handle 102 causes the pawl 109 to move distally within the window 107 (or away from the funnel 104 and toward the tube 120), thereby advancing the plunger 112 distally within the channel 106 to force the bone graft material distally within the channel 106 and/or tube 120, as shown in FIGS. 4D and 4E. The trigger 110 can be moved back to the intermediate position to cause the pawl 109 to slide proximally along the plunger 112 and over one of the teeth 114 to engage a more proximal notch 113. The trigger 110 can be moved between the intermediate position and final position multiple times until the pawl 109 has reached the proximal end of the plunger 112. The user can re-load the device 100 as needed during a procedure. The ratcheting mechanism 108 and trigger 110 in combination can advantageously provide a mechanical advantage and allow the user to apply a greater force in operating the bone graft delivery device 100 and/or delivering the bone graft material compared to, for example, a standard syringe used to deliver bone graft material.

Figure 4H:
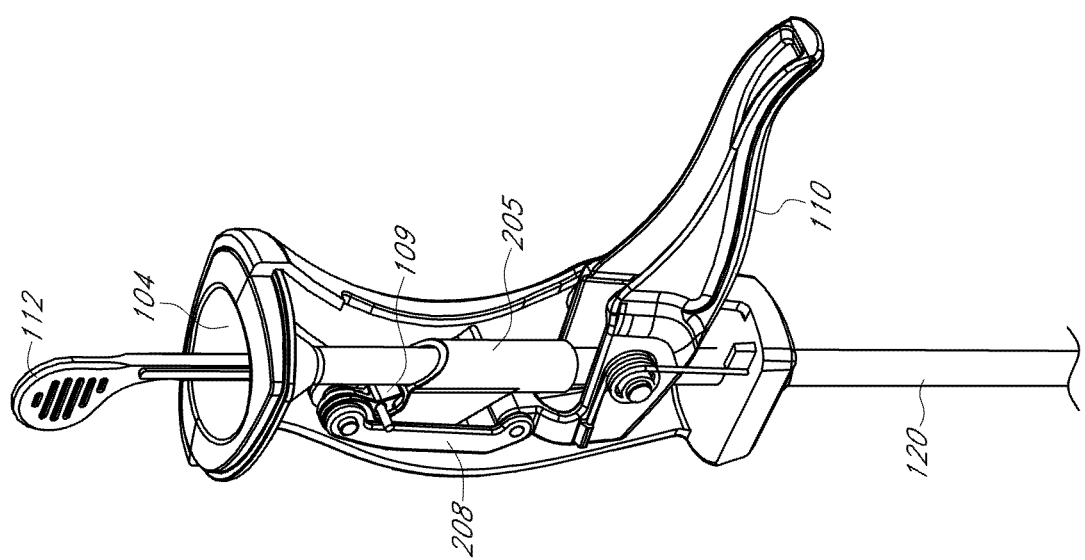
FIGS. 4H-4M illustrate operation of the ratcheting mechanism of the device of FIGS. 4F and 4G.
Figure 4I:
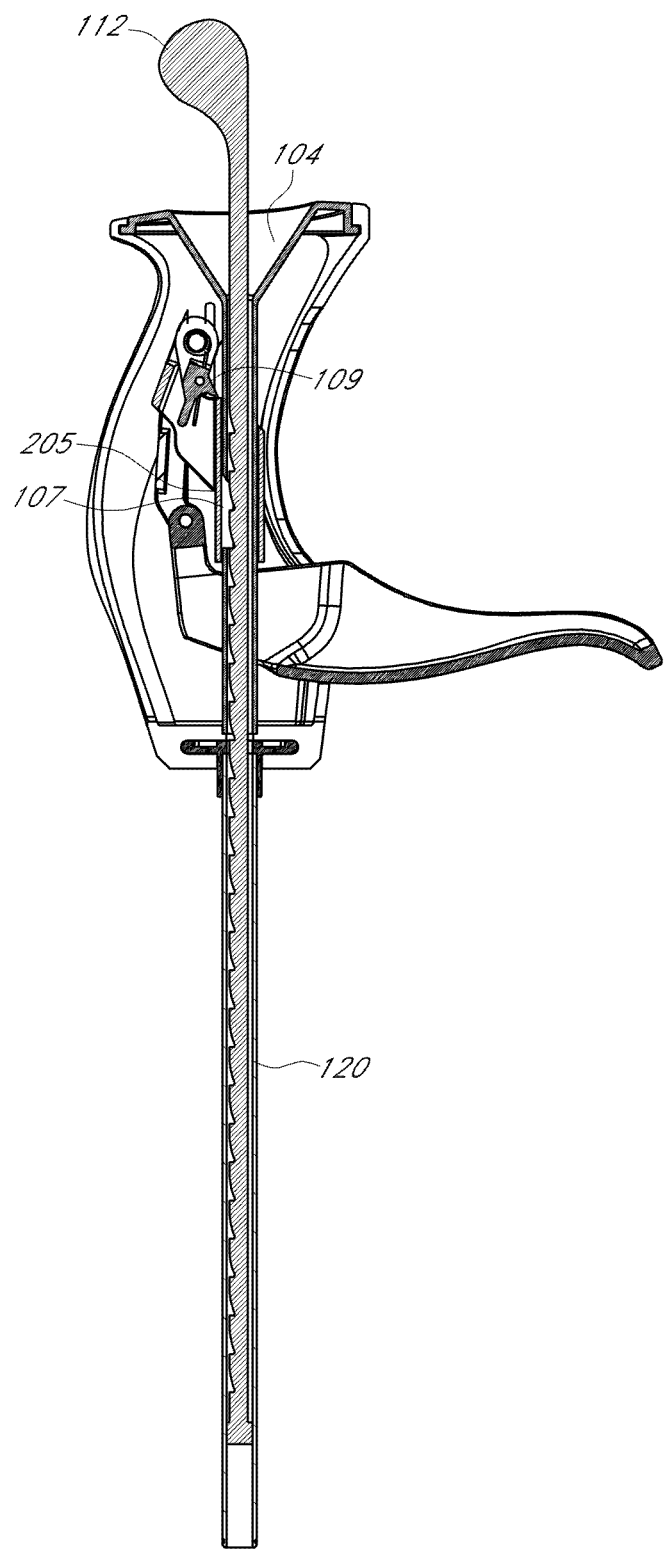
Figure 4J:
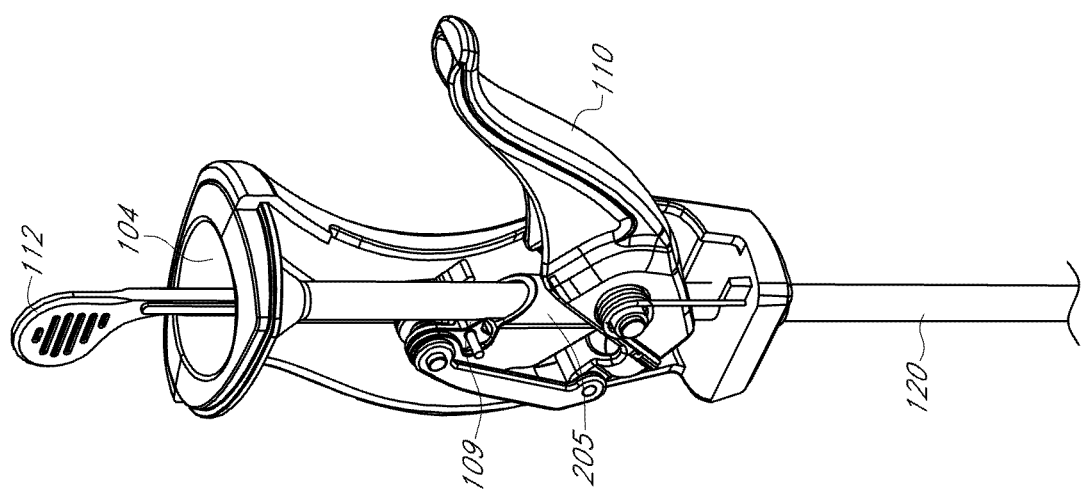
Figure 4K:
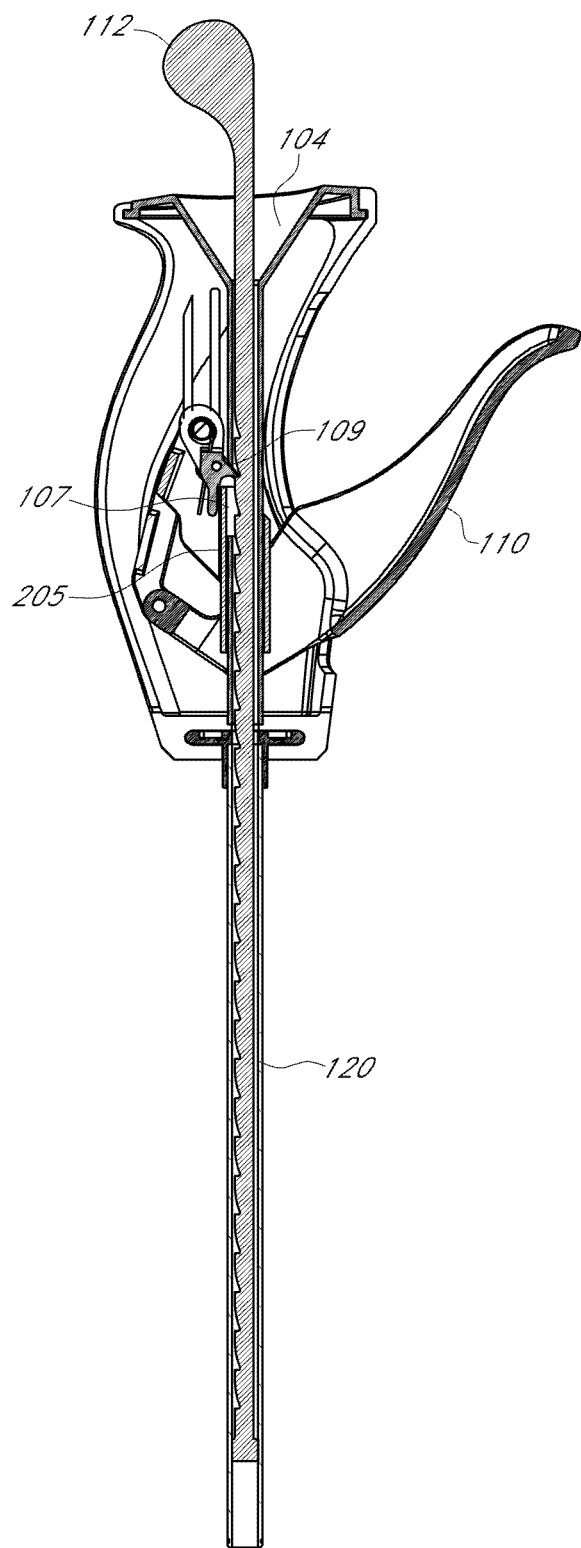
Figure 4L:
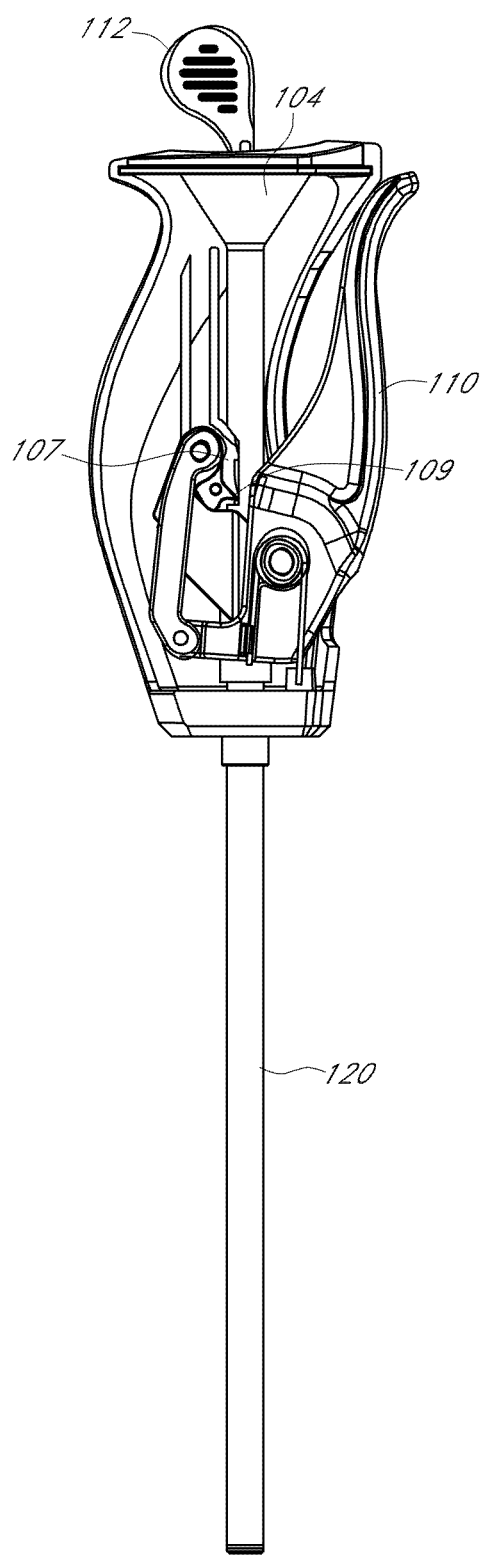
Figure 4M:
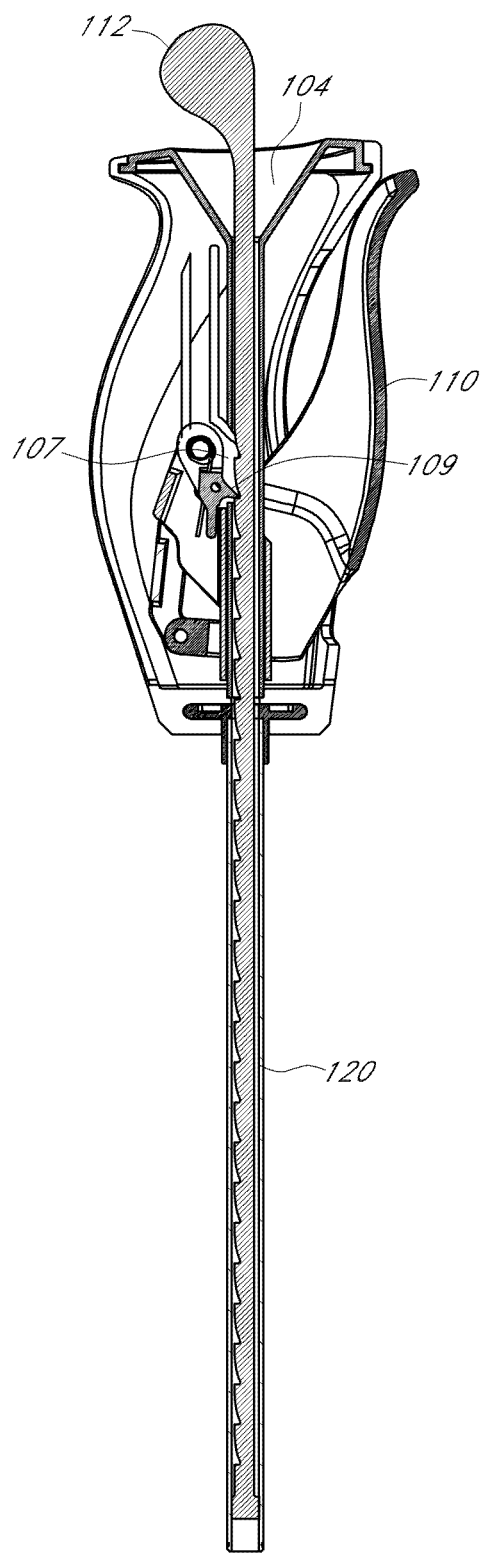
Figure 4N:
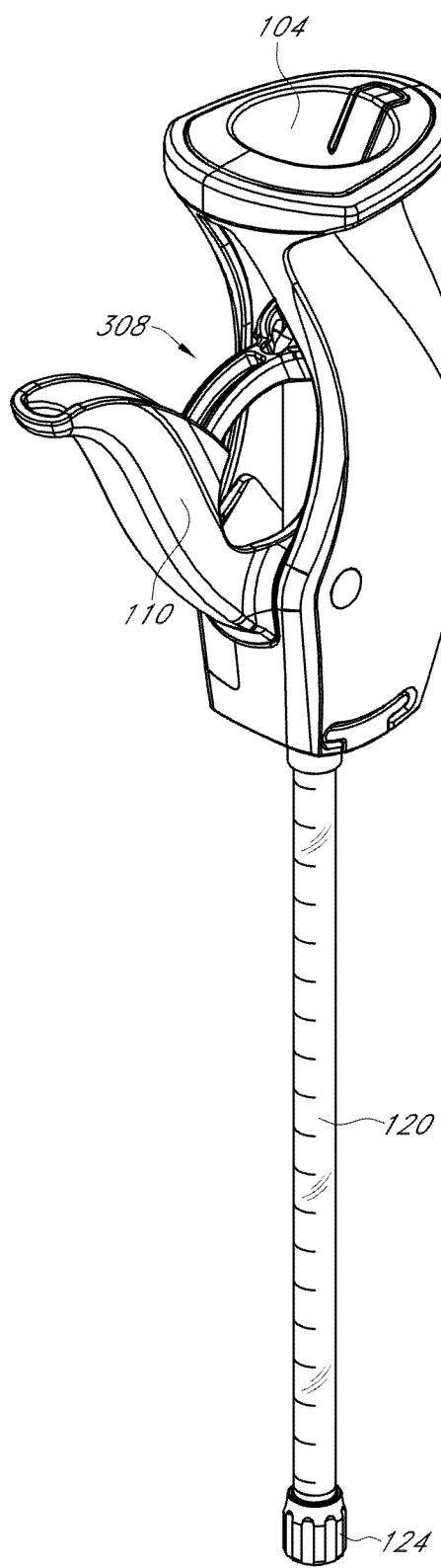
FIG. 4N illustrates a perspective view of an example embodiment of a bone graft delivery device including a ratcheting mechanism.
Figure 40:
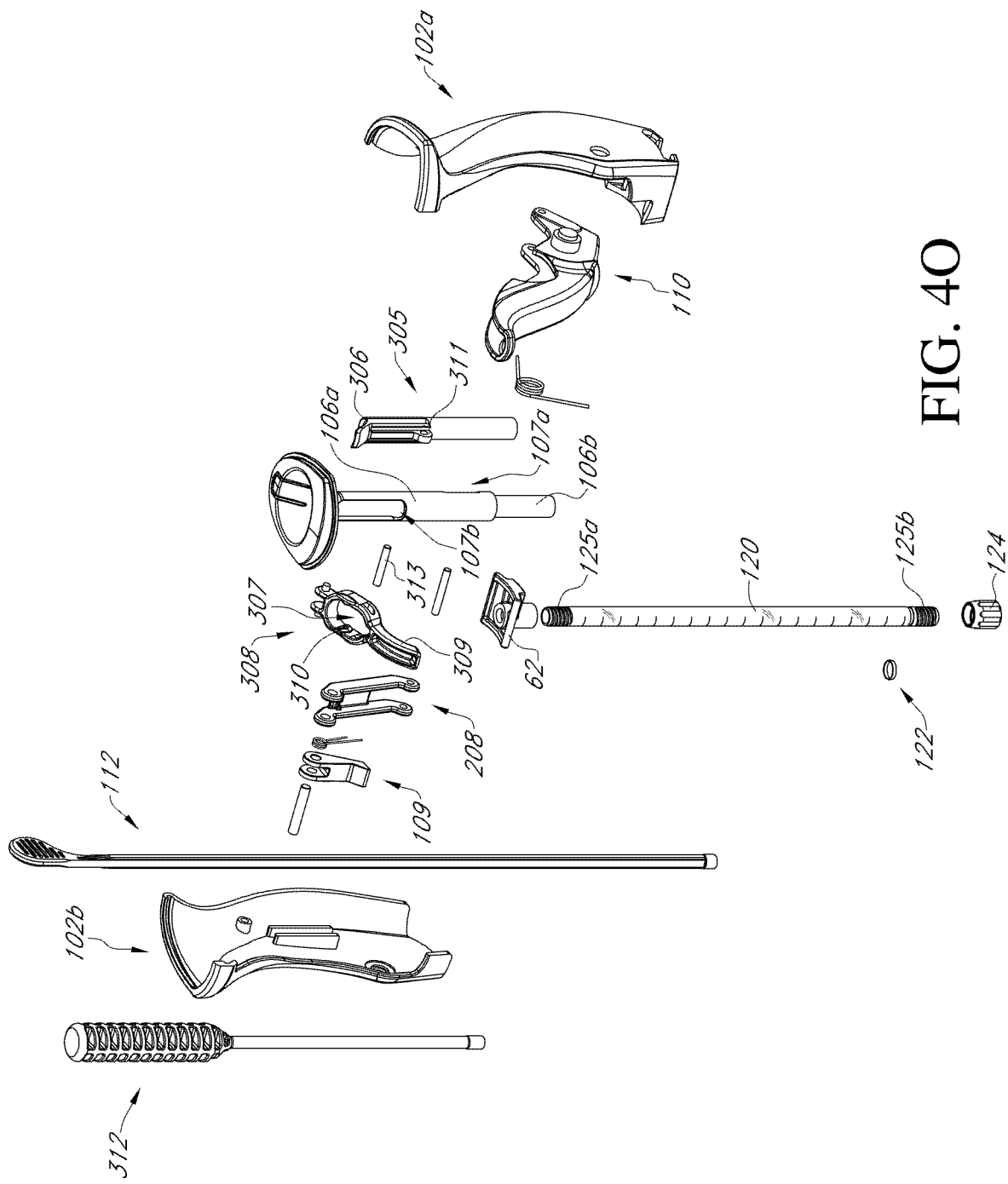

Another example embodiment of a handle 102 and ratcheting mechanism 108 is shown in FIGS. 4F-4M. In this embodiment, the handle 102 includes a two-part clamshell housing 102a, 102b that houses the funnel 104, funnel shaft 106, and ratcheting mechanism 108 assembly as shown in the exploded views of FIGS. 4F and 4G. The ratcheting mechanism 108 includes the pawl 109 and a sheath 205 coupled to the trigger 110 via arm 208. The plunger 112 includes a series of sloped teeth 114 alternating with notches 113 that are configured to receive the pawl 109. When the trigger 110 is in the first position, as shown in FIGS. 4H and 4I, the sheath 205 covers the pawl window 107 and the pawl 109 rests proximal to the window 107. Movement of the trigger 110 to the intermediate position causes the sheath 205 and pawl 109 to move distally, exposing the window 107 and allowing the pawl 109 to engage the plunger 112, as shown in FIGS. 4J and 4K. Movement of the trigger 110 to the final position causes the pawl 109 to move distally, advancing the plunger 112 distally, as shown in FIGS. 4L and 4M.

Yet another example embodiment of a handle 102 and ratcheting mechanism 108 is shown in FIGS. 4N-4T. In this embodiment, the funnel shaft 106 includes an upper shaft portion 106a and a lower shaft portion 106b, and the lower shaft portion 106b has an outer diameter smaller than an outer diameter of the upper shaft portion 106a. As shown in FIGS. 4P-4T, the outer diameter of the lower shaft portion 106b can be approximately the same as an inner diameter of the upper shaft portion 106a, and the shaft 106 can include a step 206 (shown in FIG. 4R) at a transition point between the upper shaft portion 106a and lower shaft portion 106b. In the illustrated embodiment, the upper 106a and lower 106b shaft portions are integrally formed. In other embodiments, the upper 106a and lower 106b shaft portions can be separate pieces, and a proximal end of the lower shaft portion 106b can be coupled to an inner perimeter of a distal end of the upper shaft portion 106a. The upper shaft portion 106a includes a first window 107a for the pawl 109 and a second window 107b on an opposite side of the upper shaft portion 106a from the first window 107a. A sheath 305 is disposed within or inside the upper shaft portion 106a, and in the illustrated embodiment, a lever 308 extends from the trigger 110 and engages the sheath 305 through the second window 107b, as shown in FIGS. 4P-4T.

Figure 4P:
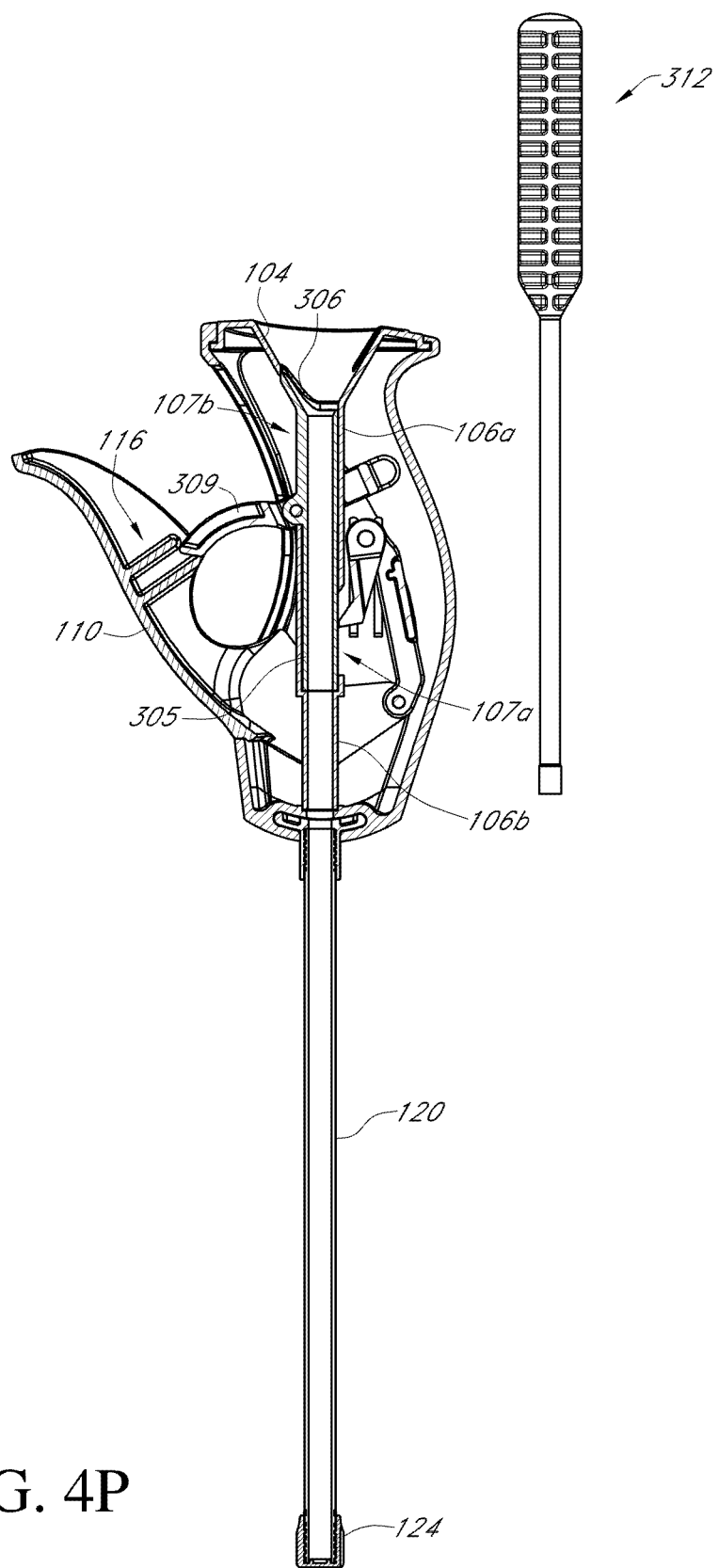
FIGS. 4P-4T are section views illustrating operation of the ratcheting mechanism of the device of FIGS. 4N and 4O.
Figure 4Q:
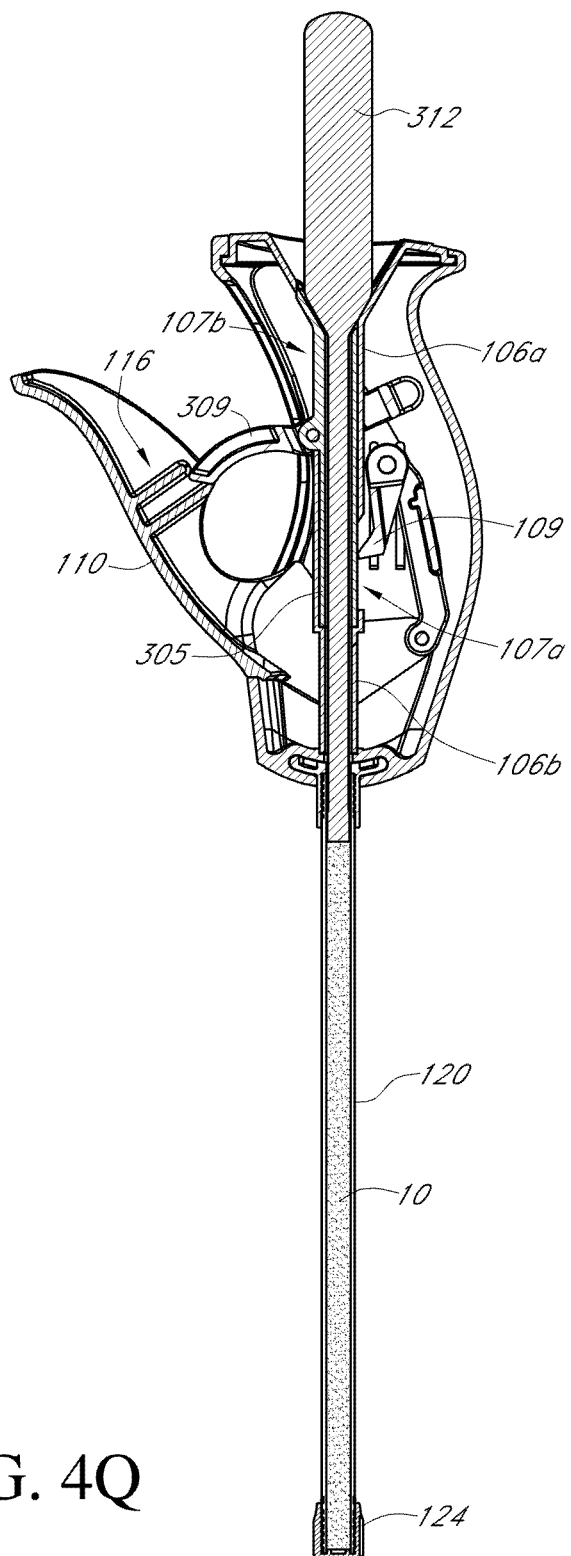

In some embodiments, the lever 308 is integrally formed with the sheath 305. Alternatively, the lever 308 can be coupled to the sheath 305, for example, with a pin 313. In some embodiments, the lever 308 includes a body 310 having a generally circular or ovular aperture 307, and an arm 309 extending from one end of the body 310. The aperture 307 receives the funnel shaft 106 so that the body 310 surrounds the upper shaft portion 106a. The sheath 305 includes a protrusion 311 that can extend through or over the second window 107b when the sheath 305 is disposed in the upper shaft portion 106a. The protrusion 311 is aligned with the lever body 310 with the protrusion 311 disposed in the aperture 307. The pin 313 extends through holes in the body 310 and protrusion 311 to couple the sheath 305 to the lever 308. In some embodiments, the pin 313 is secured to the protrusion 311 and lever body 310 with a weld, glue, or other appropriate means. The free end of the arm 309 of the lever 308 releasably engages the trigger 110. For example, the trigger 110 can include a track 116 configured to releasably receive the arm 309 as shown in FIGS. 4P and 4Q, and the arm 309 can engage the track 116 via, for example, a snap fit. In some embodiments, the trigger 110 is biased or naturally rests at a distance from the handle body that holds the arm 309 in the track 116. The trigger 110 can be flexed or allowed to move slightly away from the handle body to release the arm 309.

In some embodiments, the sheath 305 has an outer diameter about the same and slightly less than the inner diameter of the upper shaft portion 106a and a thickness about the same as a thickness of the lower shaft portion 106b. The sheath 305 can include an upper lip 306, and a length of the sheath 305 can be selected such that in an initial loading position, shown in FIG. 4P, the lip 306 rests against an inner surface of the funnel 104 and a distal end of the sheath 305 rests against the step 206. In the loading position, the sheath 305 covers the first window 107a. The dimensions of the upper shaft portion 106a, lower shaft portion 106b, and sheath 305 advantageously allow the sheath 305 to be substantially flush with an inner surface of the upper shaft portion 106a and step 206 and provide a substantially smooth and constant-diameter inner passageway from the sheath 305 to the lower shaft portion 106b. The bone graft delivery device of FIGS. 4N-4T also includes a pusher rod 312 and a tube end cap 124.

Figure 4R:
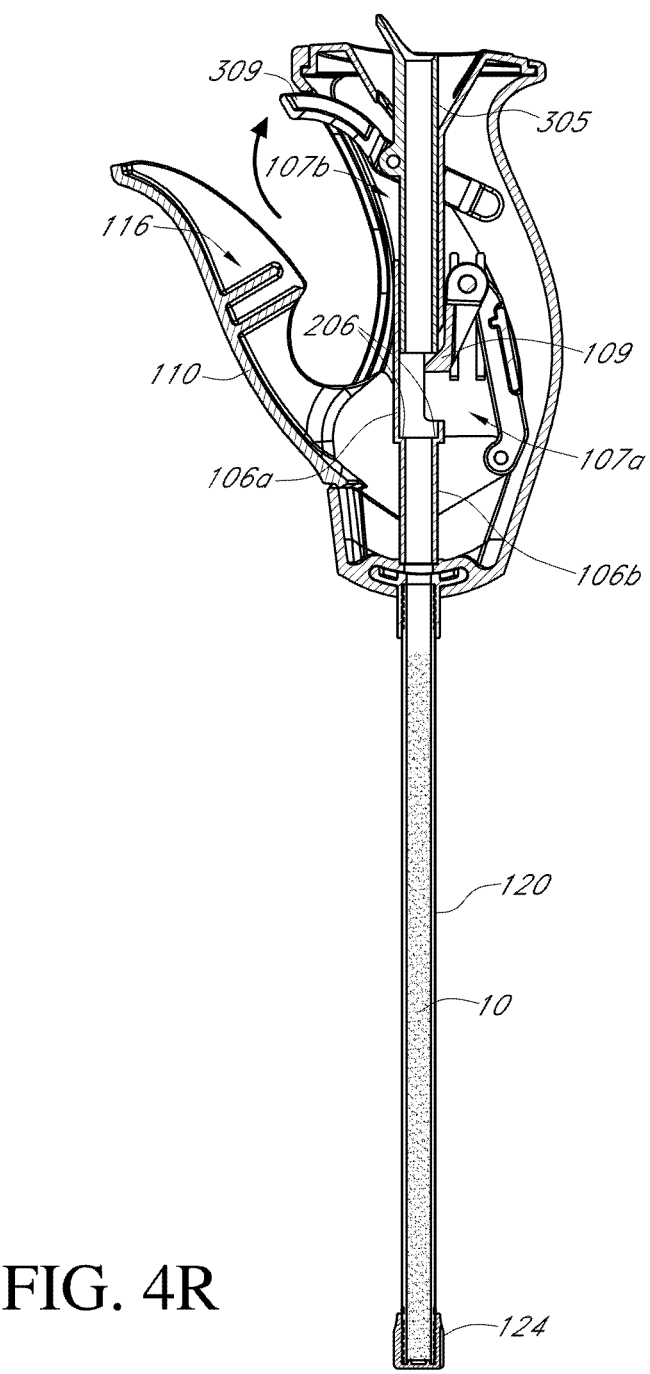
Figure 4S:
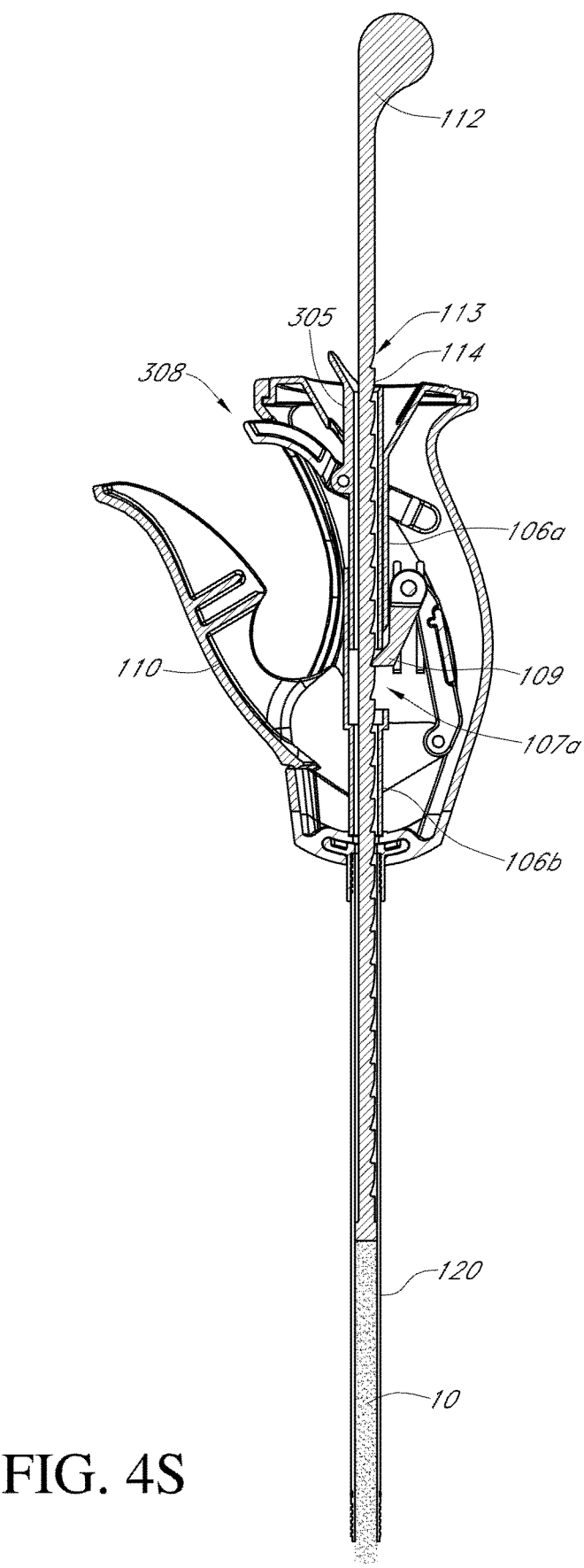
Figure 4T:
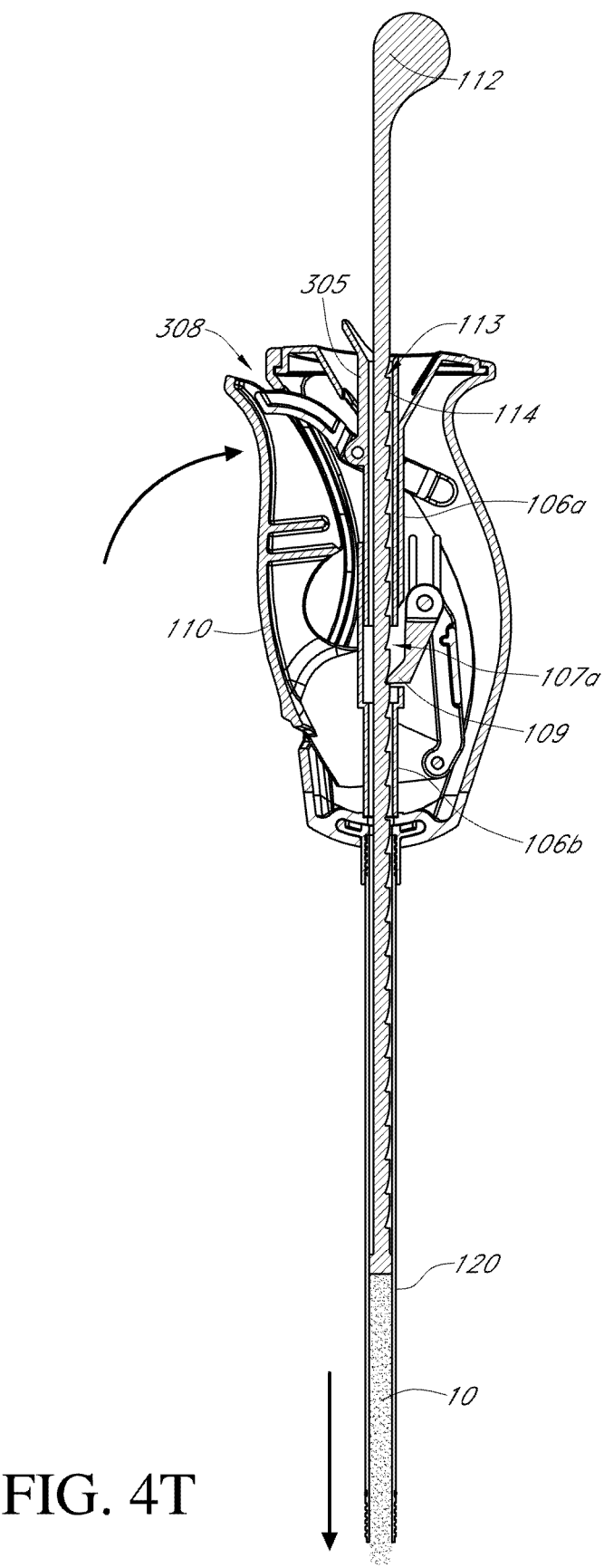
Figure 4U:
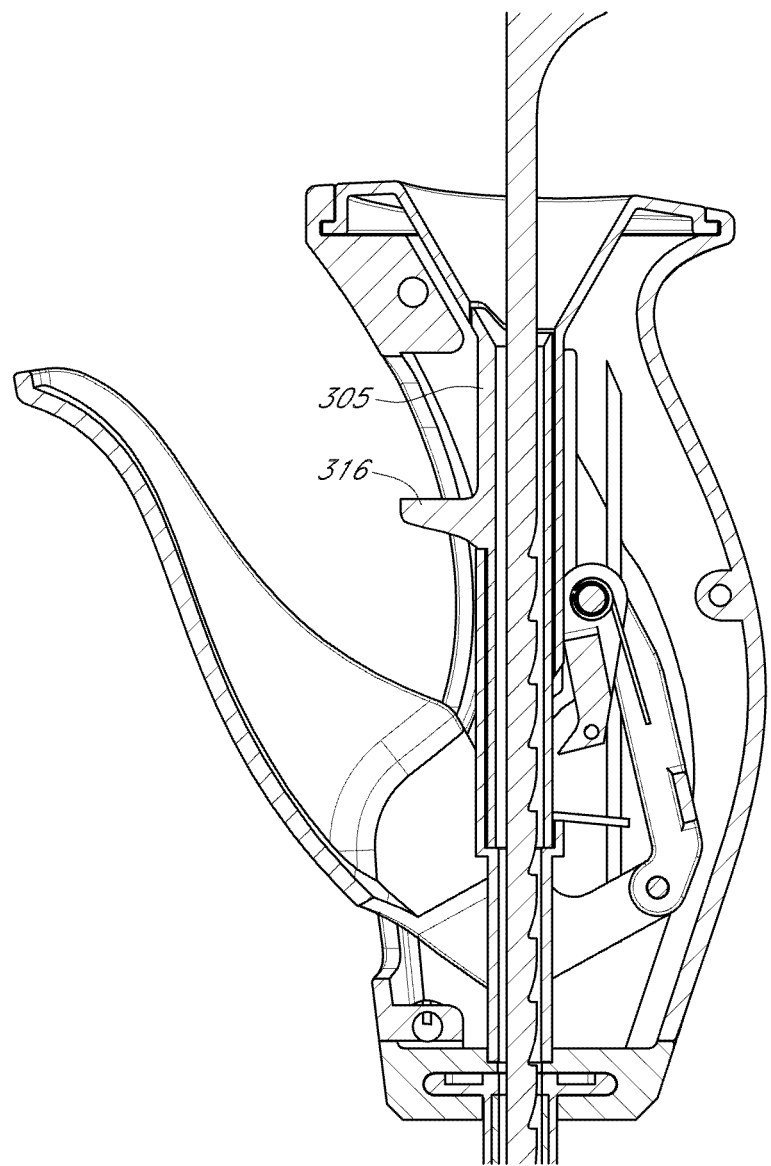
FIGS. 4U and 4V illustrate section views of an example embodiment of a handle of a bone graft delivery device including a ratcheting mechanism.
Figure 4V:
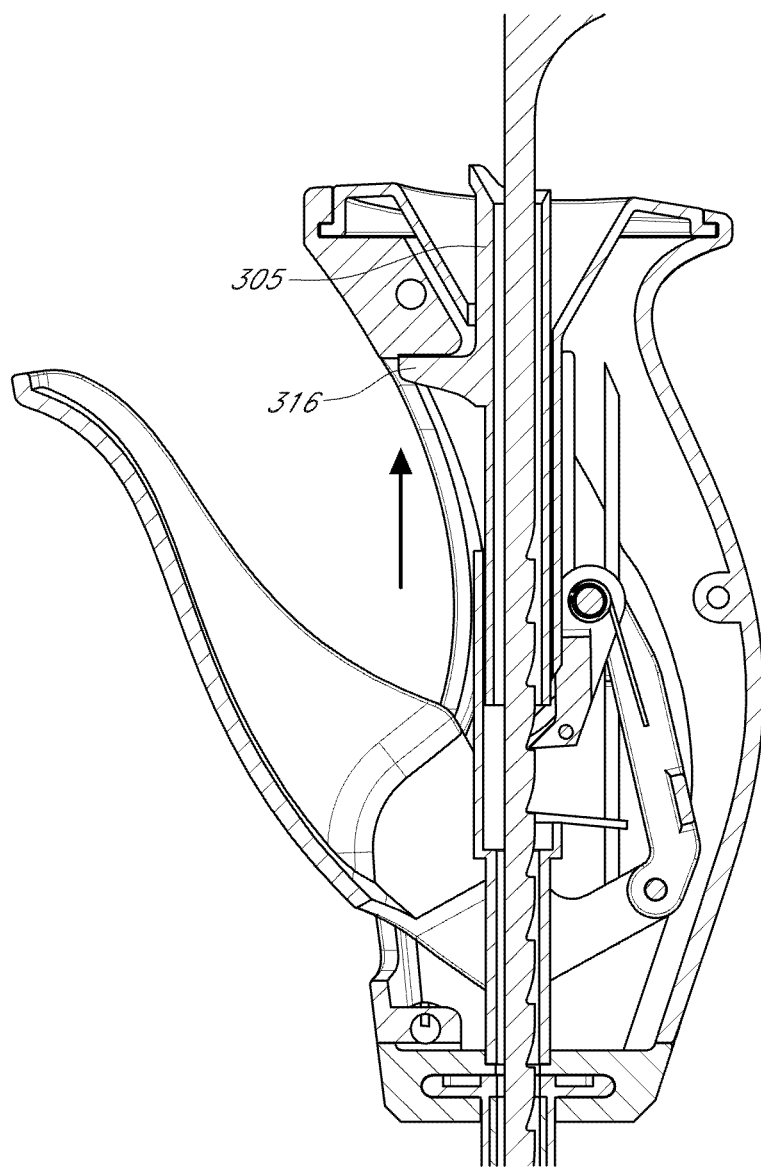
Figure 4X:
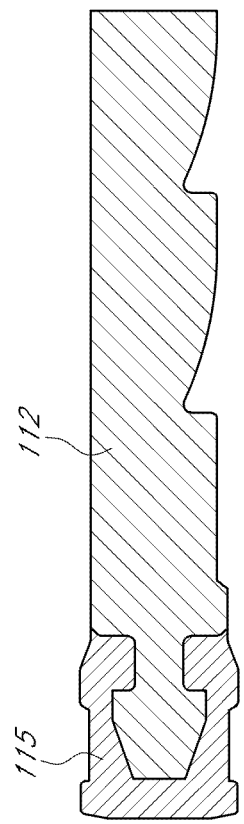
FIG. 4X illustrates a section view of a distal end of a plunger of a bone graft delivery device.

To load bone graft material, the lever 308 is coupled to the trigger 110 so that the sheath 305 sits in the initial loading position shown in FIG. 4P. Bone graft material 10 is loaded into the funnel 104, and the pusher rod 312 can be inserted into the funnel 104 to help urge the bone graft material 10 through the sheath 305 and lower shaft portion 106b and into the tube 120 as shown in FIG. 4Q. In some embodiments, the pusher rod 312 is made of, for example, a glass filled or rigid polymer material. The tube end cap 124 inhibits or prevents the bone graft material 10 from exiting the distal end of the tube 120 during the loading process and until the user wishes to deliver the bone graft material 10. The tube end cap 124 can be attached to the distal end of the tube 120 via a threaded coupling, friction fit, or other suitable means. In the illustrated embodiment, the tube 120 includes external threads 125b at or near the distal end configured to mate with internal threads in the tube end cap 124. Once the bone graft material 10 is loaded, the pusher rod 312 is removed, and the lever 308 is released from the trigger 110 as shown in FIG. 4R. As shown, release of the lever 308 causes or allows the lever to move toward the funnel, thereby also moving the sheath 305 proximally to expose the first window 107a and allow the pawl 109 to enter the shaft 106 through the first window 107a. The plunger 112 can be inserted before or after releasing the lever 308 and extends through the sheath 305, upper shaft portion 106a, and lower shaft portion 106b and into the tube 120 as shown in FIG. 4S. When the plunger 112 is inserted and the lever 308 is released so that the first window 107a is exposed, the pawl 109 engages one of the notches 113 on the plunger 112. The lever 308 can advantageously provide the user with a greater mechanical advantage and/or greater control in moving the sheath 305 proximally to expose the first window 107a. In other embodiments, the sheath includes a protrusion 316 without a lever as shown in FIGS. 4U and 4V. The user can use the protrusion 316 to lift or lower the sheath 305.

The tube end cap 124 is removed when the user wishes to deliver the bone graft material 10 through the tube 120. Movement of the trigger 110 toward the handle causes the pawl 109 to move distally, advancing the plunger 112 distally, as shown in FIG. 4T. The trigger 110 is moved away from and toward the handle to advance the plunger 112 and bone graft material 10 through the tube 120 in discreet increments. Of course, other ratcheting mechanisms and/or other mechanisms for advancing bone graft material through the handle 102 and/or tube 120 are also possible.

In some embodiments, the funnel 104 or other opening for loading of bone graft material can be positioned in the handle 102 in locations other than a proximal end or base of the handle 102. For example, in the example embodiment of FIGS. 2C-2E, the handle 102 is configured such that the trigger 110 and a grip 111 extend from a main body portion 103 of the handle 102. As shown, the funnel 104 is located on an opposite side of the body portion 103 from the grip 111 and trigger 110. A main channel 406 extends through the handle 102 from an opening in a proximal end of the body portion 103 to an opening in a distal end of the body portion 103 and is in fluid communication with the tube 120. The funnel shaft 106 extends from the funnel 104 to intersect the main channel 406 as shown in FIGS. 2D and 2E. In the illustrated embodiment, the funnel 104 and funnel shaft 106 are oriented at an angle 1 relative to the main channel 406. The angle can advantageously help direct bone graft material inserted into the funnel 104 and funnel shaft 106 distally toward the tube 120. The bone graft delivery device can include a pusher rod 312 as shown in FIG. 2E to help urge bone graft material from the funnel 104 through the funnel shaft 106 and into the main channel 406. In some embodiments, the pusher rod 312 can be configured such that when fully inserted into the funnel 104 and funnel shaft 106, a distal end 314 of the pusher rod 312 rests at the intersection of the funnel shaft 106 with the main channel 406 to at least partially or substantially close the main channel 406. The distal end 314 of the pusher rod 312 can be formed at an angle with the angle corresponding to the angle of the funnel shaft 106 so that the distal end 314 is continuous with a wall of the main channel 406 when inserted into the funnel shaft 106. In such embodiments, the pusher rod 312 can be configured to remain in place during delivery of bone graft material.

Figure 2C:
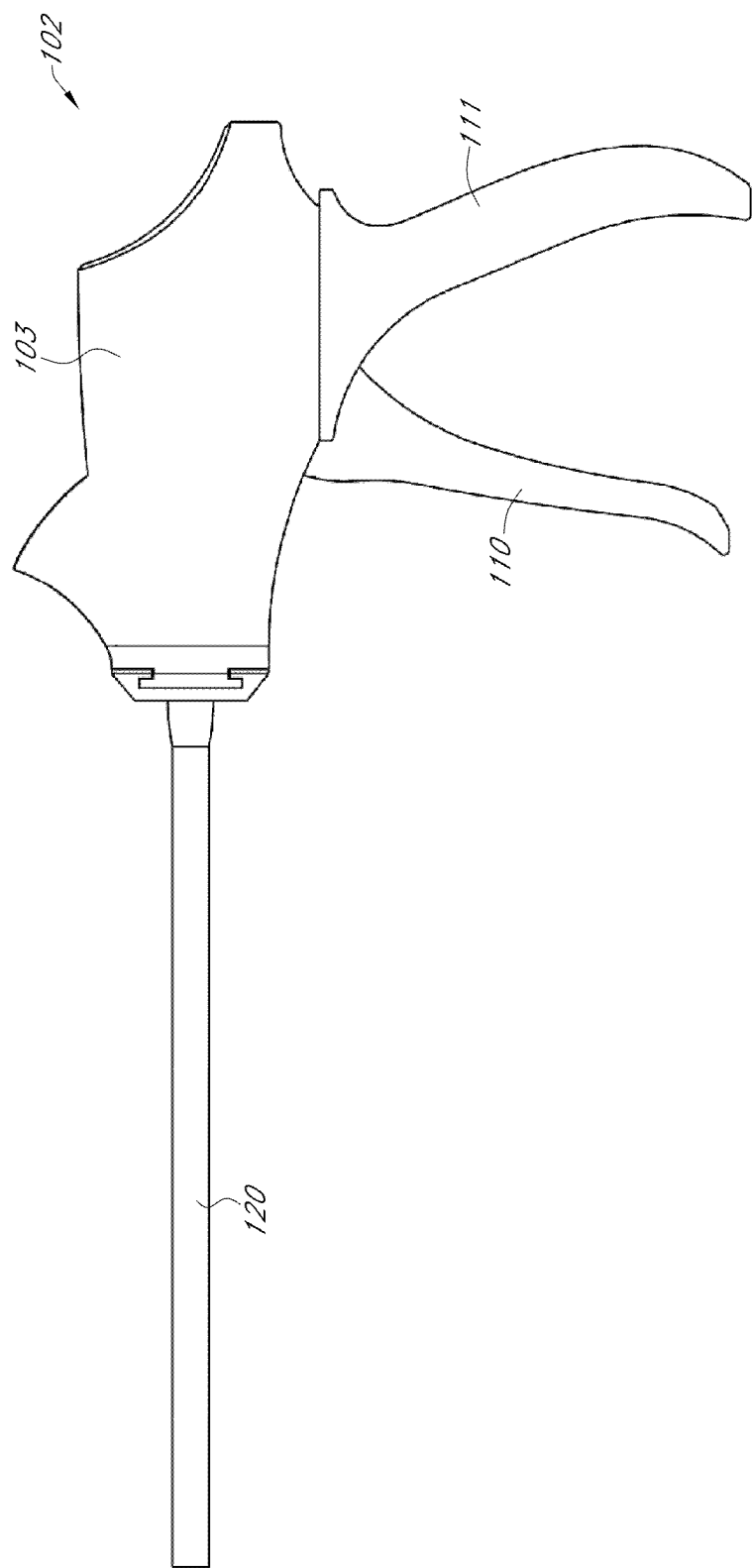
FIG. 2C illustrates a side view of another example embodiment of a bone graft delivery device.
Figure 2D:
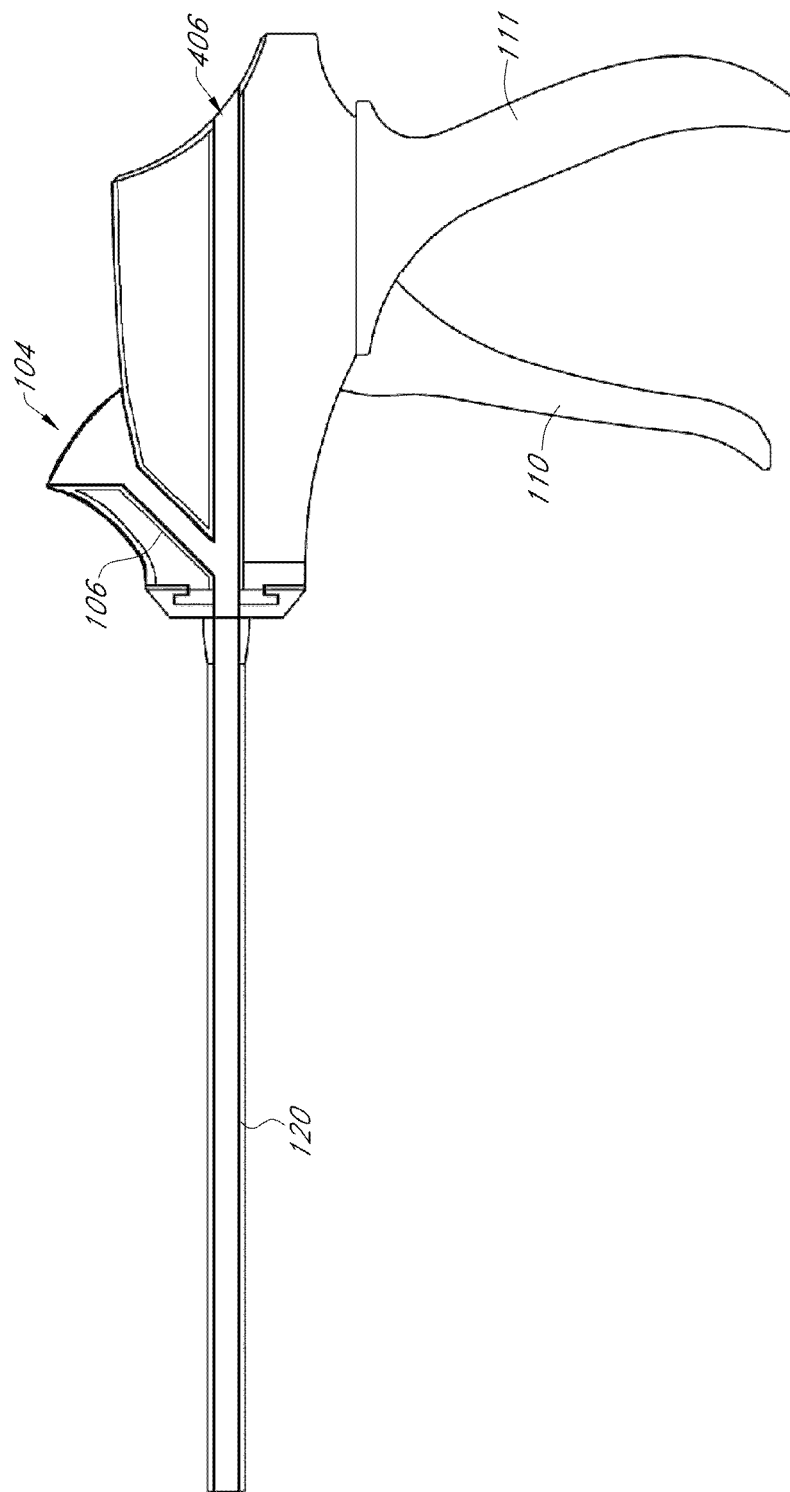
FIG. 2D illustrates a section view of the bone graft delivery device of FIG. 2C.
Figure 2E:
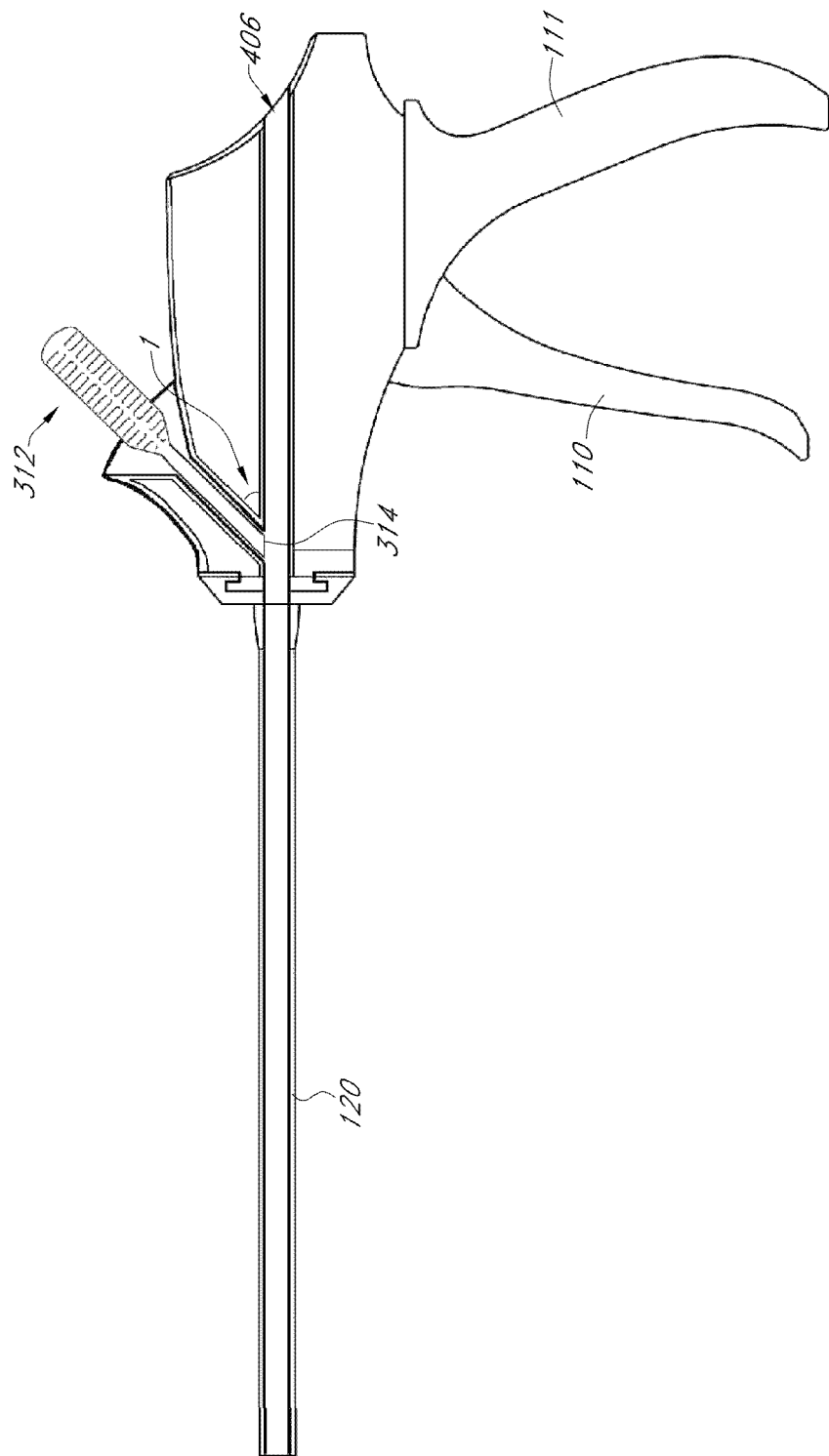
FIG. 2E illustrates a section view of the bone graft delivery device of FIGS. 2C and 2D including a pusher rod.
Figure 3:
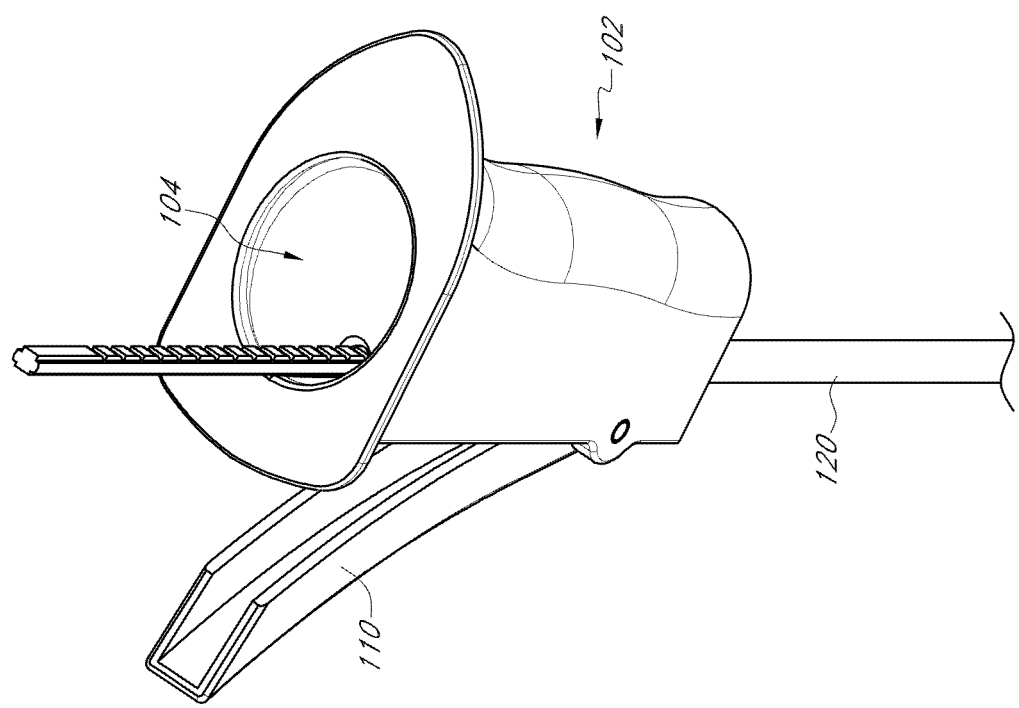
FIG. 3 illustrates a perspective view of a handle of a bone graft delivery device including a funnel for introduction of bone graft.

The handle 102 of FIGS. 2C-2E can include any of the ratcheting mechanisms described herein or any other suitable ratcheting mechanism. In use, once the bone graft material is loaded via the funnel 104, the plunger 112 is inserted from the proximal opening of the main channel 406 through the handle 102 and into the tube 120. The main channel 406 can include a window to allow the pawl to engage notches on the plunger. In use, movement of the trigger 110 toward the grip 111 can cause the pawl to advance the plunger and bone graft material distally in the tube 120. Releasing the trigger 110 to allow the trigger 110 to move away from the grip 111 causes the pawl to slide proximally along the plunger to engage a more proximal notch. If the window is located proximal to the intersection of the funnel shaft 106 with the main channel 406, the cover, sheath, or the like can be omitted from the ratcheting mechanism. In such embodiments, the bone graft material does not pass through the portion of the main channel 406 having the window, so the window can be left uncovered during loading. In some embodiments, the handle 102 of FIGS. 2C-2E does not include a ratcheting mechanism, and a plunger can be inserted into and advanced through the main channel 406 and tube 120 to advance and deliver the bone graft material.

Figure 2F:
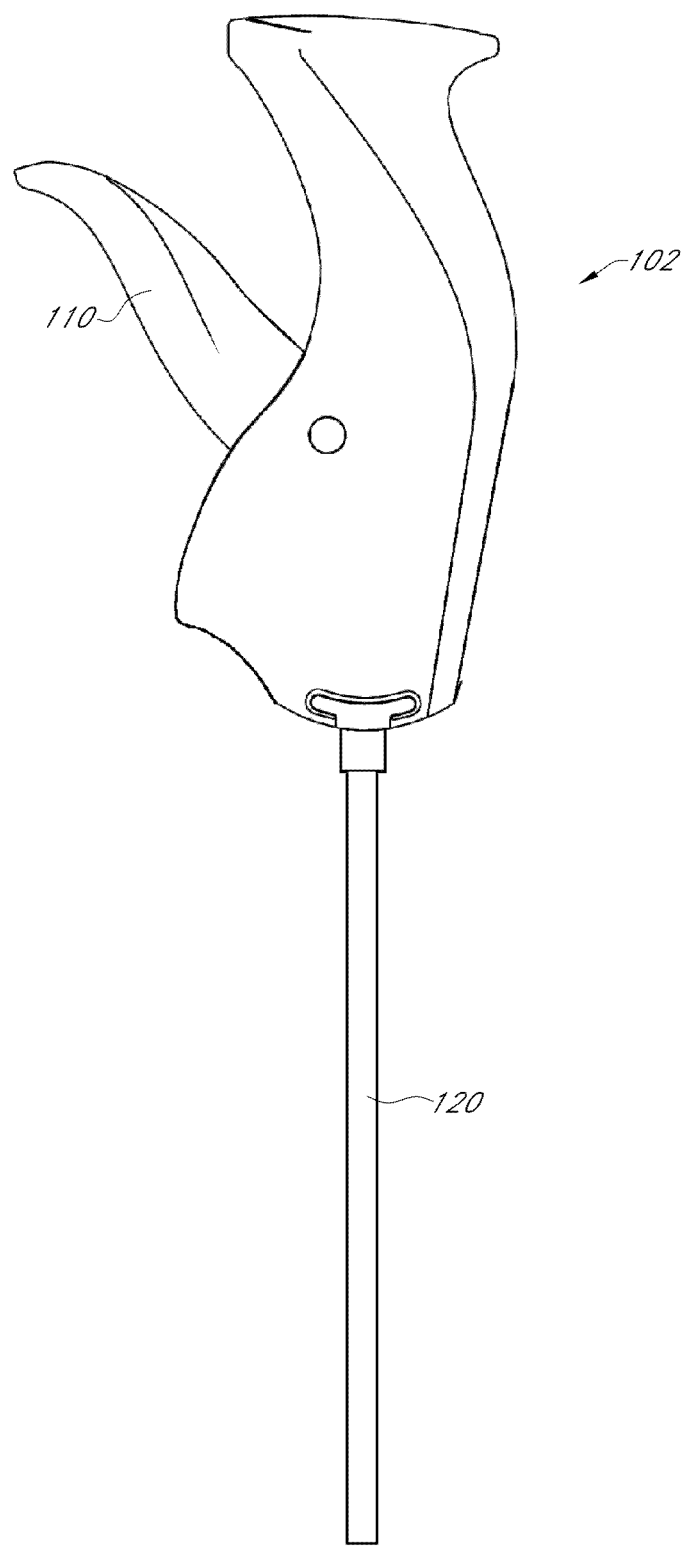
FIG. 2F illustrates a side view of another example embodiment of a bone graft delivery device.
Figure 2G:
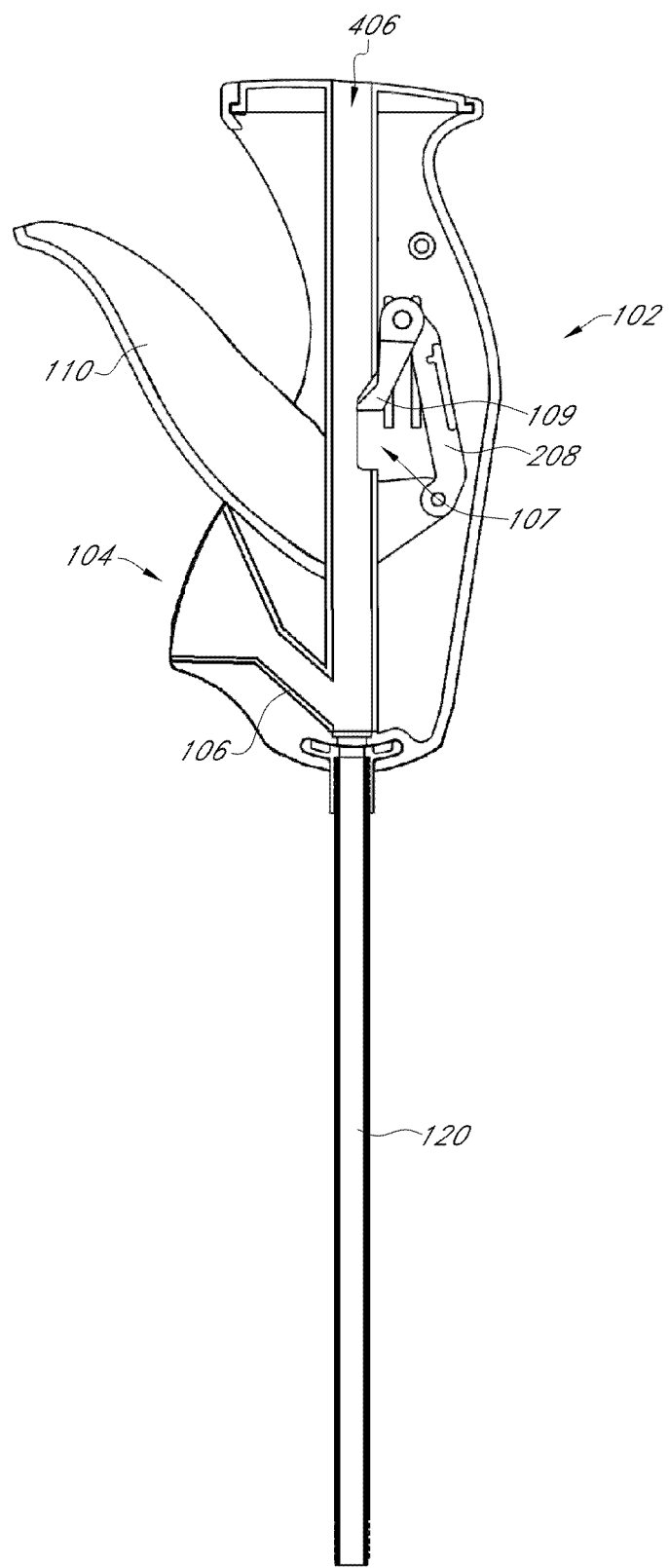
FIG. 2G illustrates a section view of the bone graft delivery device of FIG. 2F.
Figure 2H:
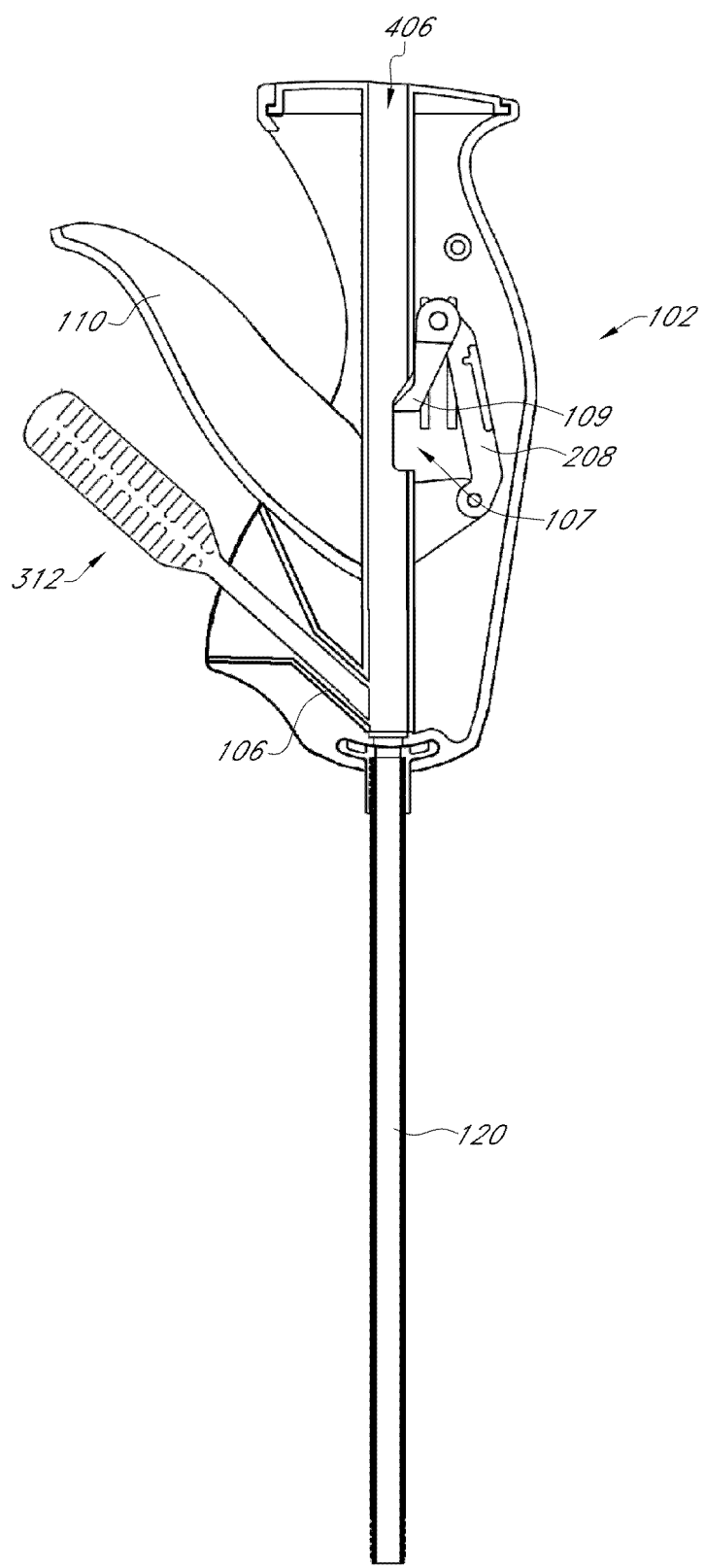
FIG. 2H illustrates a section view of the bone graft delivery device of FIGS. 2F and 2G including a pusher rod.
Figure 2I:
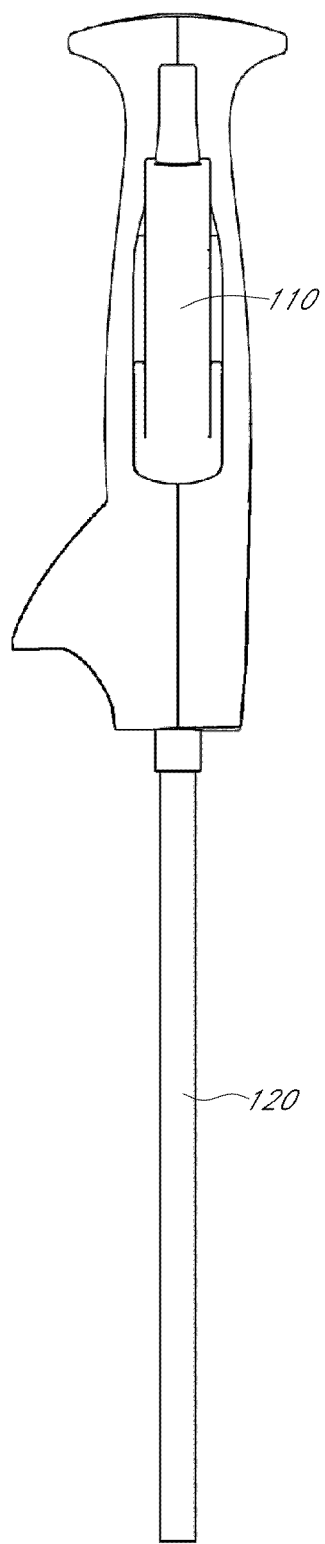
FIG. 2I illustrates a bottom view of another example embodiment of a bone graft delivery device.
Figure 2J:
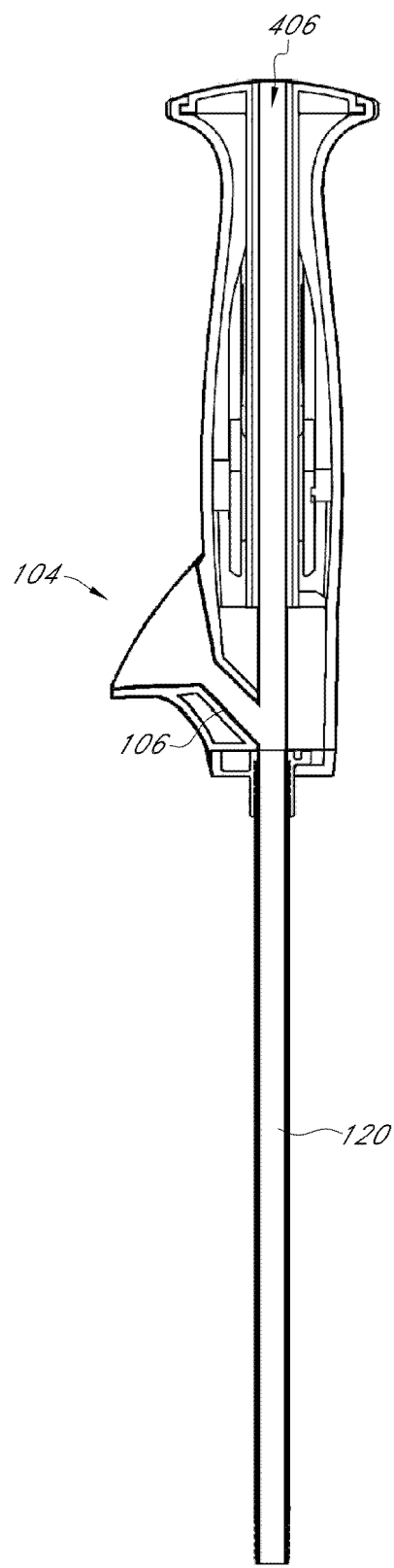
FIG. 2J illustrates a section view of the bone graft delivery device of FIG. 2I.
Figure 2K:
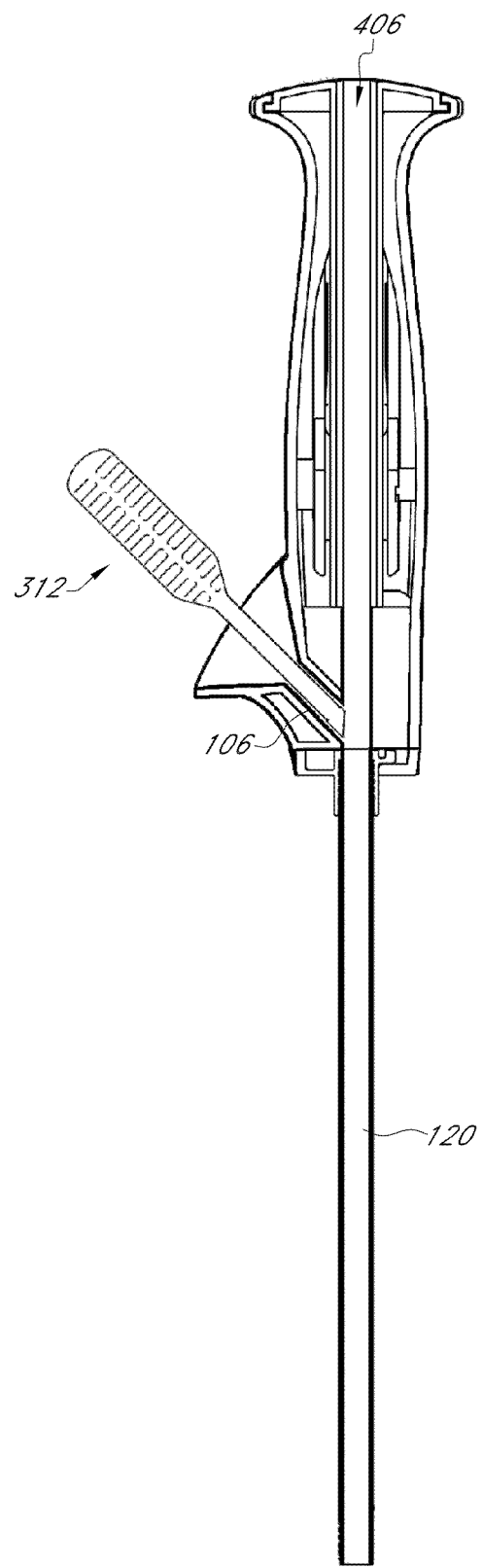
FIG. 2K illustrates a section view of the bone graft delivery device of FIGS. 2I and 2J including a pusher rod.

FIGS. 2F-2H illustrate an alternative embodiment in which the funnel 104 is located on the same side or surface of the handle 102 as the trigger 110. In the illustrated embodiment, the funnel 104 is advantageously located distal to the trigger 110 so that the pusher rod 312, when inserted into the funnel 104, does not interfere with operation of the trigger 110. The embodiment of FIGS. 2F-2H can also include a main channel 406, an angled funnel 104, funnel shaft 106, and distal end 314 of the pusher rod 312, and any suitable ratcheting mechanism similar to the embodiment shown in FIGS. 2C-2E and discussed above. In use, a plunger is inserted into the main channel 406 and tube 120. In the illustrated embodiment, the main channel 406 includes a window 107 to allow the pawl 109 to engage notches on the plunger when the plunger is inserted. Movement of the trigger 110 towards the handle 102 causes the pawl 109 to move distally within the window 107, thereby advancing the plunger and bone graft material. Movement of the trigger 110 away from the handle causes the pawl 109 to slide proximally along the plunger and engage a more proximal notch. In the illustrated embodiment, the window 107 and ratcheting mechanism are located proximal to the intersection of the funnel shaft 106 with the main channel 406, and the ratcheting mechanism does not include a cover or sheath. FIGS. 2I-2K illustrate another alternative embodiment, similar to the embodiment of FIGS. 2F-2H, with the funnel 104 positioned on a side or surface of the handle 102 lateral or generally perpendicular to the trigger 110. In other embodiments, the funnel 104 can be located on any side or surface of the handle 102, for example, opposite the trigger 110, to either side of the trigger, or any other position around the handle 102. The funnel 104 can also be located distal to, even with, or proximal to the trigger 110.

As shown in FIGS. 1A and 1B, the tube 120 of any of the devices described herein can include a permanent bend or curve that may be useful in positioning the device 100 at a desired location, for example, a space between two spinal discs, transverse process, facet joint, lamina, or other target area. Alternatively, the tube 120 may be straight, for example, as shown in FIGS. 2A and 2B, to deliver bone graft material directly into a desired location such as a disc space, transverse process, facet joint, lamina, or other target area. In some embodiments, the tube 120 is somewhat flexible or repositionable and can be manipulated to bend or curve the tube 120 as needed to reach the desired location. In some embodiments, the tube 120 is made of a rigid material, for example, a plastic, composite, or metal. In some embodiments, the tube 120 can be at least partially transparent, which can allow the user to view, for example, the volume or position of the graft material within the tube 120. The tube 120 can also include volume markings to allow the user to monitor the amount of graft material delivered to the target site and remaining in the tube 120, for example, as shown in FIGS. 4N-4O. In some embodiments, the tube 120 includes one or more radiopaque markers to allow for visualization on, for example, x-ray or fluoroscopy. The tube 120 is generally hollow to allow for the passage of bone graft material through the lumen of the tube 120. The tube 120 and lumen can have various diameters, for example, for different applications and/or target locations.

Figure 5A:
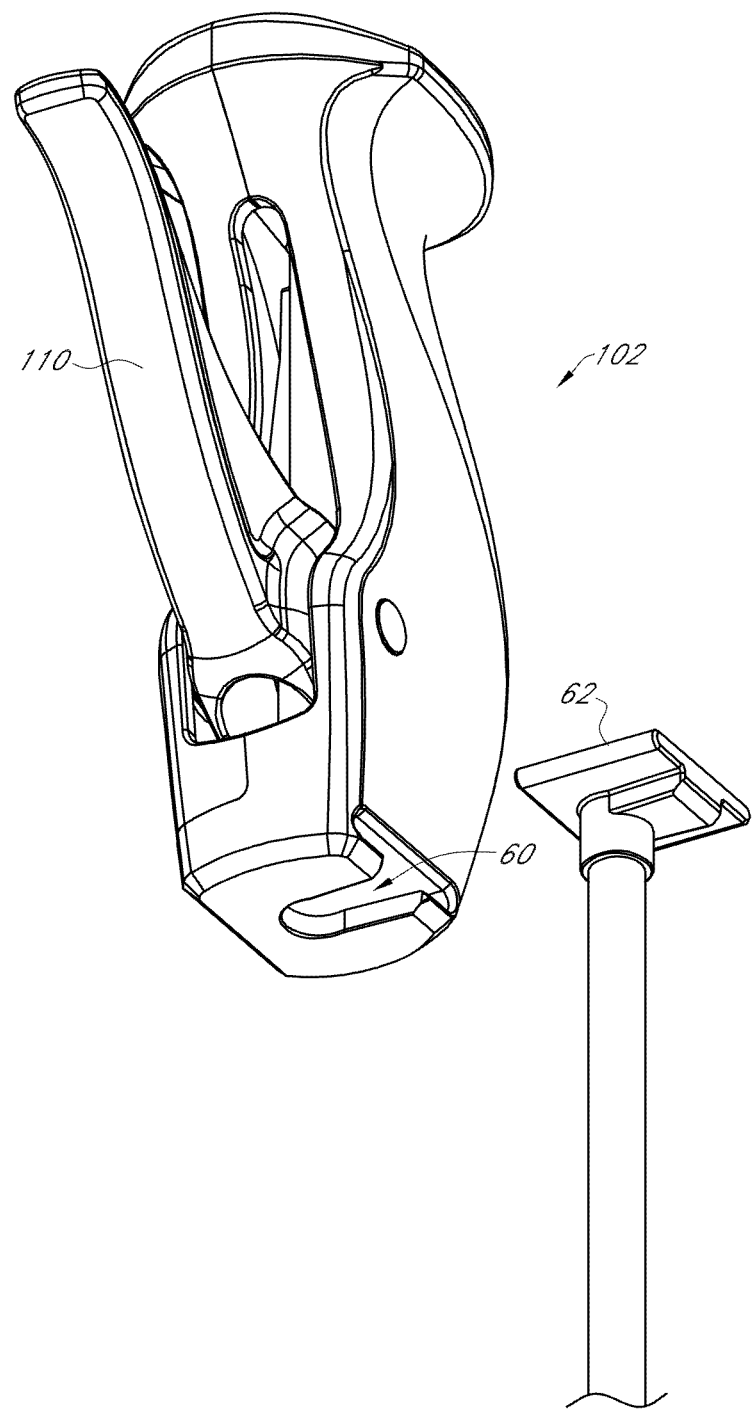
FIGS. 5A and 5B illustrate an example embodiment of a bone graft delivery device having a modular handle and tube construction.
Figure 5B:
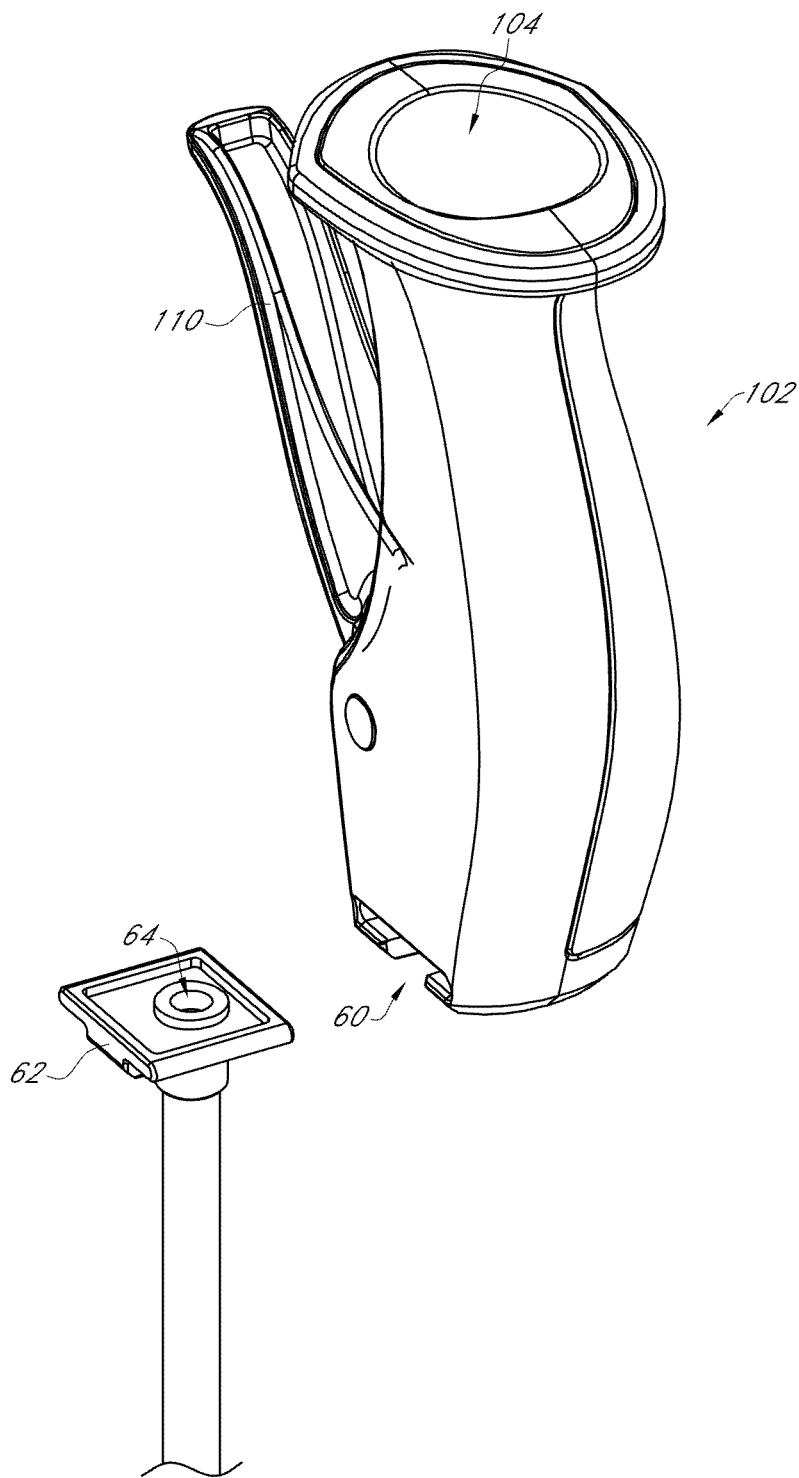

In some embodiments, the tube 120 can be integrally formed with or permanently coupled to the handle 102. In other embodiments, the bone graft delivery device 100 can have a modular construction so that various tubes 120 can be selected and coupled to the handle 102. Such a modular construction can advantageously allow the user to interchange straight and curved handles and/or handles having various other features depending on the target location, particular patient, and/or other factors. As shown in FIGS. 5A and 5B, the distal end of the handle 102 or any of the handles described herein can include a recess 60 configured to receive a base 62 coupled to or integrally formed with the tube 120. The base 62 can be coupled to the tube 120 via a threaded coupling, press fit, or any other suitable means. For example, in the embodiment shown in FIGS. 4N-4T, the tube 120 includes external threads 125a at or near a proximal end of the tube configured to mate with internal threads in the base 62. As shown in FIG. 5B, the base 62 can include an aperture to allow fluid communication between the funnel shaft 106 in the handle 102 and the tube 120. The tube 120 can also be coupled to the handle 102 by any other appropriate means.

Figure 6A:
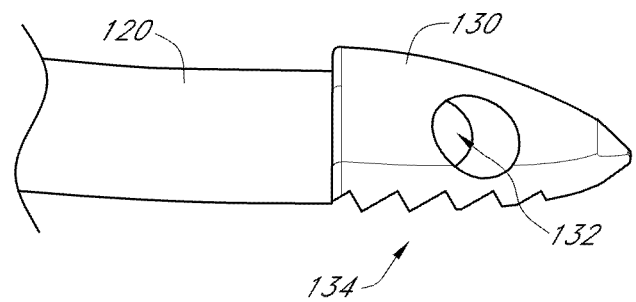
FIGS. 6A-6C illustrate various views of a distal tip of the bone graft delivery device of FIGS. 1A and 1B.
Figure 6B:
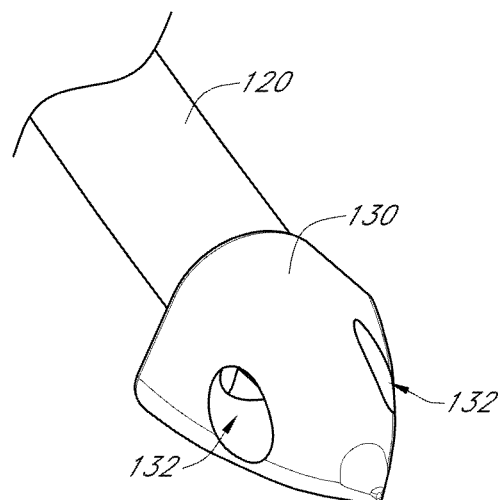
Figure 6C:
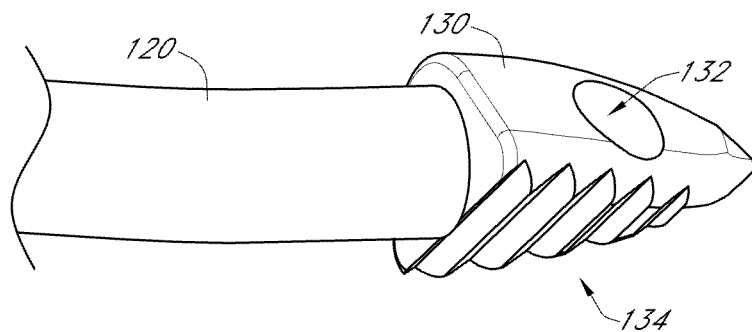
Figure 6D:
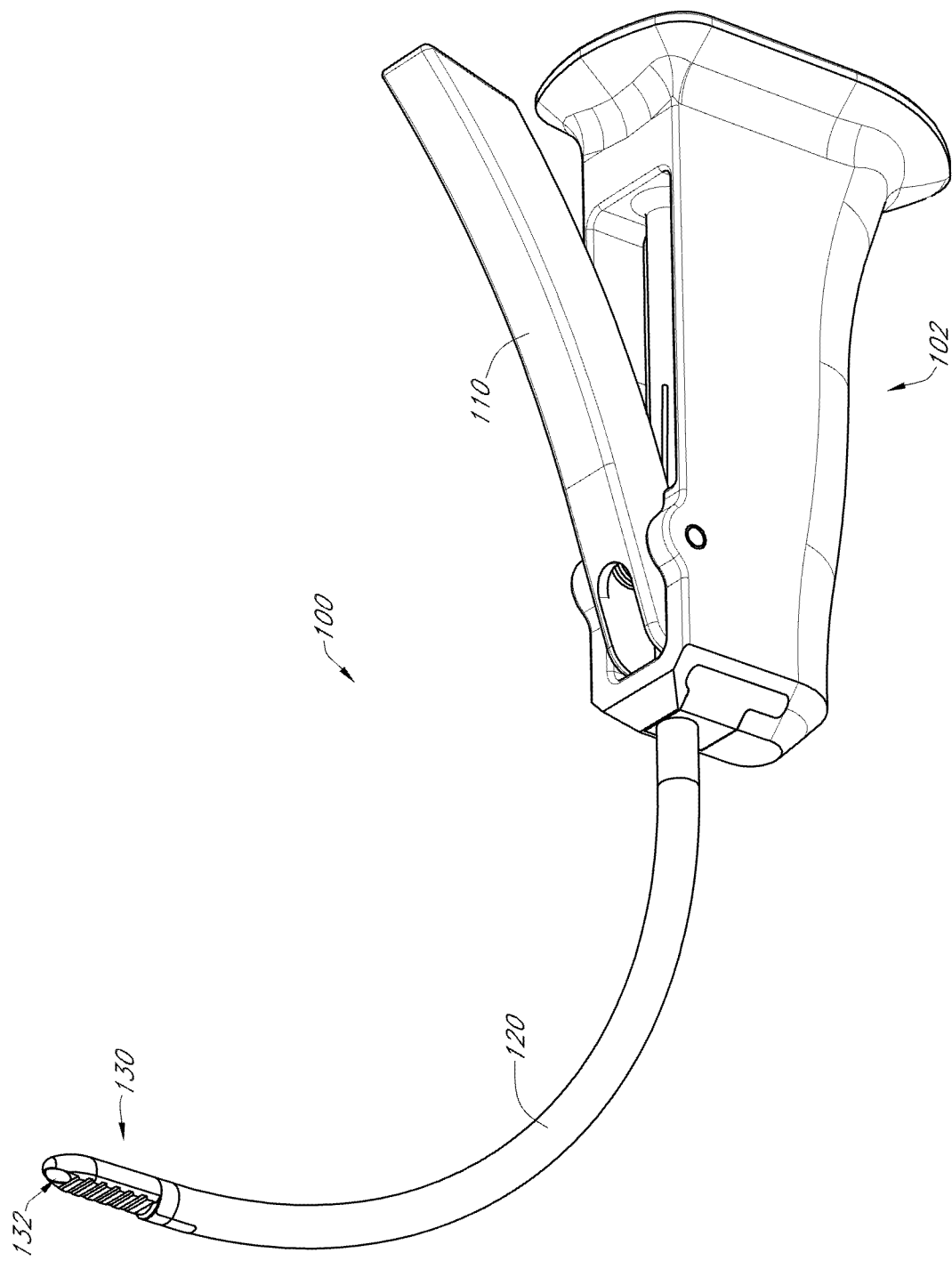
FIG. 6D illustrates a perspective view of an example embodiment of a bone graft delivery device having a curved tube.
Figure 6E:
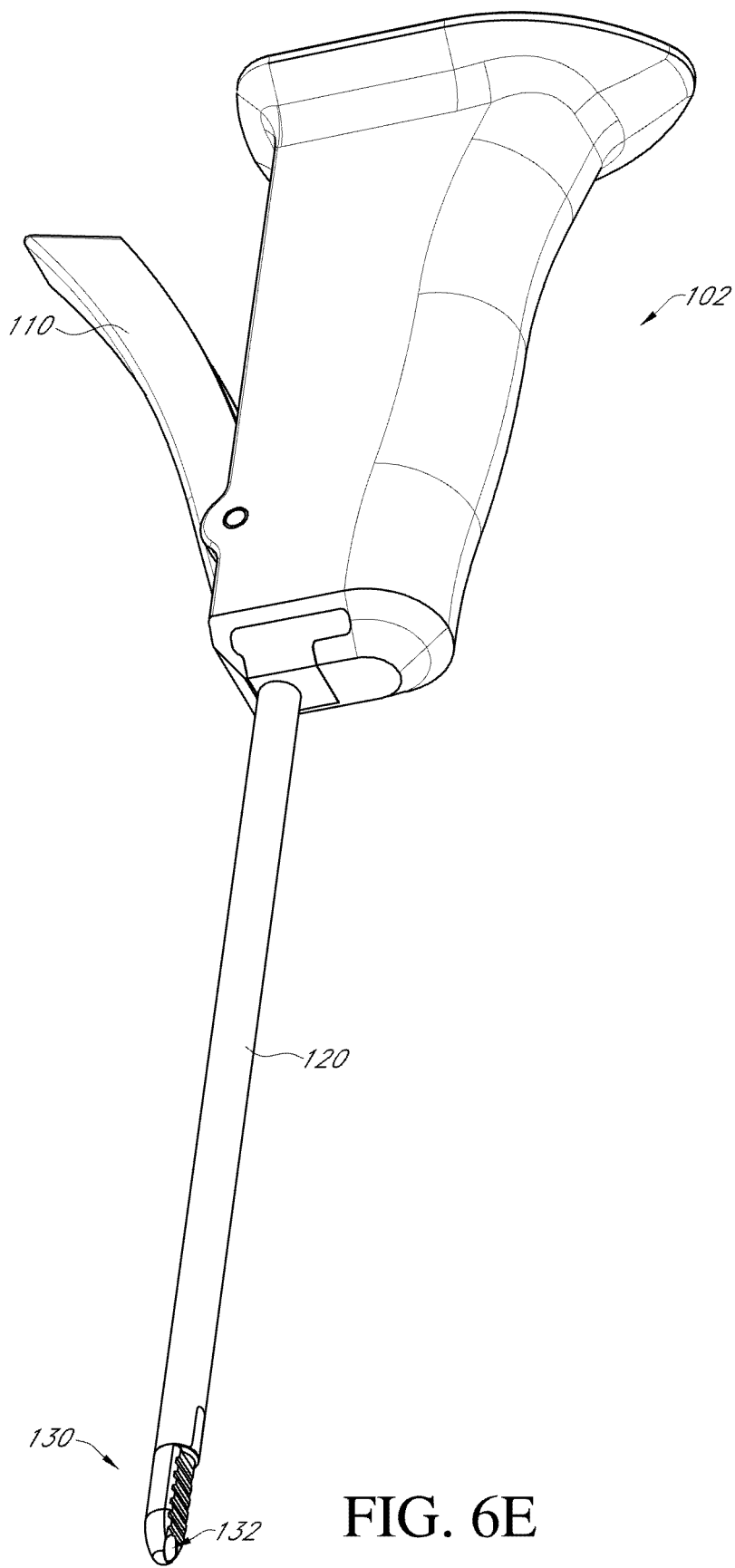
FIG. 6E illustrates a perspective view of an example embodiment of a bone graft delivery device having a straight tube.
Figure 6F:
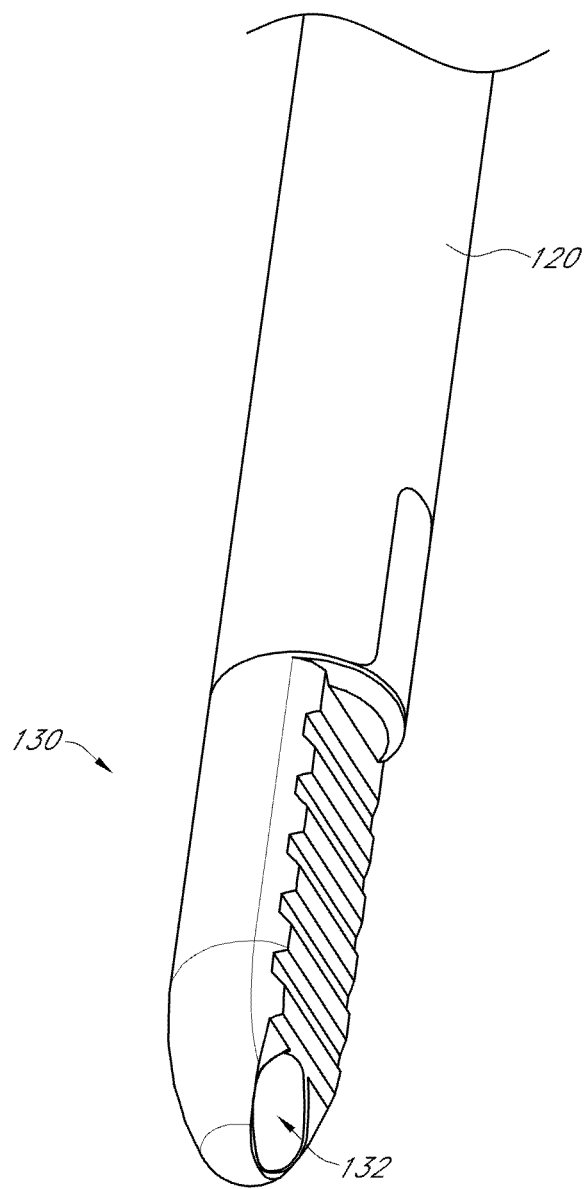
FIG. 6F illustrates an enlarged view of a rasping distal tip of the bone graft delivery device of FIG. 6E.
Figure 6G:
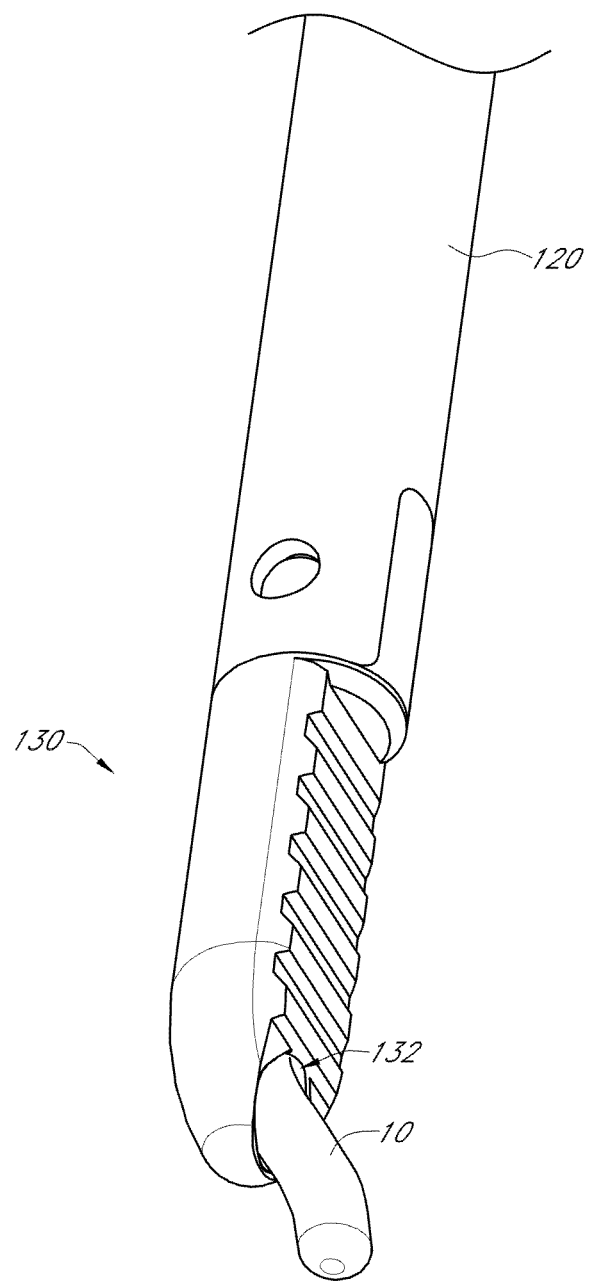
FIG. 6G illustrates the distal tip of FIG. 6F extruding bone graft material.

As shown in FIGS. 6A-6C, a distal end of the tube 120 (which may be any of the tubes described herein) can include a tip 130. The tip 130 can be integrally formed with or coupled, removably or permanently, to the tube 120. In some embodiments, the tube 120 and tip 130 can be a modular system such that different tips can be selected and coupled to the tube 120 for different procedures and/or target locations. The tip 130 can be made of a metallic, radiopaque material to facilitate visualization on, for example, fluoroscopy or x-ray. Alternatively, the tip 130 may be made of another material, for example a durable medical plastic or a composite material, and may include markers to facilitate visualization. In the illustrated embodiment, the tip 130 is somewhat bullet-shaped with a generally triangular cross-section; however, other shapes and configurations are also possible. For example, the tip 130 can be generally flat as shown in the example embodiments of FIGS. 6D-6G. In some embodiments, for example as illustrated in the example embodiment of FIG. 6H-6I, the tip 130 is generally conical. This shape can be beneficial for delivering bone graft material to, for example, a facet joint. In some embodiments, the tip 130 is pointed and/or sharp to dissect or split muscle and tissue as it is advanced through the patient's skin and body to the surgical location. Alternatively, the tip 130 can be blunt to allow for displacement of muscle without risk of cutting of nerves or other tissue. The tip may have a single or multiple openings 132 in fluid communication with the tube 120 lumen and configured to deliver the bone graft material 10 from the tube 120, as shown in FIG. 6G, to the desired location.

Figure 6H:
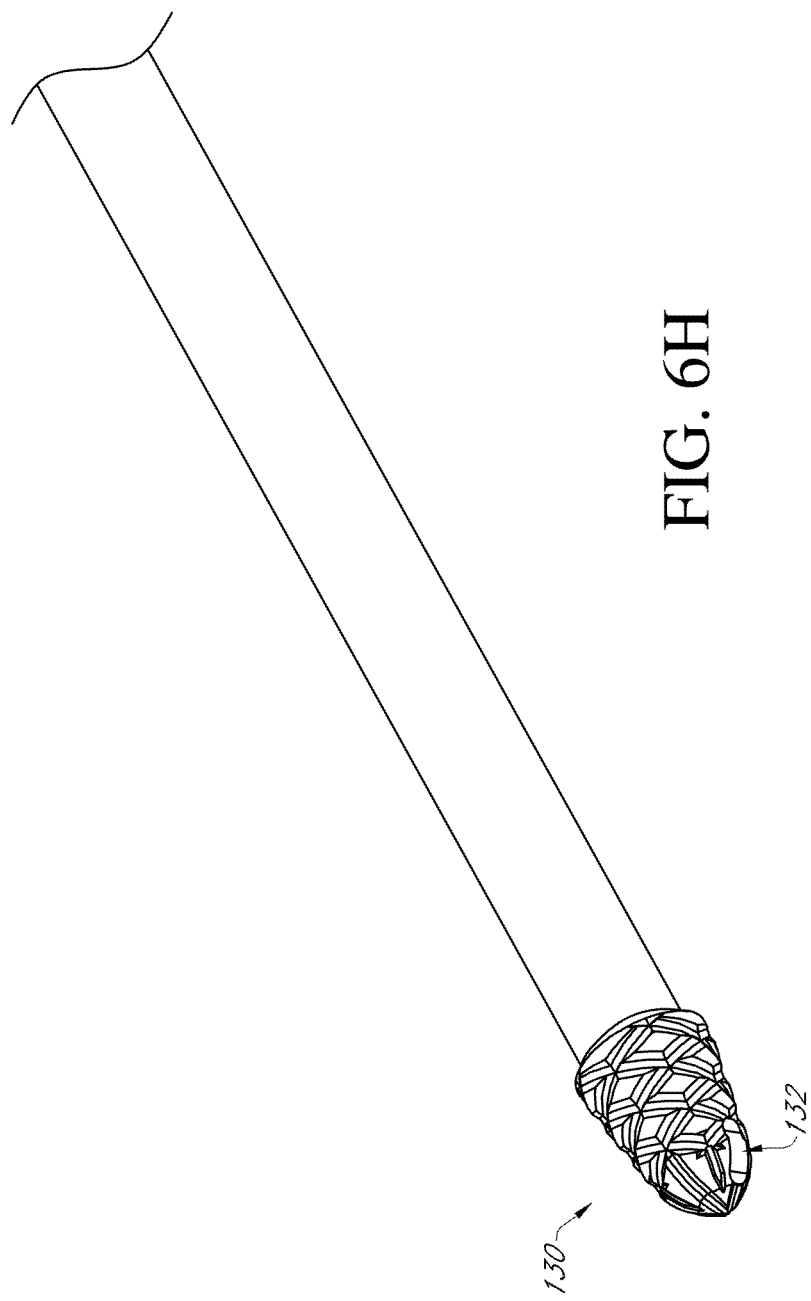
FIG. 6H illustrates an example embodiment of a rasping distal tip coupled to a tube of a bone graft delivery device.

In some embodiments, at least one side or area of the tip 130 includes a series of jagged edges or other suitable surface 134 configured to serve as a rasp for scraping bone. As shown in FIGS. 6A and 6C, the edges may be triangular in shape, and as shown in in FIGS. 6D-6G, they may be flat. With respect to the embodiment shown in FIGS. 6D-6G, the jagged edges may form a plurality of flat surfaces parallel with each other all within the same plane. In some embodiments, for example as shown in FIGS. 6H-6I, the rasping surface 134 can include a roughened surface extending around an outer surface of the tip. The rasp may be operated manually or by mechanical, battery powered, electric, pneumatic, or any other means of force to allow for decortication of the area to receive the bone graft material. In some embodiments, the opening(s) 132 for delivering bone graft material is located on a side(s) or portion(s) of the tip 130 that does not include a rasping surface, for example as shown in FIGS. 1A-1B and 6A-6C. In some embodiments, the opening(s) 132 is located on a side(s) or portion(s) that does include a rasping surface, for example as shown in FIGS. 6D-6I and 8A.

In some embodiments, the delivery device 100 includes a sleeve slidably or telescopingly disposed over the tip 130. In some embodiments, the sleeve can extend to a proximal end of the tube 120 adjacent the handle 102 so that a user can distally advance or proximally retract the sleeve by manipulating a proximal end of the sleeve. In other embodiments, the sleeve extends over only a portion of the tube 120 or over only the tip 130 and the delivery device 100 includes an actuating mechanism that allows the sleeve to be advanced and retracted. The sleeve can be disposed over the tip 130 during insertion of the tip 130 to the target area to advantageously protect skin, tissue, and/or muscle along the insertion path from damage or injury from the rasping surface 134 and to allow the tip 130 to pass through the skin, tissue, and/or muscle more easily. Once the tip is positioned in the target location, the sleeve can be proximally retracted to expose the rasping surface 134 for decortication of the target area. After decortication and/or after delivery of the bone graft material, the sleeve can be distally advanced to cover the rasping surface 134 for withdrawal of the tip 130 from the body.

Figure 7A:
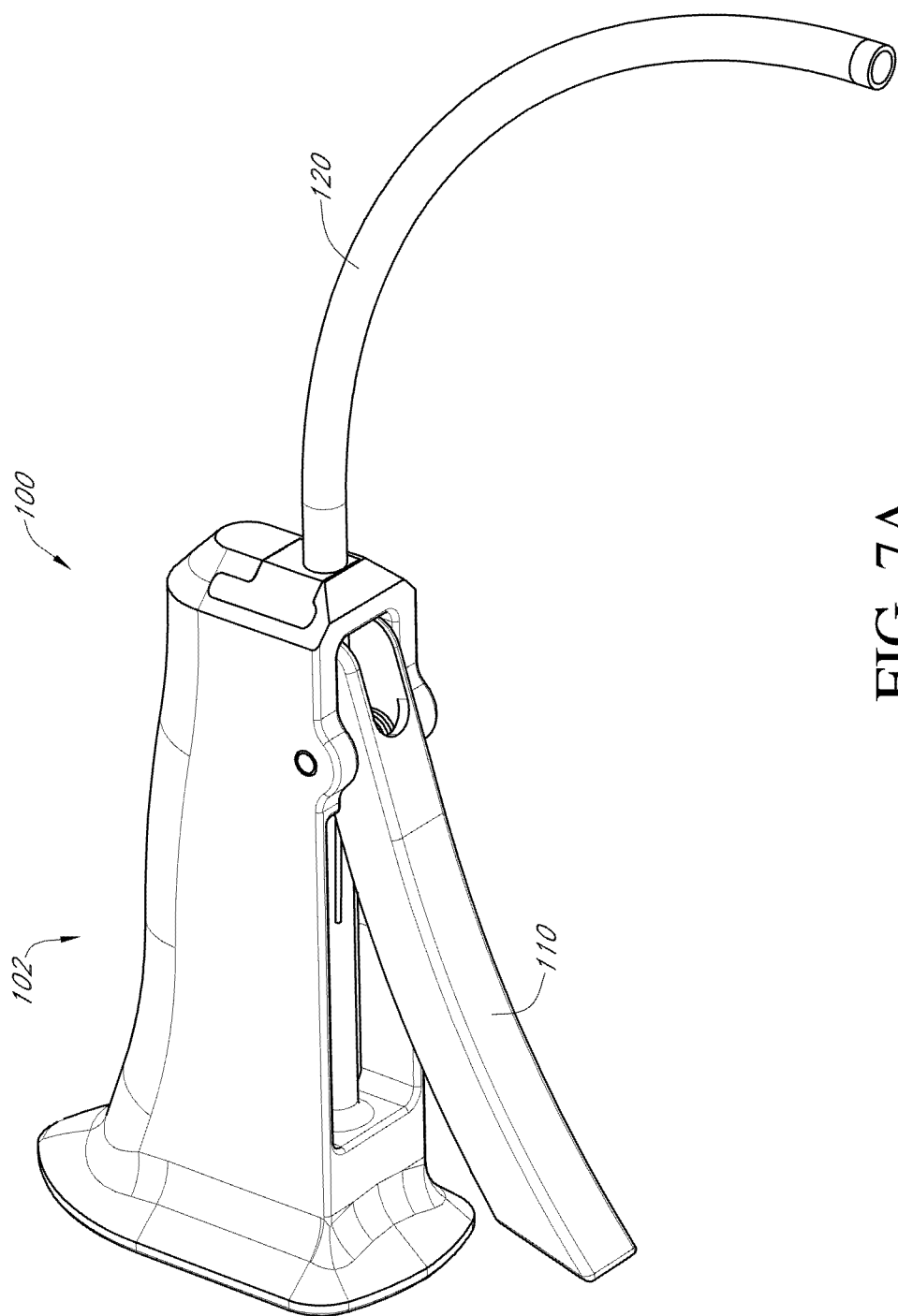
FIG. 7A illustrates a perspective view of an example embodiment of a bone graft delivery device.
Figure 7B:
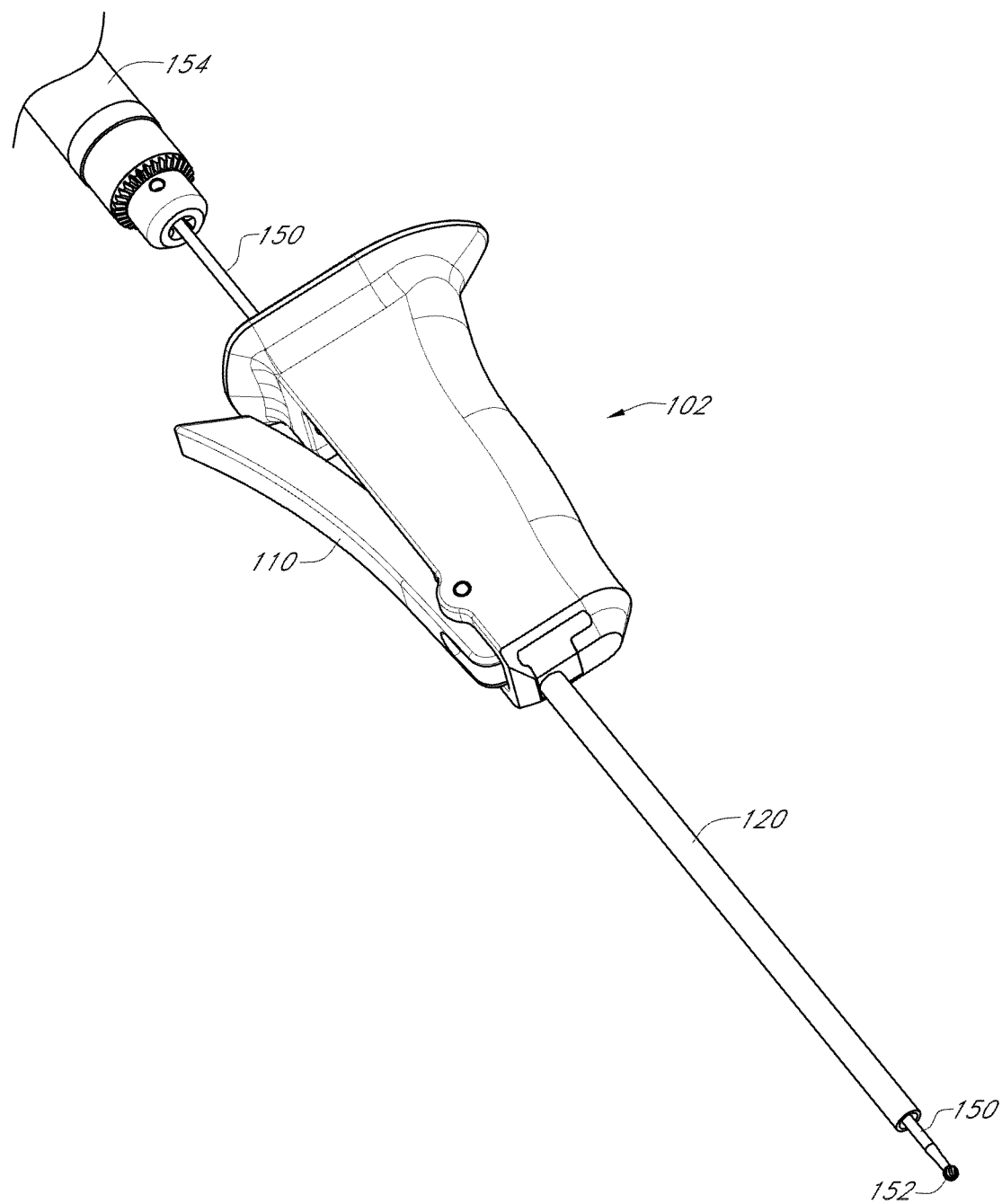
FIG. 7B illustrates a perspective view of an example embodiment of a bone graft delivery device including a shaft having a distal burr disposed therethrough.
Figure 7C:
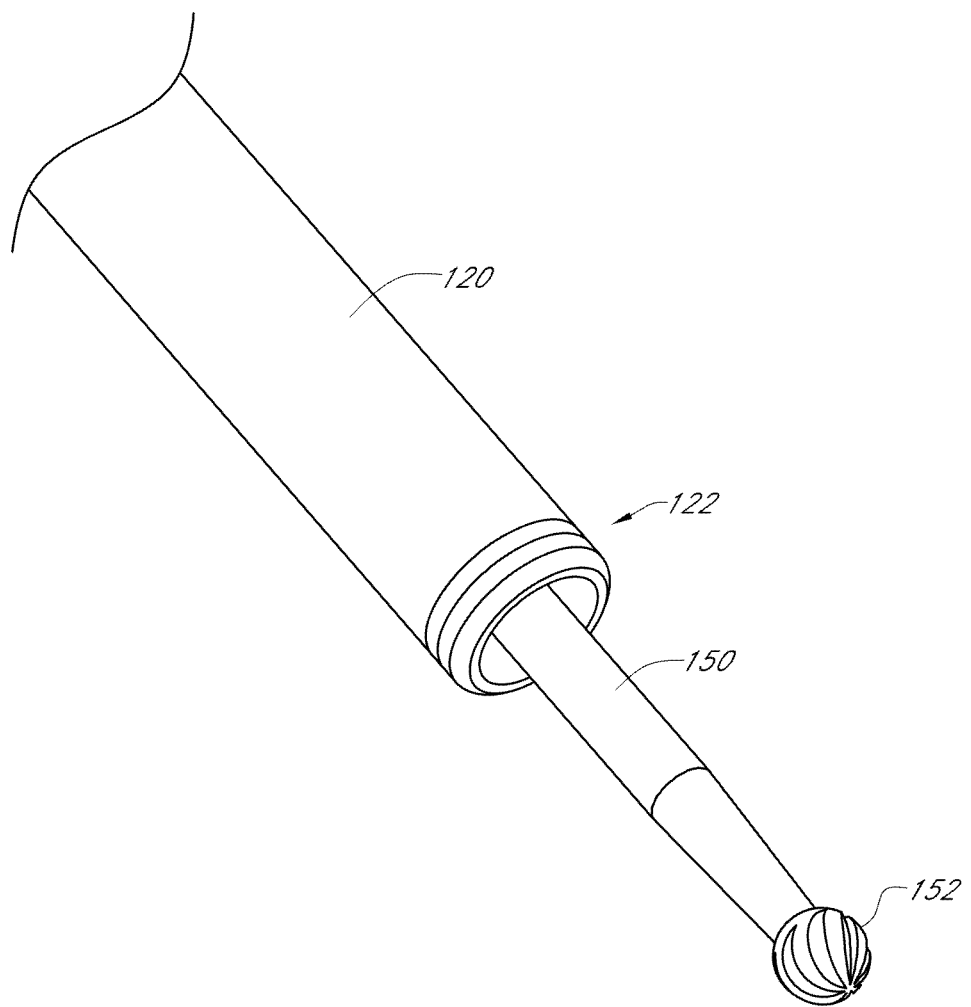
FIG. 7C illustrates an enlarged view of the distal end of the bone graft delivery device of FIG. 7B.

In some embodiments, the distal end of the tube 120 does not include a rasping tip 130, for example as shown in FIGS. 7A-7C. In some such embodiments, an elongate shaft 150 having a burr 152 at a distal end can be inserted through the tube 120 as needed or desired to decorticate a target area, for example as shown in FIGS. 7B and 7C. The burr 152 can have various shapes and configurations, for example, a generally spherical shape as shown in FIGS. 7B and 7C, a bullet shape similar to the distal tip 130 shown in FIGS. 6A-6C, a generally flat shape similar to the distal tip 130 shown in FIGS. 6D-6G, a generally conical shape as shown in FIGS. 6H-6I, or any other suitable shape or configuration. The use of a separate instrument for decortication can advantageously allow the user to select different burrs, rasps, or the like for different patients, target areas, or situations. The elongate shaft 150 and burr 152 can be operated manually. Alternatively, a proximal end of the shaft 150 can be coupled to a drill 154 or another device to provide decortication by mechanical, battery powered, electric, pneumatic, or any other means of force.

Figure 4W:
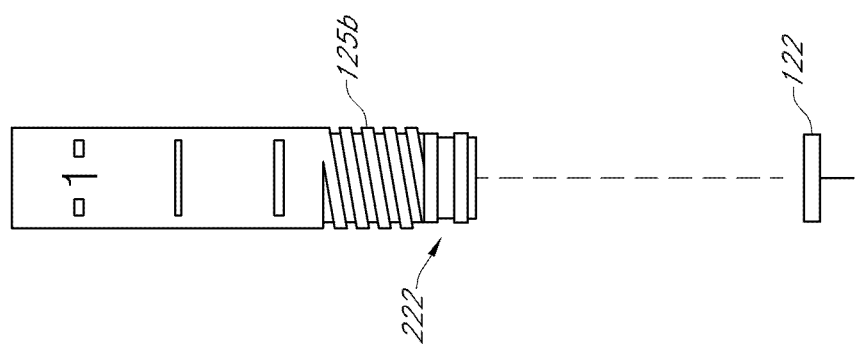
FIG. 4W illustrates a radiopaque ring configured to be placed on a distal end of a tube of a bone graft delivery device.

In some such embodiments, the distal end of the tube 120 includes a radiopaque ring or other marker 122 as shown in FIG. 7C to allow for visualization on, for example, x-ray or fluoroscopy. In some embodiments, the radiopaque ring 122 can be used to assist the user in assessing depth during the procedure. In some embodiments, for example as shown in FIG. 4O, the radiopaque ring 122 can be press fit or snapped onto the distal end of the tube 120 during manufacturing and assembly. In some embodiments, for example as shown in FIG. 4W, the radiopaque ring 122 can be press fit or snapped into a groove 222 near a distal end of the tube 120. In the illustrated embodiment, the groove 222 is distal to the threads 125b configured to receive the tube end cap 124 and is therefore covered by the tube end cap 124 when the tube end cap 124 is coupled to the tube 120. In some embodiments, the radiopaque ring 122 can be co-molded with the tube 120 during manufacturing.

Figure 10A:
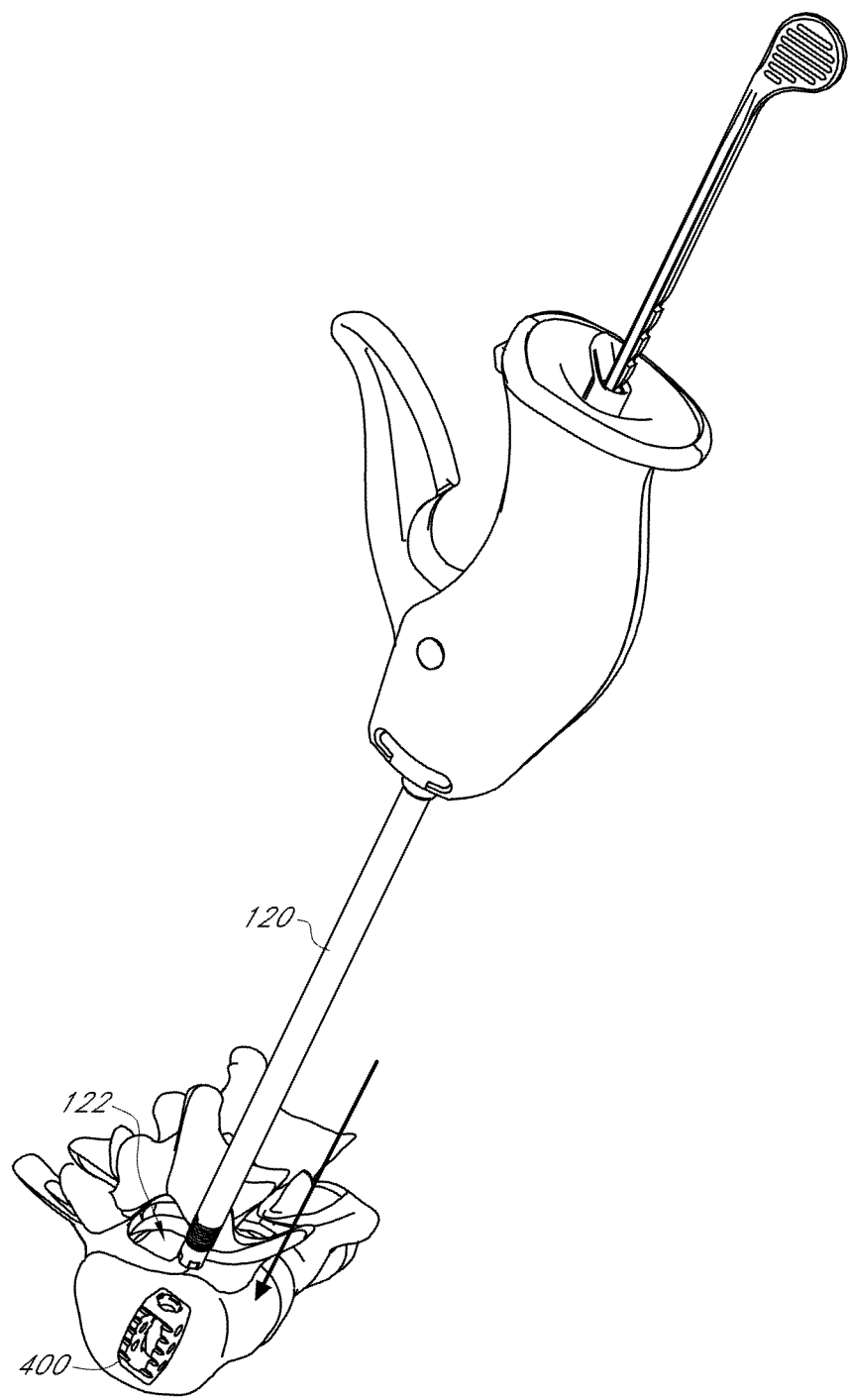
FIGS. 10A-10E illustrate a bone graft delivery device configured to deliver bone graft to an interbody device.
Figure 10B:
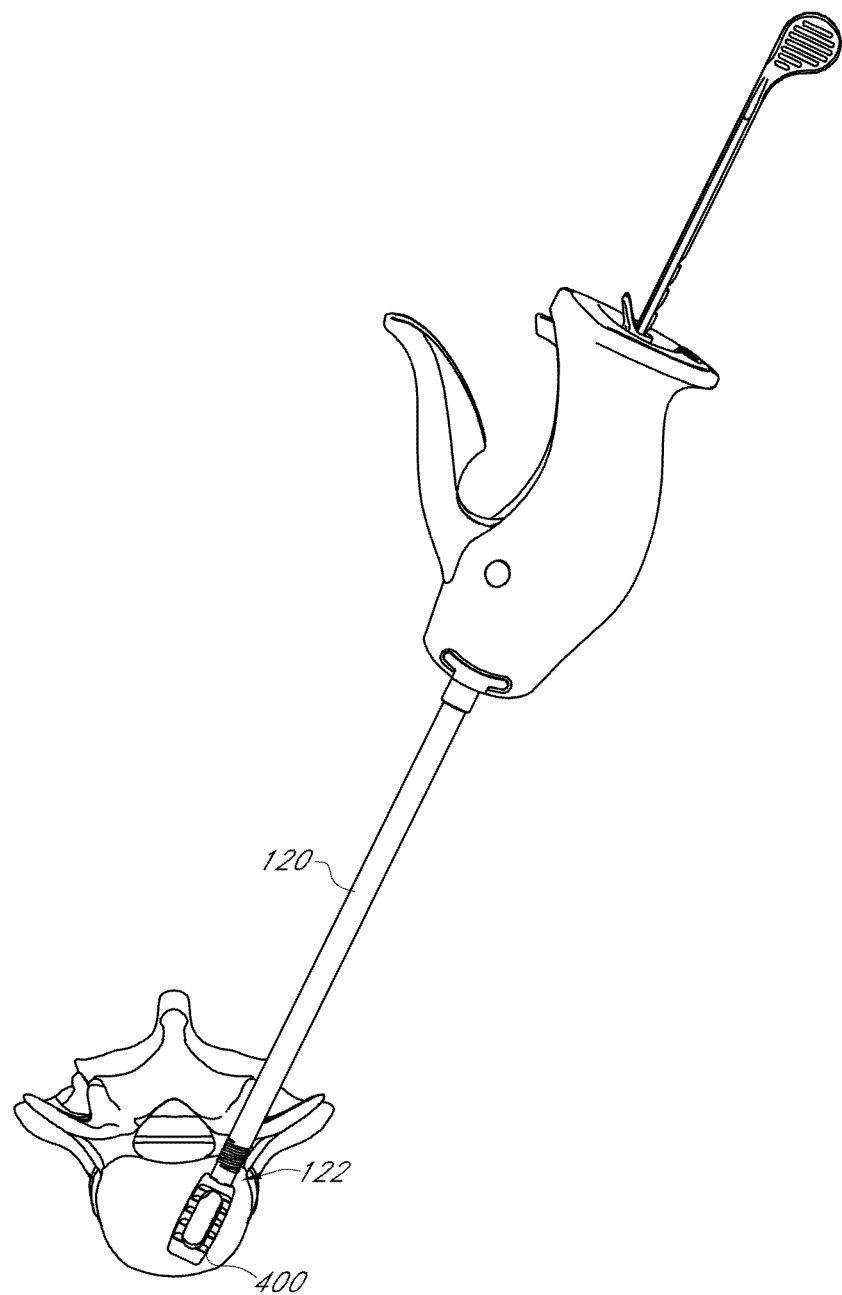
Figure 10C:
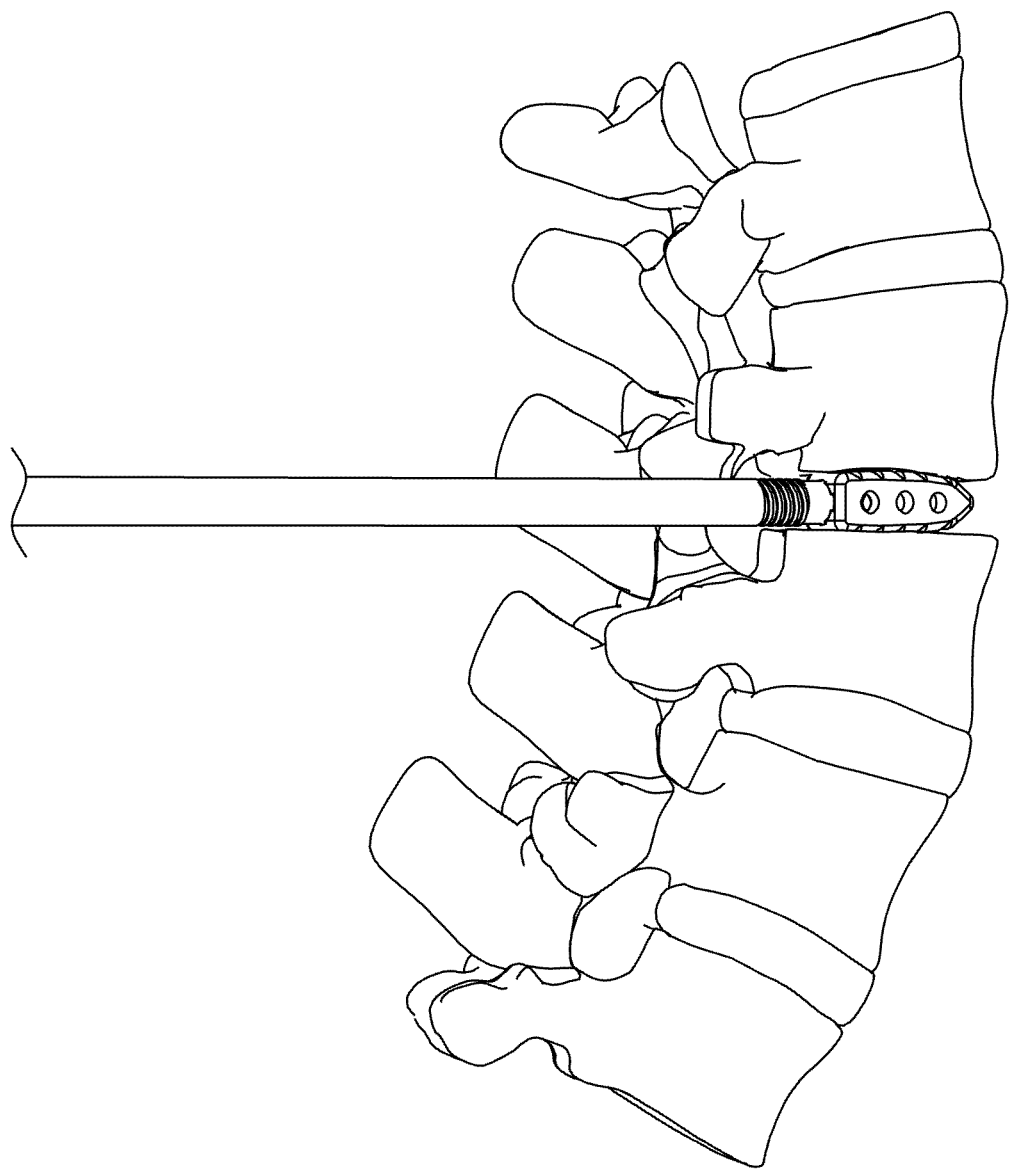
Figure 10D:
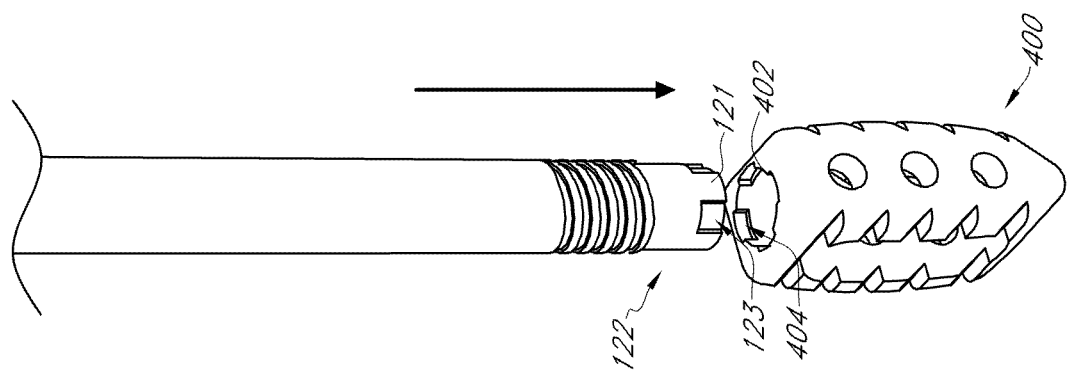
Figure 10E:
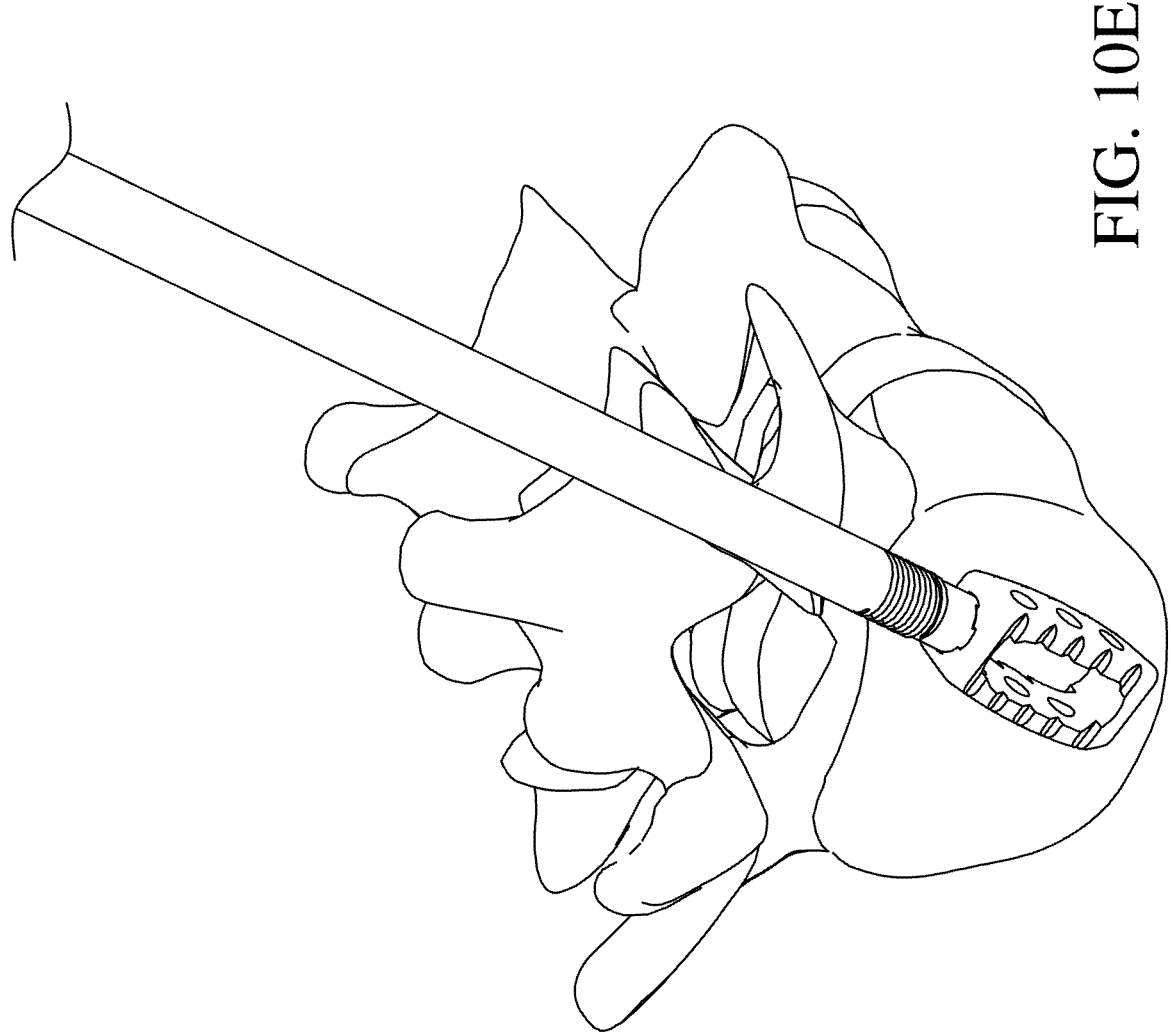

In some embodiments, the bone graft delivery device 100 can be configured to deliver bone graft material inside an interbody cage or other interbody device that has been disposed within a disc space. In some cases, inserting an interbody cage after delivering bone graft material can disrupt the placement of the bone graft material. Delivering the bone graft material after inserting the interbody cage and inserting the bone graft material within the interbody cage can help ensure the bone graft material is placed where desired or required. In some embodiments, an attachment member can be provided to couple the distal end of the tube 120 of the bone graft delivery device 100 to the interbody cage. Bone graft material is delivered through the tube 120 and attachment member and into the interbody cage. Various attachment members can be manufactured and/or provided for use with various interbody cages or other interbody devices. In some embodiments, the distal end of the tube 120 itself includes features configured to engage corresponding features on an interbody device. FIGS. 10A-10E illustrate an example embodiment of a tube 120 having a distal end 122 configured to engage an interbody cage 400. The distal end 122 of the tube 120 can be coupled to the cage 400 after the cage 400 has been placed in the disc space as shown in FIGS. 10A and 10B. As shown in FIG. 10D, the distal end 122 of the tube 120 includes alternating ridges 121 and recesses 123 configured to mate with corresponding recesses 404 and ridges 402 on the cage 400. In some such embodiments, various tubes 120 with different engagement features can be manufactured and/or provided for use with various interbody devices, and the user can select the appropriate tube 120 after selecting the interbody device to be used.

Figure 8A:
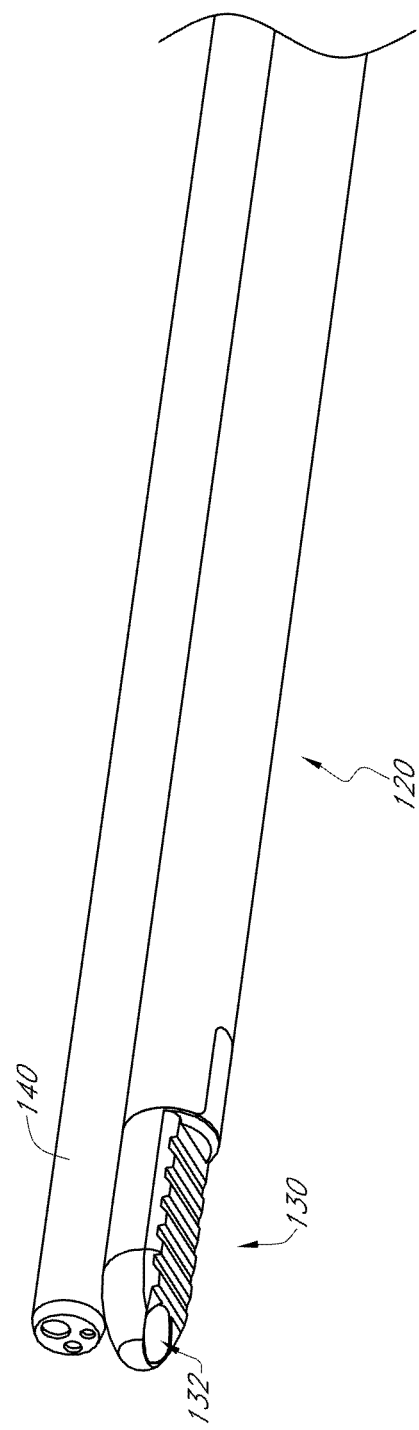
FIG. 8A illustrates a distal section of an example embodiment of a bone graft delivery device including an endoscope.
Figure 8B:
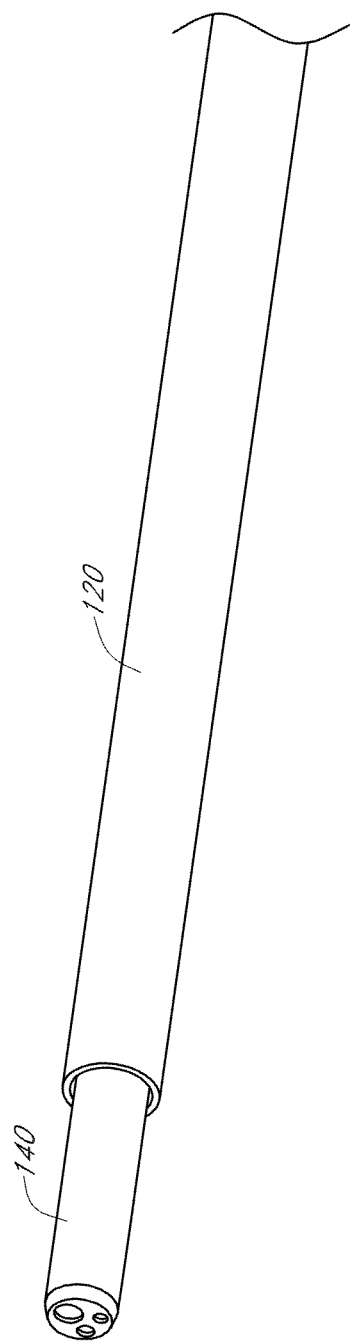
FIG. 8B illustrates a distal section of another example embodiment of a bone graft delivery device including an endoscope.

In some embodiments, the bone graft delivery device 100 can include an endoscope or endoscopic camera to allow for visualization during insertion of the tip 130 to the target area, decortication, and/or delivery of the graft material. This can advantageously allow the physician to visualize muscles, nerves, and other tissue and structures under the skin to help avoid and inhibit damage to sensitive structures. As shown in FIG. 8A, an endoscope 140 can extend along the tube 120 and can be removably or permanently coupled to the tube 120. In some embodiments, the endoscope 140 or camera can extend through the lumen of the tube 120, for example as shown in FIG. 8B.

Figure 9A:
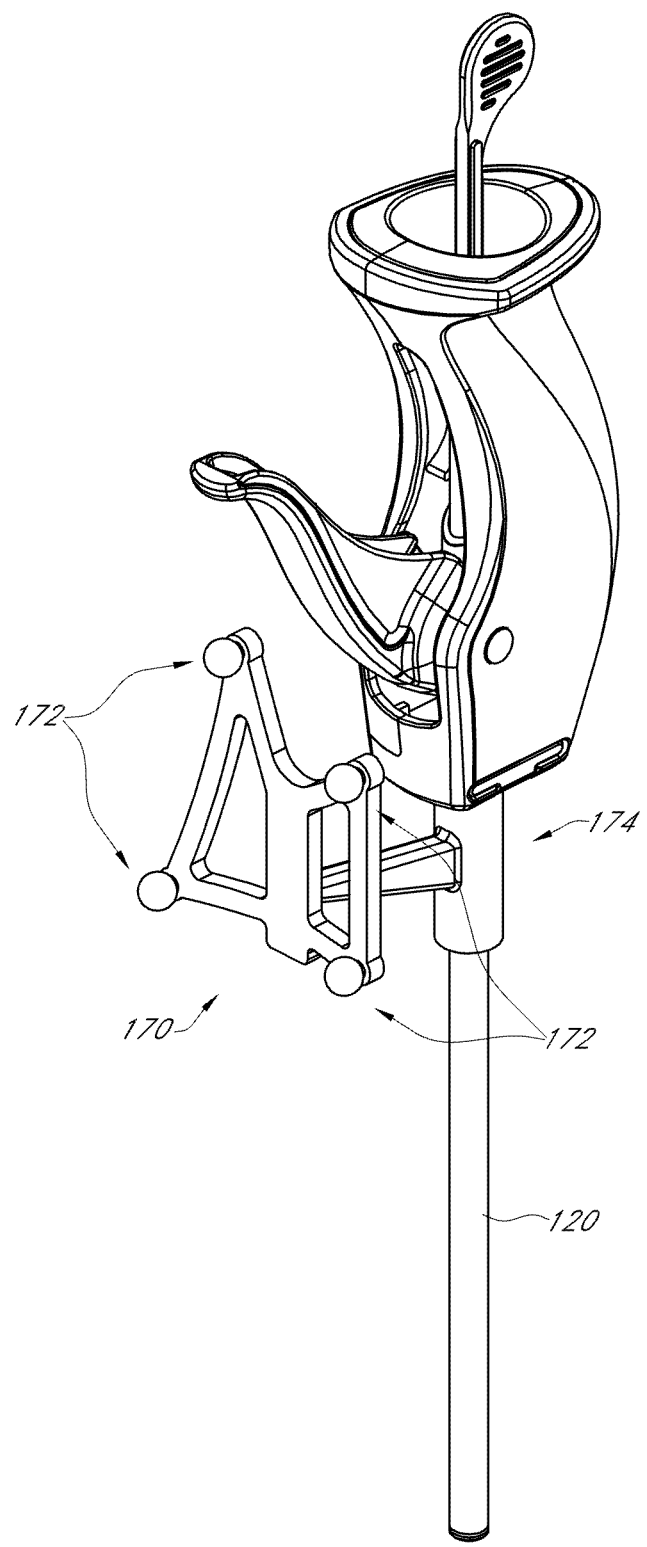
FIGS. 9A and 9B illustrate the bone graft delivery device of FIGS. 2A and 2B with a guide bracket for a surgical navigation system.
Figure 9B:
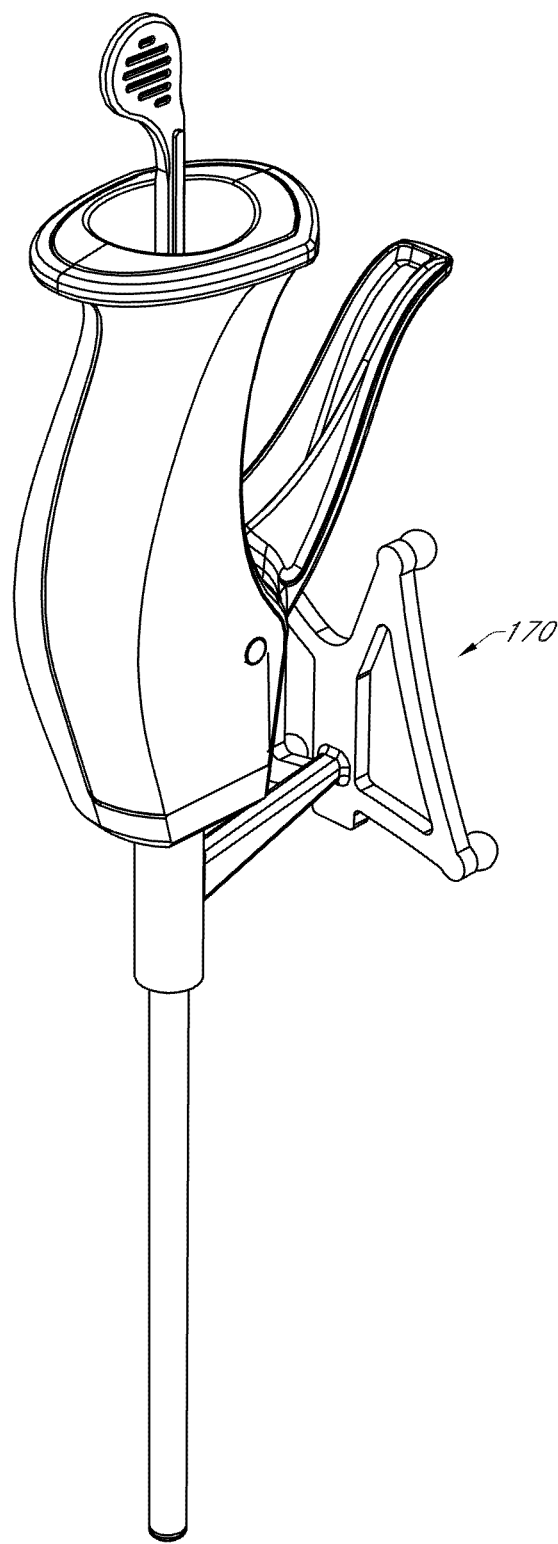

The bone graft delivery device 100 can also or alternatively be used in conjunction with various image-guided surgery systems and devices, such as, for example, StealthStation® Navigation Systems available from Medtronic or other navigation systems. In some embodiments, for example as shown in the example embodiment of FIGS. 9A and 9B, the bone graft delivery device includes a guide 170 having markers 172 configured to be visualized with, for example, fluoroscopy or x-ray. The guide 170 can include a sheath 174 configured to receive the tube 120 to couple the guide 170 to the bone graft delivery device. A surgical navigation system can include an imaging modality, such as an X-ray or CT scanner or fluoroscope, and a camera. In use, during preparation for an image-guided surgical procedure, a reference frame, which can include radiopaque markers, is attached to a pin positioned in a reference location in the patient's spine or other target area. Images are taken, and the image data is transferred to the navigation system for processing and registration. During the procedure, the camera can track the position of the markers 172 on the guide 170 relative to the markers on the reference frame. The navigation system can process images obtained by the camera and/or an imaging modality to display the position of the bone graft delivery device on the pre-operative images. In some embodiments, the navigation system can process images obtained by an endoscopic camera extending alongside or through the tube 120 as described herein.

In some embodiments, one or more handles 102 of a bone graft delivery device can be provided in a system or kit with one or more tips 130, tubes 120, and/or other instruments. The kit can allow a surgeon or other medical personnel to select an appropriate tube 120 and/or tip 130 for the particular patient, procedure, and/or treatment location. As described above, certain tip 130 configurations can be suited for certain target locations. For some procedures, the surgeon may select a curved or straight tube 120 to help improve access to the particular target location. In some embodiments, the kit can include an endoscopic camera. In some embodiments, the kit can include one or more separate rasping instruments. The kit can include various other instruments that might be used during a orthopedic procedure.

In one embodiment, the device 100 described herein may be used in minimally invasive spinal surgery. For example, in a conventional posterolateral spine procedure, screws and or fusion cages may be delivered to adjacent vertebrae using small incisions made in a patient's back. It may additionally be desirable to deliver bone graft material to the surgical location, e.g., to the transverse processes, disc spaces, lamina, or facet joints, through one of these small incisions.

The device described herein is sized to be delivered through a minimally invasive opening made in the patient's skin (e.g., through a skin incision of 4 cm or less), and configured so that the tip can be positioned adjacent a pedicle screw or other desired location. The optional curvature of the tube 120 can facilitate positioning of the tip 130 at desired spinal locations and allows, for example, insertion of the device 100 through an incision over one vertebra, and positioning of the tip 130 at an adjacent vertebra. Alternatively, the device can be delivered through any desired opening made in the patient's skin (e.g., minimally invasive, mini-open, or open). If needed, the optional jagged edges or other surface 134 on the device can be used to decorticate desired bone locations, causing bleeding of the bone and creating a surface that promotes bone fusion. The trigger 110 or other actuation mechanism can then be actuated to deliver bone graft material through the tube 120 lumen and optional openings 132 in the tip 130 to promote fusion of the bone.

In some embodiments, an endoscope or camera can be inserted through the tube 120 and used to help guide the physician or other medical professional to the target location and/or to allow the physician to evaluate the area. If the physician wants to decorticate the bone, the physician can remove the endoscope or camera, insert the shaft 150 having the burr 152 or another suitable rasping instrument, and decorticate the target area. In some embodiments, the tube 120 can be inserted into the patient with the shaft 150 or other rasping instrument already inserted or with a rasping tip 130 attached and the physician can use an endoscope, camera, navigation system, or the like placed alongside, adjacent, or proximal the tube 120 to navigate to and/or evaluate the target area. Once the target location is ready, the physician can remove the shaft 150 or other rasping instrument if present and deliver the bone graft material, for example, using the trigger 110.

Although use of the device 100 has been described with respect to an example spinal procedure, the device 100 can also be used in other spinal procedures and other orthopedic applications to deliver bone graft material to other locations in the body (for example, the femur or tibia).

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Various combinations and subcombinations of the various features described herein are possible. For example, a bone graft delivery device can include a handle and tube and may or may not include a distal rasping tip. The tube can be integrally formed with the handle and/or a distal rasping tip and/or any or all of the components can have a modular configuration such that various tubes and/or distal tips can be selected and exchanged as desired by the surgeon or other user. A bone graft delivery device can have a curved or straight tube. A distal tip can have any suitable configuration, including bullet-shaped, flat, conical, or any other configuration. A bone graft delivery device can be configured to received and/or supplied with various endoscopes, other cameras or imaging equipment, and/or guide brackets for imaging equipment. A bone graft delivery device can include any suitable ratcheting mechanism to advance bone graft material through the device for delivery and may include a plunger and/or pusher rod. Certain embodiments of the invention are encompassed in the claim set listed below.

What is claimed is:

1. A method for delivering bone graft material to a surgical location, comprising:
    loading a bone graft material into a lumen of a bone graft delivery device, the bone graft delivery device comprising:
        an elongate tube, the lumen extending through the elongate tube; and
        a rasp couplable to the elongate tube and comprising a surface suitable for scraping bone;
    coupling a guide for use with an image-guided surgery system to the bone graft delivery device;
    visualizing the guide with the image-guided surgery system;
    advancing the bone graft delivery device towards the surgical location;
    monitoring the position of the bone graft delivery device relative to the surgical location using the image-guided surgery system; and
    advancing bone graft material within the lumen and to the surgical location when the bone graft delivery device is positioned at the surgical location.

2. The method of claim 1, wherein the guide comprises one or more markers, wherein visualizing the guide with the image-guided surgery system comprises visualizing the one or more markers.

3. The method of claim 2, wherein visualizing the one or more markers comprises visualizing the one or more markers using fluoroscopy or x-ray.

4. The method of claim 1, further comprising positioning a reference frame at a reference location of the surgical location, wherein monitoring the position of the bone graft delivery device relative to the surgical location comprises monitoring the position of the bone graft delivery device relative to the reference frame.

5. The method of claim 4, wherein the reference frame comprises one or more radiopaque markers.

6. The method of claim 4, wherein monitoring the position of the bone graft delivery device relative to the reference frame comprises tracking the position of one or more markers of the guide relative to the position of one or more markers of the reference frame.

7. The method of claim 4, further comprising coupling the reference frame to a pin at the reference location.

8. The method of claim 1, wherein the image guided surgery system comprises one or more of an x-ray scanner, a CT scanner, a fluoroscope, and a camera.

9. The method of claim 1, further comprising advancing a plunger into the lumen of the bone graft delivery device to advance the bone graft material within the lumen and to the surgical location when the bone graft delivery device is positioned at the surgical location.

10. The method of claim 9, further comprising advancing the plunger into the lumen of the bone graft delivery device using a handle coupled to a proximal end of the elongate tube.

11. The method of claim 1, further comprising decorticating bone at the surgical location using rasp.

12. A bone graft delivery system, comprising:
    a bone graft delivery device comprising:
        an elongate tube;
        a lumen extending through the elongate tube and configured to receive a bone graft material; and
        a rasp couplable to the elongate tube and comprising a surface suitable for scraping bone;
    a guide configured to couple to the bone graft delivery device, the guide comprising one or more markers; and an image-guided surgery system configured to visualize the one or more markers of the guide.

13. The system of claim 12, wherein the guide is configured to couple to the elongate tube.

14. The system of claim 12, further comprising a reference frame configured to be positioned at a reference location of a surgical location, wherein the image-guided surgery system is configured to visualize the reference frame.

15. The system of claim 14, further comprising a pin coupled to the reference frame.

16. The system of claim 14, wherein the reference frame comprises one or more radiopaque markers, wherein the image guided-surgery system is configured to visualize the one or more radiopaque markers.

17. The system of claim 12, wherein the image guided surgery system comprises one or more of an x-ray scanner, a CT scanner, a fluoroscope, and a camera.

18. The system of claim 12, further comprising a plunger configured to be removeably received in the lumen.

19. The system of claim 18, wherein the bone graft delivery device further comprises a handle at a proximal end of the elongate tube configured to be actuated to deliver bone graft through the elongate tube.

20. The system of claim 12, wherein the surface of the rasp comprises jagged edges.

* * * * *